(12) United States Patent
Denny et al.

(10) Patent No.: US 7,629,332 B2
(45) Date of Patent: Dec. 8, 2009

(54) NITROPHENYL MUSTARD AND NITROPHENYLAZIRIDINE ALCOHOLS AND THEIR CORRESPONDING PHOSPHATES AND THEIR USE AS TARGETED CYTOTOXIC AGENTS

(75) Inventors: William Alexander Denny, Auckland (NZ); Graham John Atwell, Auckland (NZ); Shangjin Yang, Auckland (NZ); William Robert Wilson, Waiuku (NZ); Adam Vorn Patterson, Auckland (NZ); Nuala Ann Helsby, Auckland (NZ)

(73) Assignee: Auckland Uniservices Limited, Auckland (NZ)

( * ) Notice: Subject to any disclaimer, the term of this patent is extended or adjusted under 35 U.S.C. 154(b) by 86 days.

(21) Appl. No.: 10/577,078

(22) PCT Filed: Oct. 29, 2004

(86) PCT No.: PCT/NZ2004/000275

§ 371 (c)(1),
(2), (4) Date: Jul. 13, 2006

(87) PCT Pub. No.: WO2005/042471

PCT Pub. Date: May 12, 2005

(65) Prior Publication Data

US 2007/0032455 A1 Feb. 8, 2007

(30) Foreign Application Priority Data

Oct. 31, 2003 (NZ) ........................... 529249
Sep. 28, 2004 (NZ) ........................... 535618

(51) Int. Cl.
*A61K 31/66* (2006.01)
*C07F 9/02* (2006.01)
(52) U.S. Cl. .................... 514/75; 558/166; 558/177
(58) Field of Classification Search ................ 558/166, 558/177; 514/75
See application file for complete search history.

(56) References Cited

U.S. PATENT DOCUMENTS 6,743,919 B2 * 6/2004 Koya et al. .................. 546/118

FOREIGN PATENT DOCUMENTS

| WO | WO 93/11099 A1 | 1/1993 |
| WO | WO 00/13683 A2 | 3/2000 |
| WO | WO 00/13683 A3 | 3/2000 |
| WO | WO 2004/033415 A1 | 4/2004 |

OTHER PUBLICATIONS

Dogan et al. CAS: 140:419464.*
Palmer, Brian D., et al; "Hypoxia-Selective Antitumor Agents. 9. Structure-Activity Relationships for Hypoxia-Selective Cytotoxicity among Analogues of 5-[$N,N$-Bis(2-chloroethyl)amino]-2,4-dinitrobenzamide"; *J. Med. Chem.*; 1994, 37, pp. 2175-2184.
Helsby, N.A., et al; *Journal of Medicinal Chemistry*; 47(12), pp. 3295-3307 (2004); STN File CA, Abstract No. 141:106328.
Wilson, W.R., et al; *Cancer Research*; 62(5); pp. 1425-1432 (2002); STN File CA, Abstract No. 137:134431.
Friedlos, F., et al; *Journal of Medicinal Chemistry*; 40(8); pp. 1270-1275 (1997); STN File CA, Abstract No. 126:246358.
Palmer, B.D., et al; *Journal of Medicinal Chemistry*; 39(13); pp. 2518-2528 (1996); STN File CA, Abstract No. 125:753.
Anlezark, G.M., et al; *Biochemical Pharmacology*; 50(5); pp. 609-618 (1995); STN File CA, Abstract No. 123:275328.
Khan, A.H., et al; *Chemico-Biological Interactions*; 4(1); pp. 11-22 (1971); STN File CA, Abstract No. 76:54221.

* cited by examiner

*Primary Examiner*—Rei-tsang Shiao
(74) *Attorney, Agent, or Firm*—Nixon & Vanderhye

(57) ABSTRACT

The present invention relates to a novel nitrophenyl mustard and nitrophenylaziridine alcohols, to their corresponding phosphates, to their use as targeted cytotoxic agents; as bioreductive drugs in hypoxic tumors, and to their use in cell ablation, including gene-directed enzyme-prodrug therapy (GPEPT) and antibody-directed enzymeprodrug therapy (ADEPT), in conjunction with nitroreductase enzymes.

20 Claims, 8 Drawing Sheets

NITROPHENYL MUSTARD AND NITROPHENYLAZIRIDINE ALCOHOLS AND THEIR CORRESPONDING PHOSPHATES AND THEIR USE AS TARGETED CYTOTOXIC AGENTS

CROSS REFERENCE TO RELATED APPLICATIONS

This application is the U.S. National Phase of International Application PCT/NZ2004/000275, filed 29 Oct. 2004, which designated the U.S. PCT/NZ2004/000275 claims priority to New Zealand Application Nos. 529249 filed 31 Oct. 2003 and 535618 filed 28 Sep. 2004. The entire content of these applications are incorporated herein by reference.

The present invention relates to novel nitrophenyl mustard and nitrophenylaziridine alcohols, to their corresponding phosphates, to their use as targeted cytotoxic agents; as bioreductive drugs in hypoxic tumours, and to their use in cell ablation, including gene-directed enzyme-prodrug therapy (GDEPT) and antibody-directed enzyme-prodrug therapy (ADEPT), in conjunction with nitroreductase enzymes.

BACKGROUND TO THE INVENTION

The use of tumour-selective prodrugs (relatively inactive compounds that can be selectively converted to more active compounds in vivo) is a valuable concept in cancer therapy (see, for example Denny, *Eur. J. Med Chem.* (2001) 36, 577).

For example a prodrug may be converted into an antitumour agent under the influence of an enzyme that is linkable to a monoclonal antibody that will bind to a tumour associated antigen. The combination of such a prodrug with such an enzyme monoclonal/antibody conjugate represents a very powerful clinical agent. This approach to cancer therapy, often referred to as "antibody directed enzyme/prodrug therapy" (ADEPT), is disclosed in WO88/07378

A further therapeutic approach termed "virus-directed enzyme prodrug therapy" (VDEPT) has been proposed as a method for treating tumour cells in patients using prodrugs. Tumour cells are targeted with a viral vector carrying a gene encoding an enzyme capable of activating a prodrug. The gene may be transcriptionally regulated by tissue specific promoter or enhancer sequences. The viral vector enters tumour cells and expresses the enzyme, in order that a prodrug is converted to an active drug within the tumour cells (Huber et al., *Proc. Natl. Acad. Sci.* USA (1991) 88, 8039). Alternatively, non-viral methods for the delivery of genes have been used. Such methods include calcium phosphate co-precipitation, microinjection, liposomes, direct DNA uptake, and receptor-mediated DNA transfer. These are reviewed in Morgan & French, *Annu. Rev. Biochem.*, 1993, 62; 191. The term "GDEPT" (gene-directed enzyme prodrug therapy) is used to include both viral and non-viral delivery systems (Denny et al U.S. Pat. No. 6,310,237).

4-Nitroaromatic compounds are reduced by both mammalian and bacterial flavoprotein enzymes, which effect stepwise addition of up to six electrons. The major enzymatic metabolite is usually the 4-electron reduced species (hydroxylamine).

A number of nitrophenyl mustards and nitrophenylaziridines have been reported as prodrugs for use in gene-directed enzyme-prodrug therapy (GDEPT) in conjunction with nitroreductase enzymes. In particular, CB 1954 [5-(aziridin-1-yl)-2,4-dinitrobenzamide; (1) [shown below] is reported to be a substrate for the aerobic nitroreductase NTR (nfsB gene product) isolated from *E. coli* B (Boland et al., Biochem. Pharmacol. 1991, 41, 867-875; Anlezark et al., Biochem. Pharmacol, 1992, 44, 2289-2295; Parkinson et al., J. Med. Chem. 2000, 43, 3624). This compound has been used as a prodrug in both ADEPT (Knox et al., Biochem. Pharmacol., 1995, 49, 1641-1647) and GDEPT (Bridgewater et al.,. Eur. J. Cancer, 1995, 31A, 2362-2370; Bailey et al., Gene Ther., 1996, 3, 1143-1150; Bailey and Hart, Gene Ther., 1997, 4, 80-81; Green et al., Cancer Gene Ther., 1997,4, 229-238) applications, including a clinical trial (Chung-Faye et al., Clin. Cancer Res., 2001, 7, 2662-2668).

Similarly, the dinitrophenyl mustard SN 23862 (2) is also a substrate for NTR, and shows selective toxicity towards cell lines that express the enzyme. It is activated by nitro group reduction (Palmer et al., J. Med. Chem., 1995, 38, 1229; Kestell et al., Cancer Chemother. Pharmacol., 2000, 46, 365-374). The 4-SO$_2$Me derivative (3) was also a substrate (Atwell et al., Anti-Cancer Drug Des., 1996, 11, 553), as were the regioisomers (4) and (5) (Friedlos et al., J. Med. Chem., 1997, 40, 1270).

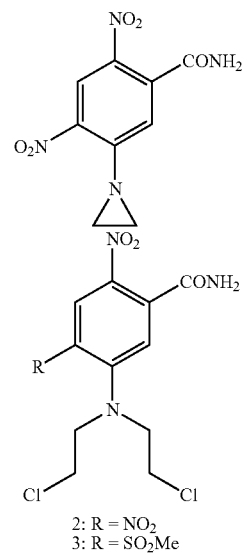

2: R = NO$_2$
3: R = SO$_2$Me

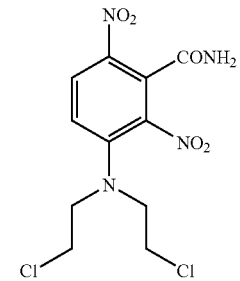

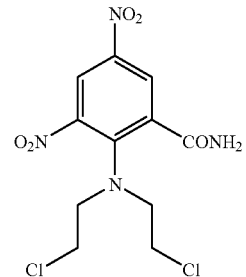

However, compounds of this type were not very effective as bioreductive prodrugs when these compounds were activated in hypoxic tumour tissue by endogenous reductase enzymes, showing potency ratios of 2-5 fold under hypoxic conditions relative to oxic conditions in the wild-type AA8 cell line, using a clonogenic assay (Palmer et al., J. Med. Chem. 1996, 39, 2518-2528).

Some phosphate analogues of mustards have been described, for the purpose of solubilising the compounds. The best known is estramustine phosphate (Estracyt; 6), which has been shown to bind to tubulin binding domains on various microtubule-associated proteins (Moraga et al., Biochim. Biophys. Acta, 1992, 1121, 97-103), and which has been shown to be active in advanced breast cancer (Keren-Rosenberg et al., Semin. Oncol., 1997, 24 (Suppl. 3), 26-29), but has not been shown to be activated by NTR or hypoxia. Another study has also shown estramustine phosphate to be a radiation sensitizer (Kim et al., Int. J. Radiat. Oncol. Biol. Phys., 1994, 29, 555-557). The phenol mustard phosphate analogue 7 is a carboxypeptidase substrate that is not activated under hypoxic conditions, (Matsui et al., Japanese Patent 07082280 A2, 1995), and the solubilised mustard 8 has been described as a phosphatase inhibitor but has not been shown to be activated under hypoxic conditions (Workman, Chem.-Biol. Interact., 1978, 20, 103-112).

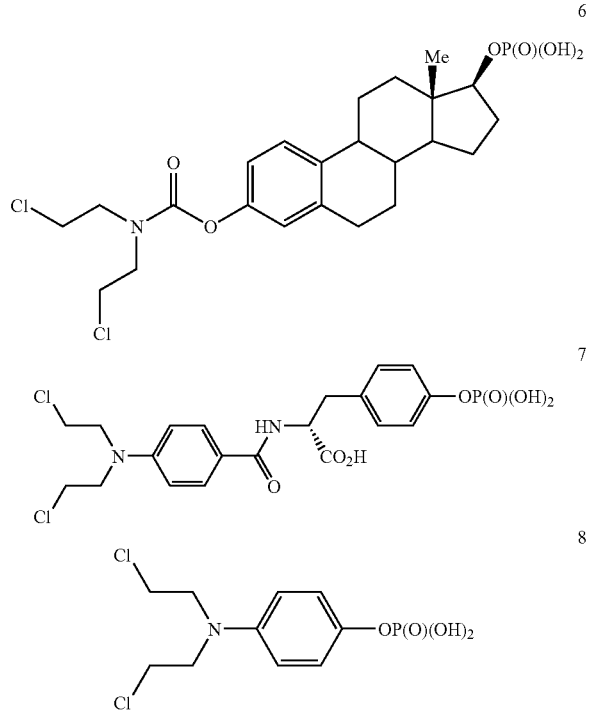

It is an object of the present invention to provide a specific class of nitrophenyl mustards and aziridines, bearing short-chain alcohols, and their corresponding phosphates for use as targeted cytotoxic agents or bioreductive prodrugs or to at least provide the public with a useful alternative.

SUMMARY AND DETAILED DESCRIPTION

In a first aspect, the present invention provides novel phosphate compounds of Formula I

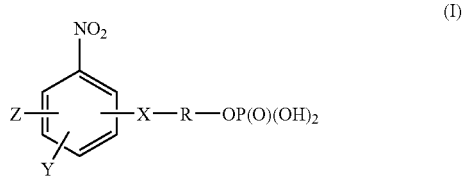

wherein:

X represents at any available ring position —CONH—, —SO$_2$NH—, —O—, —CH$_2$—, —NHCO— or —NHSO$_2$—;

R represents a lower C$_{1-6}$ alkyl optionally substituted with one or more groups including hydroxy, amino and N-oxides therefrom or dialkylamino and N-oxides therefrom;

Y represents at any available ring position —N-aziridinyl, —N(CH$_2$CH$_2$W)$_2$ or —N(CH$_2$CHMeW)$_2$, where each W is independently selected from halogen or —OSO$_2$Me.

Z represents at any available ring position —NO$_2$, -halogen, —CN, —CF$_3$ or —SO$_2$Me; and pharmaceutically acceptable salts and derivatives thereof.

In a preferred embodiment, the phosphate compound of Formula (I) is selected from a compound represented by formulae (Ia), (Ib) or (Ic)

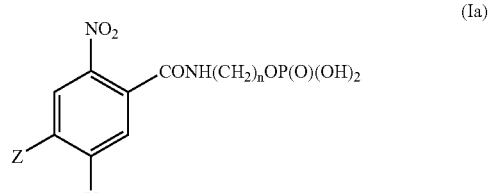

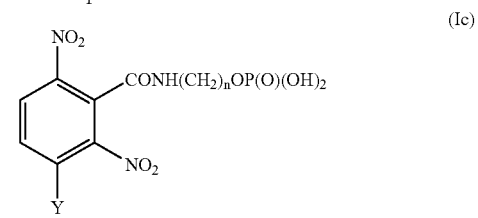

wherein Y may represent

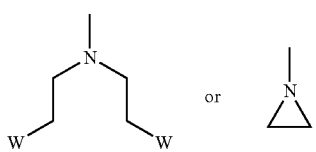

and wherein n represents 1 to 6

Z represents —NO$_2$, -halogen, —CN, —CF$_3$ or —SO$_2$Me; and where each W is independently selected from halogen or —OSO$_2$Me and pharmaceutically acceptable salts and derivatives thereof.

Preferably, the phosphate compound of Formula (I) is selected from the following:

2-[[2-[Bis(2-bromoethyl)amino]-3,5-dinitrobenzoyl]amino] ethyl dihydrogen phosphate;

3-[[5-[Bis(2-chloroethyl)amino]-2,4-dinitrobenzoyl]amino] propyl dihydrogen phosphate;

3-[[5-[Bis(2-bromoethyl)amino]-2,4-dinitrobenzoyl]amino] propyl dihydrogen phosphate;

2-[[2-[Bis(2-chloroethyl)amino]-3,5-dinitrobenzoyl]amino] ethyl dihydrogen phosphate;

2-[(2-Chloroethyl)-2,4-dinitro-6-[[[2-(phosphonooxy)ethyl] amino]-carbonyl]anilino]ethyl methanesulfonate;

2-({2-[Bis(2-bromopropyl)amino]-3,5-dinitrobenzoyl}amino)ethyl dihydrogen phosphate;

2-[(2-Bromoethyl)-2,4-dinitro-6-[[[2-(phosphonooxy)ethyl] amino]-carbonyl]anilino]ethyl methanesulfonate;

2-[[2- [Bis(2-iodoethyl)amino]-3,5-dinitrobenzoyl]amino] ethyl dihydrogen phosphate;

2-[(2-Iodoethyl)-2,4-dinitro-6-({[2-(phosphonooxy)ethyl] amino}carbonyl)-anilino]ethyl methanesulfonate;

2-[(2-Chloroethyl)-2,4-dinitro-3-[[[3-(phosphonooxy)propyl]amino]-carbonyl]anilino]ethyl methanesulfonate;

3-({3-[Bis(2-bromoethyl)amino]-2,6-dinitrobenzoyl}amino)propyl dihydrogen phosphate;

2-[(2-Bromoethyl)-2,4-dinitro-3-[[[2-(phosphonooxy)ethyl] amino]-carbonyl]anilino]ethyl methanesulfonate;

2-[(2-Bromoethyl)-2,4-dinitro-3-[[[3-(phosphonooxy)propyl]amino]-carbonyl]anilino]ethyl methanesulfonate; and 2-[(2-Iodoethyl)-2,4-dinitro-3-[[[3-(phosphonooxy)propyl] amino]-carbonyl]anilino]ethyl methanesulfonate.

In a second aspect, the present invention provides alcohol compounds of Formula (II)

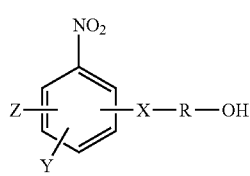

(II)

wherein:

X represents at any available ring position —CONH—, —SO$_2$NH—, —O—, —CH$_2$—, —NHCO— or —NHSO$_2$—;

Y represents at any available ring position —N-aziridinyl, —N(CH$_2$CH$_2$W)$_2$, or —N(CH$_2$CHMeW)$_2$ where each W is independently selected from halogen or —OSO$_2$Me;

Z represents at any available ring position —NO$_2$, -halogen, —CN, —CF$_3$ or —SO$_2$Me;

R represents a lower C$_{1-6}$ alkyl optionally substituted with one or more groups including hydroxy, amino and N-oxides therefrom or dialkylamino and N-oxides therefrom; and pharmaceutically acceptable salts and derivatives thereof, with the proviso that

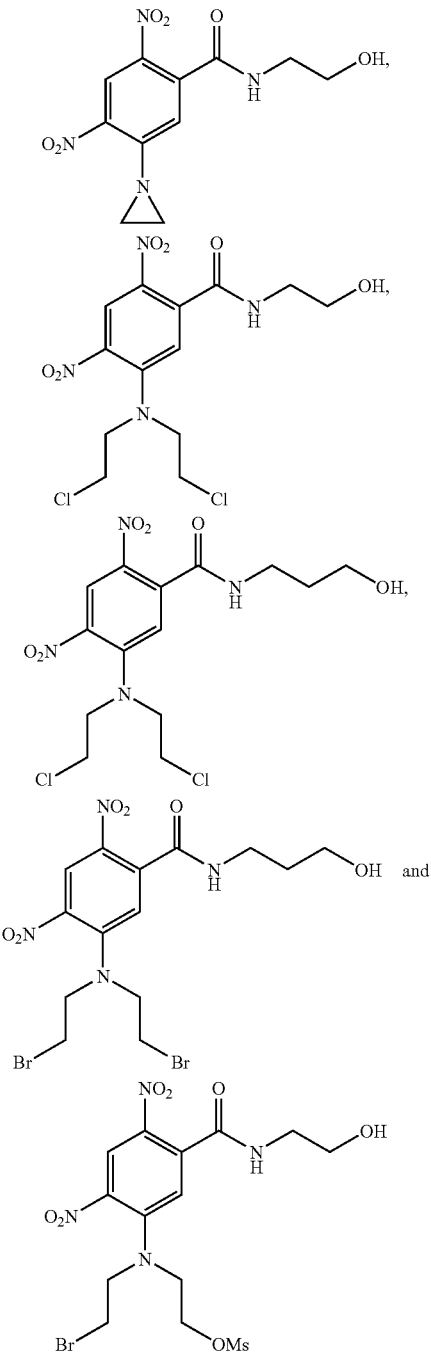

are excluded.

In a preferred embodiment, the alcohol compound of Formula (II) is selected from a compound represented by formulae (IIa), (IIb) or (IIc)

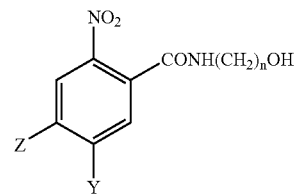
(IIa)

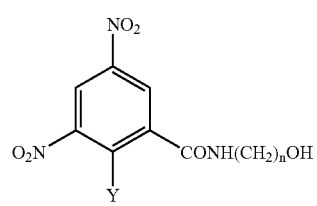
(IIb)

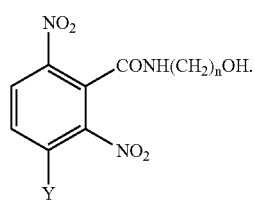
(IIc)

wherein Y may represent

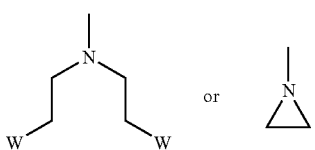

and wherein n represents 1 to 6

Z represents —$NO_2$, -halogen, —CN, —$CF_3$ or —$SO_2Me$; and where each W is independently selected from halogen or —$OSO_2Me$ and pharmaceutically acceptable salts and derivatives thereof with the proviso that

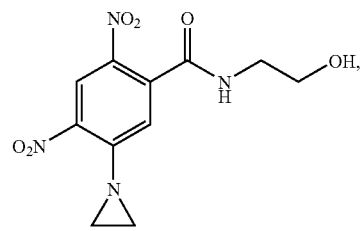

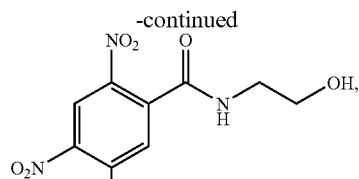

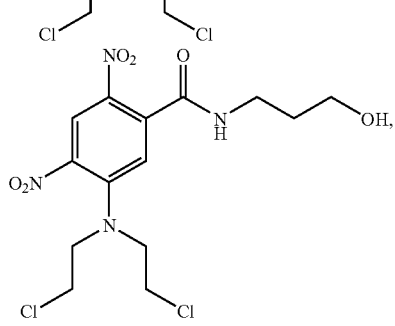

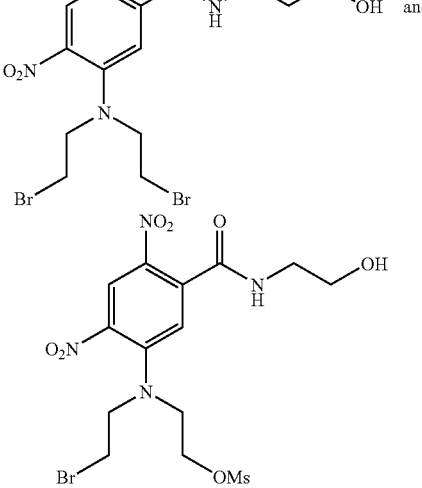

are excluded.

Preferably the compound of Formula (II) is selected from the following:

N-(3-Hydroxypropyl)-5-[bis(2-chloroethyl)amino]-2,4-dinitrobenzamide;

N-(3-Hydroxypropyl)-5-[bis(2-bromoethyl)amino]-2,4-dinitrobenzamide;

N-(2-Hydroxyethyl)-5-[bis(2-bromoethyl)amino]-2,4-dinitrobenzamide;

N-(4-Hydroxybutyl)-5-[bis(2-bromoethyl)amino]-2,4-dinitrobenzamide;

N-(5-Hydroxypentyl)-5-[bis(2-bromoethyl)amino]-2,4-dinitrobenzamide;

N-(6-Hydroxyhexyl)-5-[bis(2-bromoethyl)amino]-2,4-dinitrobenzamide;

5-[Bis(2-bromoethyl)amino]-N-(2-hydroxyethyl)-4-(methylsulfonyl)-2-nitrobenzamide;

2[(2-Bromoethyl)-5-[[(3-hydroxypropyl)amino]carbonyl]-2,4-dinitroanilino]ethyl methanesulfonate;

5-[Bis(2-iodoethyl)amino]-N-(2-hydroxyethyl)-2,4-dinitrobenzamide;

2-[Bis(2-Chloroethyl)amino]-N-(2-hydroxyethyl)-3,5-dinitrobenzamide;

2-[Bis(2-bromoethyl)amino]-N-(2-hydroxyethyl)-3,5-dinitrobenzamide;

2-[Bis(2-chloroethyl)amino]-N-(3-hydroxypropyl)-3,5-dinitrobenzamide;

2-[Bis(2-bromoethyl)amino]-N-(3-hydroxypropyl)-3,5-dinitrobenzamide;

2-[Bis(2-chloroethyl)amino]-N-(4-hydroxybutyl)-3,5-dinitrobenzamide;

2-[Bis(2-bromoethyl)amino]-N-(4-hydroxybutyl)-3,5-dinitrobenzamide;

2-[Bis(2-chloroethyl)amino]-N-(5-hydroxypentyl)-3,5-dinitrobenzamide;

2-[Bis(2-bromoethyl)amino]-N-(5-hydroxypentyl)-3,5-dinitrobenzamide;

2-[Bis(2-chloroethyl)amino]-N-(6-hydroxyhexyl)-3,5-dinitrobenzamide;

2-[Bis(2-bromoethyl)amino]-N-(6-hydroxyhexyl)-3,5-dinitrobenzamide;

2-[Bis(2-bromopropyl)amino]-N-(2-hydroxyethyl)-3,5-dinitrobenzamide;

2-((2-Bromoethyl)-2-{[(2-hydroxypropyl)amino]carbonyl}-4,6-dinitroanilino)ethyl methanesulfonate;

2-((2-Bromoethyl)-2-{[(2-hydroxyethyl)amino]carbonyl}-4,6-dinitroanilino)ethyl methanesulfonate;

2-((2-Chloroethyl)-2-{[(2-hydroxyethyl)amino]carbonyl}-4,6-dinitroanilino)ethyl methanesulfonate;

2-[Bis(2-iodoethyl)amino]-N-(2-hydroxyethyl)-3,5-dinitrobenzamide;

2-((2-Iodoethyl)-2-{[(2-hydroxyethyl)amino]carbonyl}-4,6-dinitroanilino)ethyl methanesulfonate;

3-[Bis(2-bromoethyl)amino]-N-(2-hydroxyethyl)-2,6-dinitrobenzamide;

2-((2-Bromoethyl)-3-{[(2-hydroxyethyl)amino]carbonyl}-2,4-dinitroanilino)ethyl methanesulfonate;

3-[Bis(2-bromoethyl)amino]-N-(3-hydroxypropyl)-2,6-dinitrobenzamide;

2-((2-bromoethyl)-3-{[(3-hydroxypropyl)amino]carbonyl}-2,4-dinitroanilino)ethyl methanesulfonate;

3-[Bis(2-bromoethyl)amino]-N-(4-hydroxybutyl)-2,6-dinitrobenzamide;

2-((2-Bromoethyl)-3-{[(4-hydroxybutyl)amino]carbonyl}-2,4-dinitroanilino)ethyl methanesulfonate;

2-((2-Chloroethyl)-3-{[(3-hydroxypropyl)amino]carbonyl}-2,4-dinitroanilino)ethyl methanesulfonate; and 2-((2-Iodoethyl)-3-{[(3-hydroxypropyl)amino]carbonyl}-2,4-dinitroanilino)ethyl methanesulfonate.

In a third aspect of the invention there is provided a method of preparing the phosphates is represented by the general formula (I);

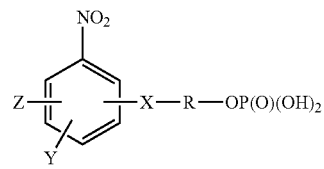

(I)

wherein:

X represents at any available ring position —CONH—, —SO$_2$NH—, —O—, —CH$_2$—, —NHCO— or —NHSO$_2$—;

R represents a lower C$_{1-6}$ alkyl optionally substituted with one or more groups including hydroxy, amino and N-oxides therefrom or dialkylamino and N-oxides therefrom;

Y represents at any available ring position -N-aziridinyl or —N(CH$_2$CH$_2$W)$_2$, where each W is independently selected from halogen or —OSO$_2$Me;

Z represents at any available ring position —NO$_2$, -halogen, —CN, —CF$_3$ or —SO$_2$Me;

and pharmaceutically acceptable salts and derivatives thereof; the method including the step of (i) phosphorylating a compound of formula (II)

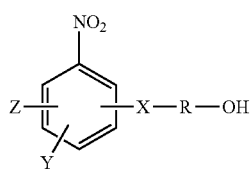

(II)

wherein:

X represents at any available ring position —CONH—, —SO$_2$NH—, —O—, —CH$_2$—, —NHCO— or —NHSO$_2$—;

Y represents at any available ring position —N-aziridinyl, —N(CH$_2$CH$_2$W)$_2$, or —N(CH$_2$CH MeW)$_2$ where each W is independently selected from halogen or —OSO$_2$Me;

Z represents at any available ring position —NO$_2$, -halogen, —CN, —CF$_3$ or —SO$_2$Me; and R represents a lower C$_{1-6}$ alkyl optionally substituted with one or more groups including hydroxy, amino and N-oxides therefrom or dialkylamino and N-oxides therefrom.

In a fourth aspect there is provided a method of preparing a compound of formulae (IIa), (IIb) or (IIc)

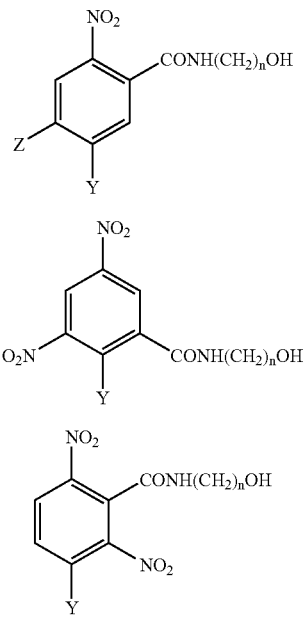

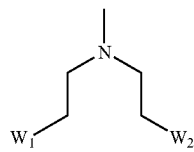

and wherein n represents 1 to 6

Z represents —NO$_2$, -halogen, —CN, —CF$_3$ or —SO$_2$Me; and where W$_1$ is halogen and W$_2$ is —OSO$_2$Me and pharmaceutically acceptable salts and derivatives thereof;

the method including the step of reacting a compound of formulae (IIa'), (IIb') or (IIc') optionally with heating

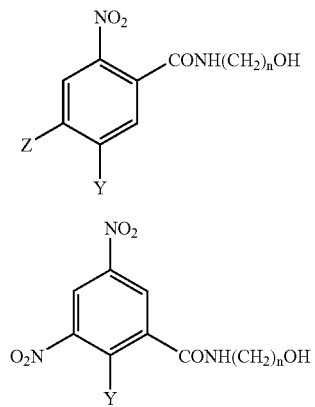

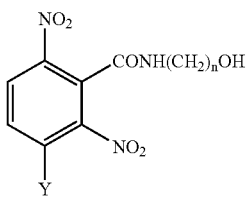

wherein Y may represent

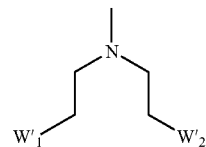

wherein W'$_1$ and W'$_2$ are each halogen;

with an effective amount of silver methanesulfonate (AgOMs) in a solvent to give a compound of formulae (IIa), (IIb) or (IIc) defined above.

It is to be appreciated that in the method defined immediately above where W'$_1$ and W'$_2$ are either iodine and/or bromine that the iodine and/or bromine can be partially or completely substituted with —OSO$_2$Me. In the situation where either or both of W'$_1$ and W'$_2$ represent chlorine, the chlorine is inert and cannot be can be substituted with —OSO$_2$Me.

Preferably the solvent is selected from MeCN or other polar non-protic solvent.

In a fifth aspect there is provided a method of preparing a compound of formulae (Ia), (Ib) or (Ic)

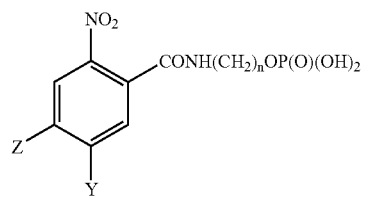

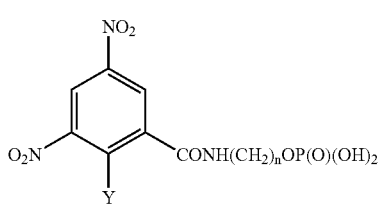

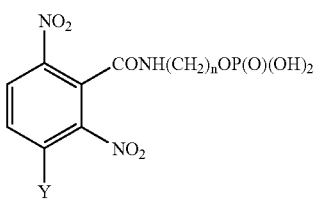

wherein Y may represent

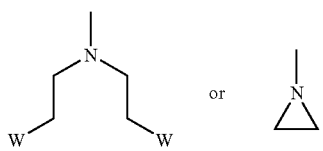

and wherein n represents 1 to 6

Z represents —NO$_2$, -halogen, —CN, —CF$_3$ or —SO$_2$Me; and where each W is independently selected from halogen or —OSO$_2$Me and pharmaceutically acceptable salts and derivatives thereof the method including the step of phosphorylating a compound represented by formulae (IIa), (IIb) or (IIc)

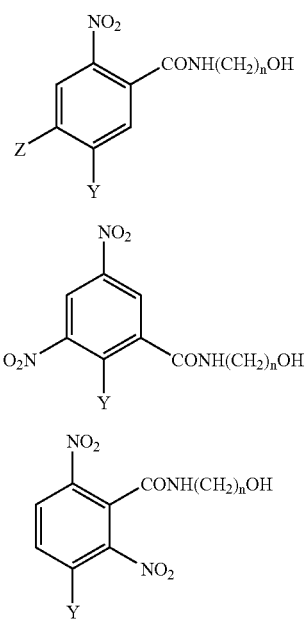

wherein Y represents

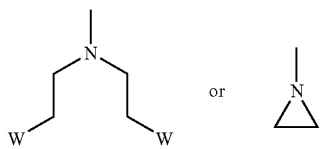

and wherein n represents 1 to 6

Z represents —NO$_2$, -halogen, —CN, —CF$_3$ or —SO$_2$Me; and where each W is independently selected from halogen or —OSO$_2$Me and pharmaceutically acceptable salts and derivatives.

In a sixth aspect there is provided a compound of formula (I), formula (Ia), (Ib) or (Ic) or formula (IIa), (IIb) or (IIc) obtained by any one of the preparative methods defined above.

In a seventh aspect, the present invention provides a method for the use as prodrugs suitable for
(i) GDEPT (gene-directed enzyme-prodrug therapy) or ADEPT (anti-body directed enzyme prodrug therapy) in conjunction with at least one nitroreductase enzyme; or
(ii) Use as one or more hypoxia-selective cytotoxins, including the step of administering a compound of Formula (I) as defined above or a compound of Formula (II)

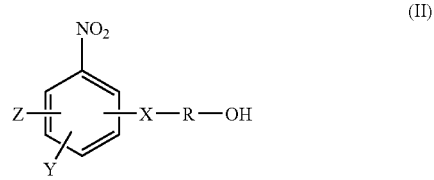

wherein:

X represents at any available ring position —CONH—, —SO$_2$NH—, —O—, —CH$_2$—, —NHCO— or —NHSO$_2$—;

Y represents at any available ring position —N-aziridinyl, —N(CH$_2$CH$_2$W)$_2$, or —N(CH$_2$CH MeW)$_2$ where each W is independently selected from halogen or —OSO$_2$Me;

Z represents at any available ring position —NO$_2$, -halogen, —CN, —CF$_3$ or —SO$_2$Me;

R represents a lower C$_{1-6}$ alkyl optionally substituted with one or more groups including hydroxy, amino and N-oxides therefrom or dialkylamino and N-oxides therefrom; and pharmaceutically acceptable salts and derivatives thereof;

or a mixture thereof in a therapeutically effective amount to tumour cells in a subject.

Preferably, the nitroreductase enzyme is encoded for by the nfsB gene of either *E. coli* or by orthologous genes in *Clostridia* species.

Preferably the method includes the further step of irradiating the tumour cells.

In an eighth aspect, the present invention provides a method for the use as prodrugs suitable for GDEPT (gene-directed enzyme-prodrug therapy) or ADEPT (antibody-directed enzyme prodrug therapy) in conjunction with at least one nitroreductase enzyme, as an anticancer agent including the step of administering a compound of Formula (I) as defined above or a compound of Formula (II)

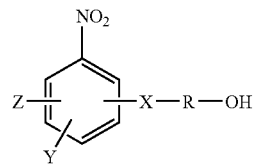

wherein:

X represents at any available ring position —CONH—, —SO$_2$NH—, —O—, —CH$_2$—, —NHCO— or —NHSO$_2$—;

Y represents at any available ring position —N-aziridinyl, —N(CH$_2$CH$_2$W)$_2$ or —N(CH$_2$CH MeW)$_2$, where each W is independently selected from halogen or —OSO$_2$Me;

Z represents at any available ring position —NO$_2$, -halogen, —CN, —CF$_3$ or —SO$_2$Me;

R represents a lower C$_{1-6}$ alkyl optionally substituted with one or more groups including hydroxy, amino and N-oxides therefrom or dialkylamino and N-oxides therefrom; and pharmaceutically acceptable salts and derivatives thereof;

or a mixture thereof in a therapeutically effective amount to target tumour cells in a subject.

Preferably the nitroreductase enzyme is encoded for by the nfsB gene of *E. coli* or by orthologous genes in *Clostridia* species.

Preferably the method includes the further step of irradiating the tumour cells.

It is to be appreciated that with ADEPT it may be necessary to supply a reducing co-factor, because these may not be present in significant concentrations outside cells. It is envisaged that a synthetic co-factor could be used to stimulate activation of the pro-drug by the likes of an intracellular enzyme. The same issue does not arise with GDEPT because there are several intracellular reducing co-factors such as the likes of NADH and NADPH in significant concentrations.

In a ninth aspect of the present invention, there is provided a method of cell ablation utilising at least one nitroreductase enzyme, wherein the method includes the step of administering a compound of Formula (I) as defined a above or a compound of Formula (II)

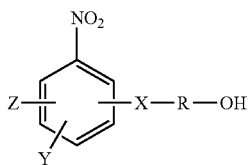

(II)

wherein:

X represents at any available ring position —CONH—, —SO$_2$NH—, —O—, —CH$_2$—, —NHCO— or —NHSO$_2$—;

Y represents at any available ring position —N-aziridinyl, —N(CH$_2$CH$_2$W)$_2$ or —N(CH$_2$CH MeW)$_2$, where each W is independently selected from halogen or —OSO$_2$Me;

Z represents at any available ring position —NO$_2$, -halogen, —CN, —CF$_3$ or —SO$_2$Me;

R represents a lower C$_{1-6}$ alkyl optionally substituted with one or more groups including hydroxy, amino and N-oxides therefrom or dialkylamino and N-oxides therefrom; and pharmaceutically acceptable salts and derivatives thereof, or a mixture thereof in an effective amount to ablate cells, wherein said cells express at least one nitroreductase enzyme.

Preferably the nitroreductase enzyme is encoded for by the nfsB gene in *E. coli* or by orthologous genes in *Clostridia* species.

Preferably, the cells that are targeted for ablation are tumor cells in tissue in a subject.

Preferably, the method of cell ablation utilising at least one nitroreductase enzyme is delivered by either ADEPT or GDEPT technology.

Preferably, the cell ablation provides a substantially minimal bystander effect.

In a tenth aspect, the present invention provides a method of providing anticancer therapy, wherein a compound of Formula (I) as defined above is administered in a therapeutically effective amount to tumour cells in a subject.

Preferably the therapeutically effective amount of said method is between about 20% to 100% of the maximum tolerated dose of said subject.

Preferably, the method includes the further step of irradiating the tumour cells.

In an eleventh aspect of the present invention there is provided a pharmaceutical composition including a therapeutically effective amount of a compound of Formula (I) or a compound of Formula (II)

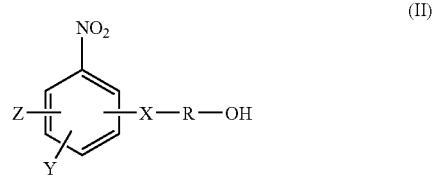

(II)

wherein:

X represents at any available ring position —CONH—, —SO$_2$NH—, —O—, —CH$_2$—, —NHCO— or —NHSO$_2$—;

Y represents at any available ring position —N-aziridinyl, —N(CH$_2$CH$_2$W)$_2$ or —N(CH$_2$CH MeW)$_2$, where each W is independently selected from halogen or —OSO$_2$Me;

Z represents at any available ring position —NO$_2$, -halogen, —CN, —CF$_3$ or —SO$_2$Me;

R represents a lower C$_{1-6}$ alkyl optionally substituted with one or more groups including hydroxy, amino and N-oxides therefrom or dialkylamino and N-oxides therefrom; and pharmaceutically acceptable salts and derivatives thereof, or a mixture thereof, and a pharmaceutically acceptable excipient, adjuvant, carrier, buffer or stabiliser.

The pharmaceutically acceptable excipient, adjuvant, carrier, buffer or stabiliser should preferably be non-toxic and should not interfere with the efficacy of the active ingredient. The precise nature of the carrier or other material will depend on the route of administration, which may be oral, or by injection, such as cutaneous, subcutaneous, or intravenous. It is to be appreciated that these factors could be readily determined by someone skilled in the art without undue experimentation.

Pharmaceutical compositions for oral administration may be in tablet, capsule, powder or liquid form. A tablet may comprise a solid carrier or an adjuvent. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such as gelatin.

For intravenous, cutaneous or subcutaneous injection, the active ingredient will be in the form of a parenterally acceptable aqueous solution which is pyrogen-free and has a suitable pH, isotonicity and stability. Those of relevent skill in the art are well able to prepare suitable solutions using, for example, isotonic vehicles such as Sodium Chloride injection, Ringer's injection, Lactated Ringer's injection. Preservatives, stabilisers, buffers antioxidants and/or other additives may be included as required.

In a twelfth aspect of the present invention there is provided, the use in the manufacture of a medicament of an effective amount of a compound of Formula (I) as defined above or a compound of Formula (II)

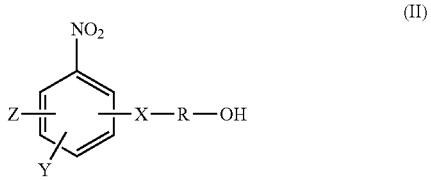

wherein:

X represents at any available ring position —CONH—, —SO$_2$NH—, —O—, —CH$_2$—, —NHCO— or —NHSO$_2$—;

Y represents at any available ring position —N-aziridinyl, —N(CH$_2$CH$_2$W)$_2$ or —N(CH$_2$CH MeW)$_2$, where each W is independently selected from halogen or —OSO$_2$Me;

Z represents at any available ring position —NO$_2$, -halogen, —CN, —CF$_3$ or —SO$_2$Me;

R represents a lower C$_1$- alkyl optionally substituted with one or more groups including hydroxy, amino and N-oxides therefrom or dialkylamino and N-oxides therefrom; and pharmaceutically acceptable salts and derivatives thereof, or mixtures thereof, for use in (i) GDEPT or (ii) as a hypoxia selective cytotoxin, to target cancer cells in a subject in need thereof.

In a thirteenth aspect of the present invention there is provided, the use in the manufacture of a medicament of an effective amount of a compound of Formula (I) as defined above or a compound of Formula (II)

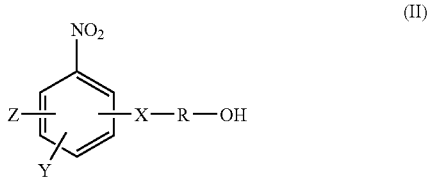

wherein:

X represents at any available ring position —CONH—, —SO$_2$NH—, —O—, —CH$_2$—, —NHCO— or —NHSO$_2$—;

Y represents at any available ring position —N-aziridinyl, —N(CH$_2$CH$_2$W)$_2$ or —N(CH$_2$CH MeW)$_2$, where each W is independently selected from halogen or —OSO$_2$Me;

Z represents at any available ring position —NO$_2$, -halogen, —CN, —CF$_3$ or —SO$_2$Me;

R represents a lower C$_{1-6}$ alkyl optionally substituted with one or more groups including hydroxy, amino and N-oxides therefrom or dialkylamino and N-oxides therefrom; and pharmaceutically acceptable salts and derivatives thereof, or mixtures thereof for use in cell ablation therapy to target cancer cells in a subject in need thereof.

While the compounds of the present invention will typically be used to target tumour cells or tumour tissues in human subjects, they may be used to target tumour cells or tissues in other warm blooded animal subjects such as other primates, farm animals such as cattle, and sports animals and pets such as horses, dogs, and cats.

As used throughout the specification the term "therapeutically effective amount", is to be understood as an amount of a compound of Formula (I) or Formula (II) as defined above or a compound of any one of compounds Ia-Ic, or IIa-IIc as defined above or a mixture thereof that is sufficient to show benefit to a subject with cancer cells. The actual amount, rate and time-course of administration, will depend on the nature and severity of the disease being treated. Prescription of treatment is within the responsibility of general practitioners and other medical doctors.

As used throughout the specification the term "halogen" includes chlorine, bromine or iodine.

It is to be understood that the compounds of the invention as defined above may be administered alone or in combination with other treatments, especially radiotherapy and cytotoxic chemotherapeutic drugs, either simultaneously or sequentially dependent upon the condition to be treated.

As used throughout the specification the pharmaceutically acceptable derivatives and salts thereof include acid derived salts formed from are hydrochloric, sulfuric, phosphoric, acetic, citric, oxalic, malonic, salicylic, malic, fumaric, succinic, ascorbic, maleic, methanesulfonic, isethionic acids and the like and base derived salts formed from sodium and potassium carbonate, sodium and potassium hydroxide, ammonia, triethylamine, triethanolamine and the like.

As used throughout the specification, the term cell ablation is to be understood as the killing of cells, that have been engineered to express an enzyme, such as a nitroreductase, by administration of a prodrug that is activated by that enzyme. As a result, cell ablation can be used to selectively ablate specified target cells or tissue through specific enzymatic expression of a nitroreductase for example, that is specifically expressed by the tissue and which can then be employed to activate a prodrug into an active metabolite to ablate the specified target cells or tissue. (Gusterson et al. *Endocrine Related Cancer*, 1997, 4, 67-74.)

The expression "substantially minimal bystander effect" is to be understood as meaning that the killing of adjoining non-targeted cells is minimal because there is little or no diffusion between the targeted and non-targeted cells of an activated metabolite that arises from the enzymatic activation of a compound of Formula (I) or Formula (II) as defined above or a compound of any one of compounds Ia-Ic, or IIa-IIc as defined above or a mixture thereof.

Pharmaceutically acceptable salts of formula (I) include the basic or acidic compounds of formula (I) that form pharmaceutically acceptable salts with both organic and inorganic acids and/or organic and inorganic bases. Examples of suitable acids for salt formation are hydrochloric, sulfuric, phosphoric, acetic, citric, oxalic, malonic, salicylic, malic, fumaric, succinic, ascorbic, maleic, methanesulfonic, isethionic, and the like. Examples of suitable bases for salt formation are sodium and potassium carbonate, sodium and potassium hydroxide, ammonia, triethylamine, triethanolamine, and the like.

Further aspects of the present invention will become apparent from the following description given by way of example only and with reference to the accompanying synthetic schemes.

Examples of the compounds of Formula (I) where X is —CONH— can be prepared by the processes described in Scheme 1, where Z is as defined above for Formula (I).

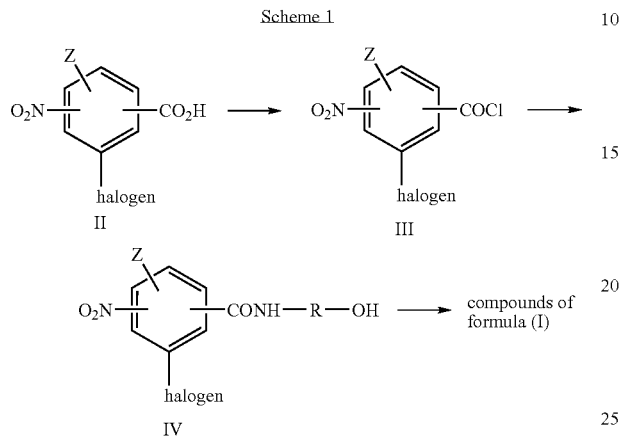

Scheme 1

The following Tables 1a and 2a set out physical data for compounds within the general Formula (I) and (II), representative of it, and capable of being prepared by the processes of the invention.

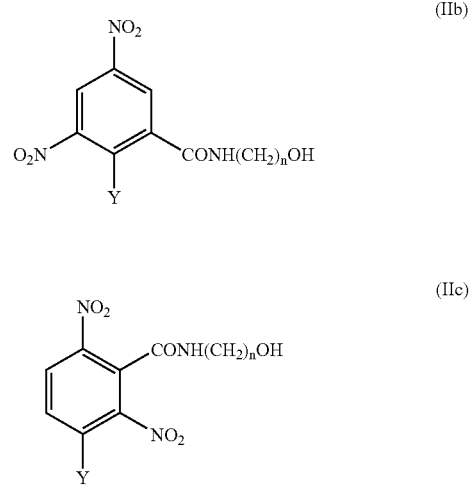

wherein Y may represent

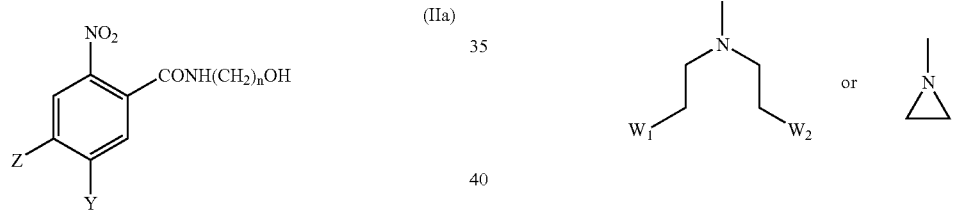

Table 1a. Representative examples of parent alcohols

TABLE 1a

Representative examples of parent alcohols

| No | Z | Y | Y ($W_1$, $W_2$) | n | mp | formula or ref | analyses |
|---|---|---|---|---|---|---|---|
| IIa-1 | $NO_2$ | aziridines | — | 2 | 192–193 | Ref. 1 | C, H, N |
| IIa-2 | $NO_2$ | — | Cl, Cl | 2 | | Ref. 2 | |
| IIa-3 | $NO_2$ | — | Cl, Cl | 3 | 90–91 | Ref 4 | C, H, N, Cl |
| IIa-7 | $NO_2$ | — | Br, Br | 2 | 151–152 | $C_{13}H_{16}Br_2N_4O_6$ | C, H, N, Br |
| IIa-7s | $SO_2Me$ | — | Br, Br | 2 | 126–127 | $C_{14}H_{19}Br_2N_3O_6S$ | C, H, N |
| IIa-8 | $NO_2$ | — | Br, Br | 3 | 85–86 | Ref 4 | C, H, N, Br |
| IIa-9 | $NO_2$ | — | Br, Br | 4 | 123–124 | $C_{15}H_{20}Br_2N_4O_6$ | C, H, N, Br |
| IIa-10 | $NO_2$ | — | Br, Br | 5 | gum | $C_{16}H_{22}Br_2N_4O_6$ | HRMS |
| IIa-11 | $NO_2$ | — | Br, Br | 6 | gum | $C_{17}H_{24}Br_2N_4O_6$ | HRMS |
| IIa-12 | $NO_2$ | — | Br, OMs | 2 | | Ref. 2 | |
| IIa-13 | $NO_2$ | — | Br, OMs | 3 | gum | $C_{16}H_{21}BrN_4O_9S$ | HRMS |
| IIa 14 | $NO_2$ | — | I, I | 2 | 142–143 | $C_{13}H_{16}I_2N_4O_6$ | C, H, N, I |
| IIb-1 | — | aziridines | — | 6 | 189–192 | $C_{15}H_{20}N_4O_6$ | C, H, N |
| IIb-2 | — | — | Cl, Cl | 2 | 109–111 | $C_{13}H_{16}Cl_2N_4O_6$ | C, H, N |
| IIb-3 | — | — | Cl, Cl | 3 | 89–91 | $C_{14}H_{18}Cl_2N_4O_6$ | C, H, N, Cl |
| IIb-4 | — | — | Cl, Cl | 4 | gum | $C_{15}H_{20}Cl_2N_4O_6$ | HRMS |
| IIb-5 | — | — | Cl, Cl | 5 | gum | $C_{16}H_{22}Cl_2N_4O_6$ | HRMS |
| IIb-6 | — | — | Cl, Cl | 6 | gum | $C_{17}H_{24}Cl_2N_4O_6$ | HRMS |
| IIb-2m | — | — | Cl, OMs | 2 | gum | $C_{14}H_9ClN_4O_9S$ | HRMS |
| IIb-7 | — | — | Br, Br | 2 | 105–108 | $C_{13}H_{16}Br_2N_4O_6$ | C, H, N, Br |
| IIb-7a | — | — | Br, Br[4] | 2 | 127–130 | $C_{15}H_{20}Br_2N_4O_6$ | C, H, N |

TABLE 1a-continued

Representative examples of parent alcohols

| No | Z | Y | Y ($W_1, W_2$) | n | mp | formula or ref | analyses |
|---|---|---|---|---|---|---|---|
| IIb-8 | — | — | Br, Br | 3 | 89–94 | $C_{14}H_{18}Br_2N_4O_6$ | C, H, N, Br |
| IIb-9 | — | — | Br, Br | 4 | gum | $C_{15}H_{20}Br_2N_4O_6$ | HRMS |
| IIb-10 | — | — | Br, Br | 5 | gum | $C_{16}H_{22}Br_2N_4O_6$ | HRMS |
| IIb-11 | — | — | Br, Br | 6 | gum | $C_{17}H_{24}Br_2N_4O_6$ | HRMS |
| IIb-12 | — | — | Br, OMs | 2 | | Ref. 3 | |
| IIb-13 | — | — | Br, OMs | 3 | gum | $C_{15}H_{21}BrN_4O_9S$ | HRMS |
| IIb-14 | — | — | I, I | 2 | 129–131 | $C_{13}H_{16}I_2N_4O_6$ | C, H, N |
| IIb-15 | — | — | I, OMs | 2 | gum | $C_{14}H_{19}IN_4O_9S$ | HRMS |
| IIc-6 | | | Cl, OMs | 3 | 104–109 | $C_{15}H_{21}ClN_4O_9S$ | C, H, N |
| IIc-7 | — | — | Br, Br | 2 | gum | $C_{13}H_{16}Br_2N_4O_6$ | HRMS |
| IIc-8 | — | — | Br, Br | 3 | gum | $C_{14}H_{18}Br_2N_4O_6$ | HRMS |
| IIc-9 | — | — | Br, Br | 4 | gum | $C_{15}H_{20}Br_2N_4O_6$ | HRMS |
| IIc-12 | — | — | Br, OMs | 2 | 94–97 | $C_{14}H_{19}BrN_4O_9S$ | C, H, N |
| IIc-13 | — | — | Br, OMs | 3 | 115–117 | Ref. 3 | C, H, N |
| IIc-14 | — | — | Br, OMs | 4 | 114–117 | $C_{16}H_{23}BrN_4O_9S$ | C, H, N |
| IIc-15 | — | — | I, OMs | 3 | 100–103 | $C_{15}H_{21}IN_4O_9S$ | C, H, N |

[A] α-methyl mustard

Notes

References for known compounds.
1. Khan AH, Ross WCJ. Tumor-growth inhibitory nitrophenylaziridines and related compounds. Structure-activity relations. II. Chem.-Biol. Int., 1971, 4, 11–22.
2. NZ Patent No. 240785
3. Co-pending NZ Application No. 521851
4. Wilson WR, Pullen SM, Hogg A, Helsby NA, Hicks KO, Denny WA. Quantitation of bystander effects in nitroreductase suicide gene therapy using three-dimentional cell cultures. Cancer Res., 2002, 62, 1425–1432.

The compounds of Table 1a can be prepared by the general methods set out in Schemes 2a-2k, and exemplified in Examples 1-20 below.

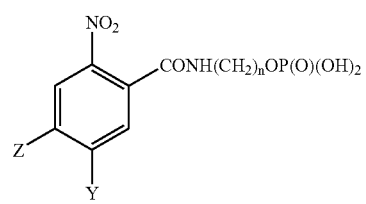

(Ia)

where Y may represent

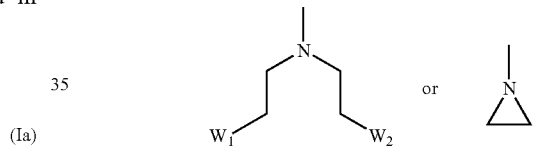

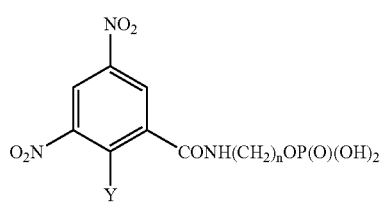

(Ib)

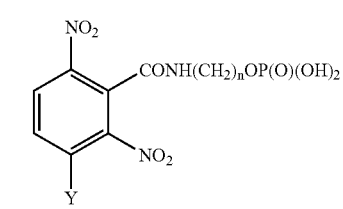

(Ic)

TABLE 1b

Examples of phosphates of formulae Ia–Ic

| No | Z | Y ($W_1, W_2$) | n | mp | formula | analyses |
|---|---|---|---|---|---|---|
| Ia-3P | $NO_2$ | Cl, Cl | 3 | 195–200 | $C_{14}H_{19}Cl_2N_4O_9P$ | HRMS |
| Ia-8P | $NO_2$ | Br, Br | 3 | 170–174 | $C_{14}H_{19}Br_2N_4O_9P$ | HRMS |
| Ib-2P | — | Cl, Cl | 2 | Foam | $C_{13}H_{17}Cl_2N_4O_9P$ | HRMS |
| Ib-2mP | | Cl, OMs | 2 | 132–134 | $C_{14}H_{20}ClN_4O_{12}PS$ | C, H, N |
| Ib-7P | — | Br, Br | 2 | Foam | $C_{13}H_{17}Br_2N_4O_9P$ | HRMS |
| Ib-7aP | — | Br, Br[A] | 2 | 157–161 | $C_{15}H_{21}Br_2N_4O_9P$ | C, H, N |
| Ib-12P | — | Br, OMs | 2 | Foam | $C_{14}H_{20}BrN_4O_{12}PS$ | HRMS |
| Ib-14P | — | I, I | 2 | Foam | $C_{13}H_{17}I_2N_4O_9P$ | HRMS |
| Ib-15P | — | I, OMs | 2 | 147–150 | $C_{14}H_{20}IN_4O_{12}PS$ | C, H, N |
| Ic-6P | | Cl, OMs | 3 | 88–92 | $C_{15}H_{22}ClN_4O_{12}PS$ | C, H, N |
| Ic-8P | — | Br, Br | 3 | Foam | $C_{14}H_{19}Br_2N_4O_9P$ | HRMS |
| Ic-12P | — | Br, OMs | 2 | 93–97 | $C_{14}H_{20}BrN_4O_{12}PS$ | C, H, N |
| Ic-13P | — | Br, OMs | 3 | foam | $C_{15}H_{22}BrN_4O_{12}PS$ | HRMS |
| Ic-15P | | I, OMs | 3 | | $C_{15}H_{22}IN_4O_{12}PS$ | |

[A] alpha-Me

The compounds of Table 1b can be prepared by the general methods set out in Scheme 3, and exemplified in Examples 26-39 below.

Scheme 2a

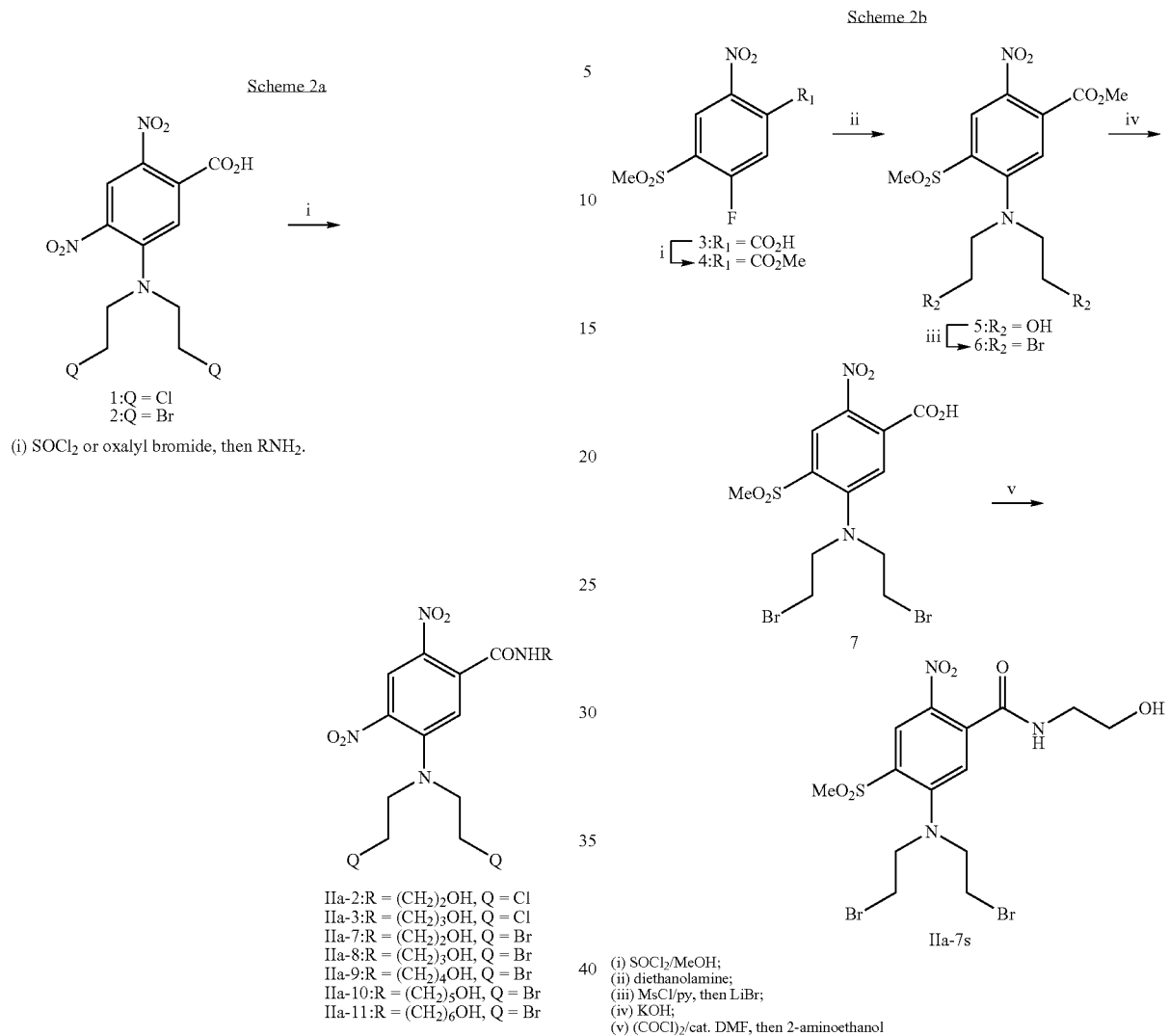

IIa-2: R = (CH₂)₂OH, Q = Cl
IIa-3: R = (CH₂)₃OH, Q = Cl
IIa-7: R = (CH₂)₂OH, Q = Br
IIa-8: R = (CH₂)₃OH, Q = Br
IIa-9: R = (CH₂)₄OH, Q = Br
IIa-10: R = (CH₂)₅OH, Q = Br
IIa-11: R = (CH₂)₆OH, Q = Br (i) SOCl₂/MeOH;
(ii) diethanolamine;
(iii) MsCl/py, then LiBr;
(iv) KOH;
(v) (COCl)₂/cat. DMF, then 2-aminoethanol Scheme 2c

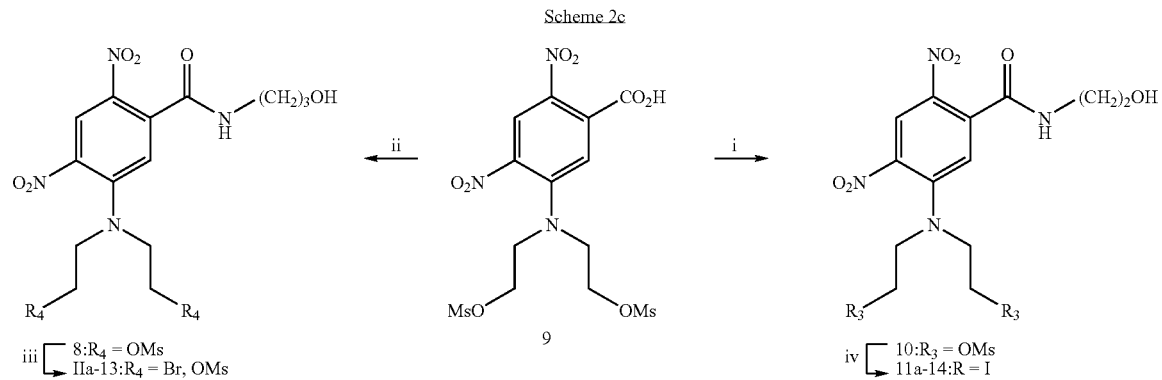

(i) SOCl₂/cat DMF or (COCl)₂/cat DMF, then 2-aminoethanol
(ii) SOCl₂/cat DMF or (COBr)₂/cat DMF, then 3-amino-1-propanol
(iii) LiBr (1.4 equiv.)/DMF;
(iv) NaI (excess)/MeCN.

Scheme 2d

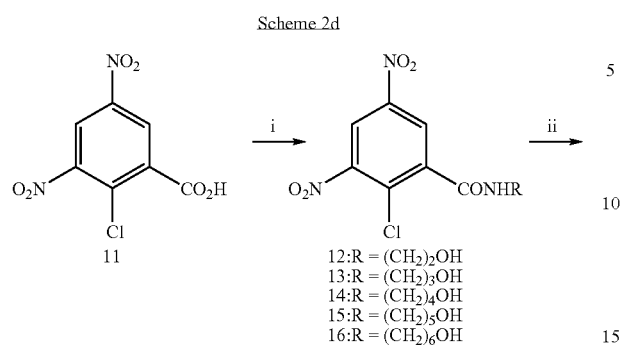

12: R = (CH₂)₂OH
13: R = (CH₂)₃OH
14: R = (CH₂)₄OH
15: R = (CH₂)₅OH
16: R = (CH₂)₆OH

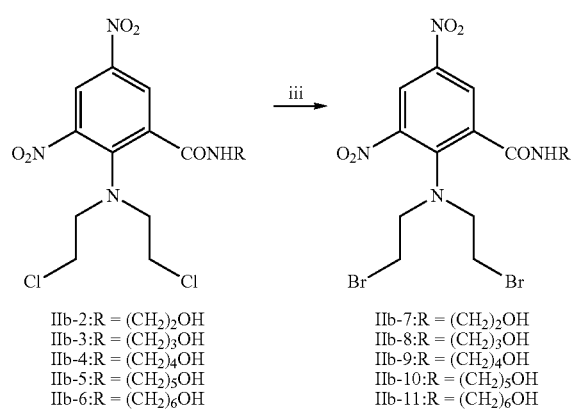

IIb-2: R = (CH₂)₂OH      IIb-7: R = (CH₂)₂OH
IIb-3: R = (CH₂)₃OH      IIb-8: R = (CH₂)₃OH
IIb-4: R = (CH₂)₄OH      IIb-9: R = (CH₂)₄OH
IIb-5: R = (CH₂)₅OH      IIb-10: R = (CH₂)₅OH
IIb-6: R = (CH₂)₆OH      IIb-11: R = (CH₂)₆OH (i) SOCl₂/cat. DMF, then RNH₂;
(ii) HN(CH₂CH₂Cl)₂;
(iii) LiBr/3-Mebutanone Scheme 2e

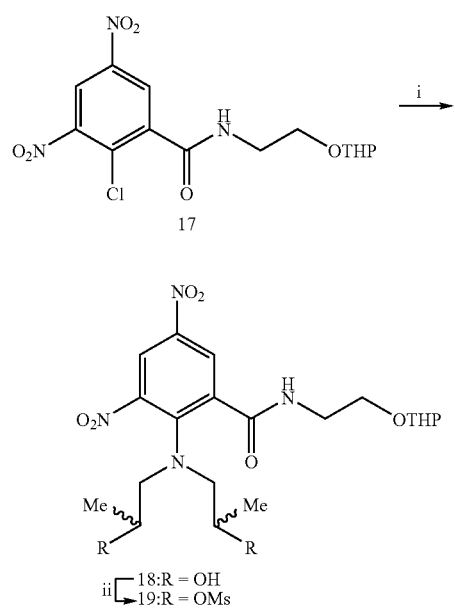

18: R = OH
19: R = OMs

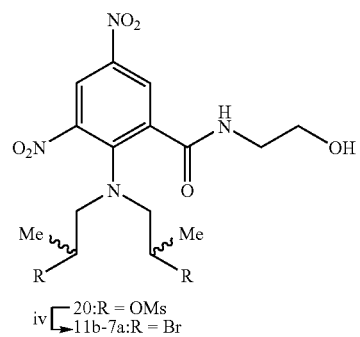

20: R = OMs
IIb-7a: R = Br (i) diisopropanolamine;
(ii) MsCl/Et₃N;
(iii) 1N HCl/THF;
(iv) LiBr (excess).

Scheme 2f

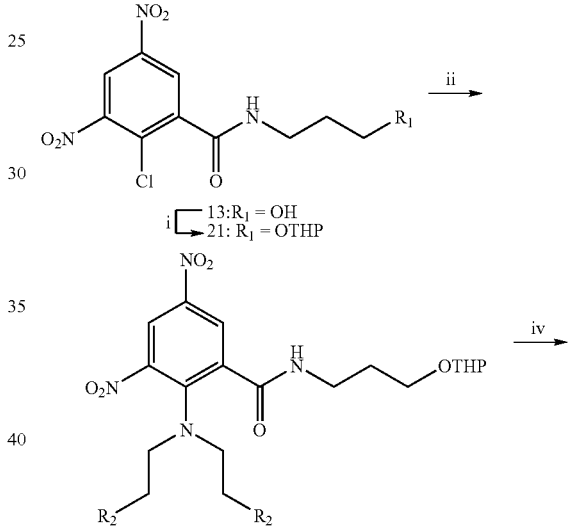

13: R₁ = OH
21: R₁ = OTHP

22: R₂ = OH
23: R₂ = OMs

24: R₂ = OMs
IIb-13: R₂ = OMs, Br (i) 3,4-dihydro-2H-pyran, p-TsOH;
(ii) diethanolamine;
(iii) MsCl/Et₃N;
(iv) 1N HCl/THF;
(v) LiBr (1.2eq).

Scheme 2g
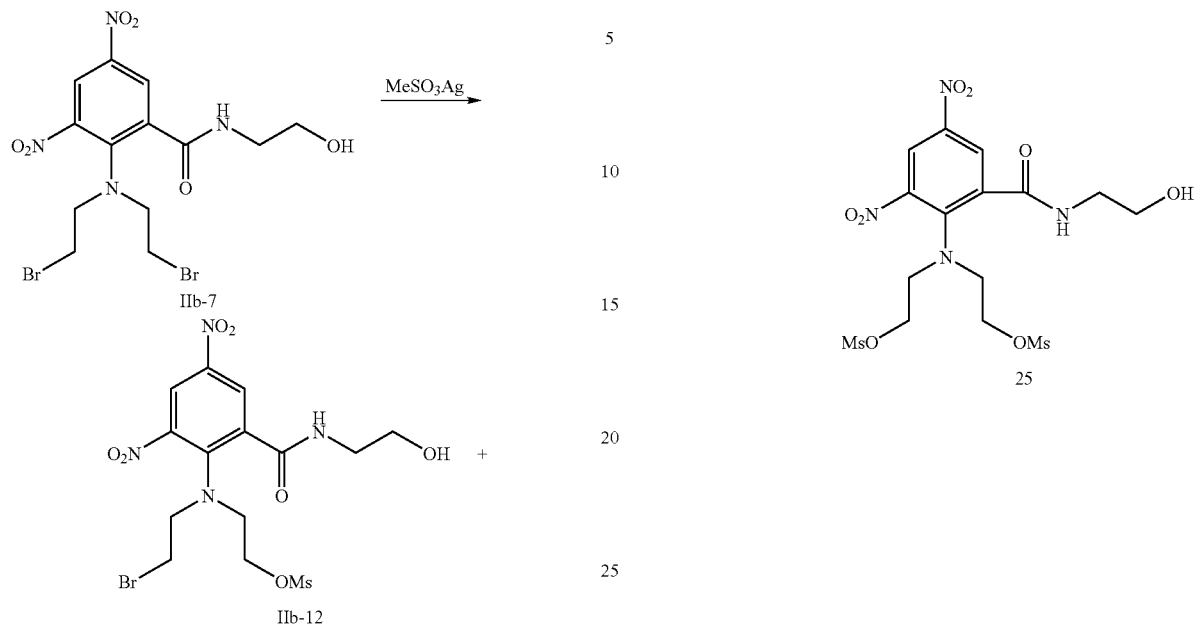
Scheme 2h
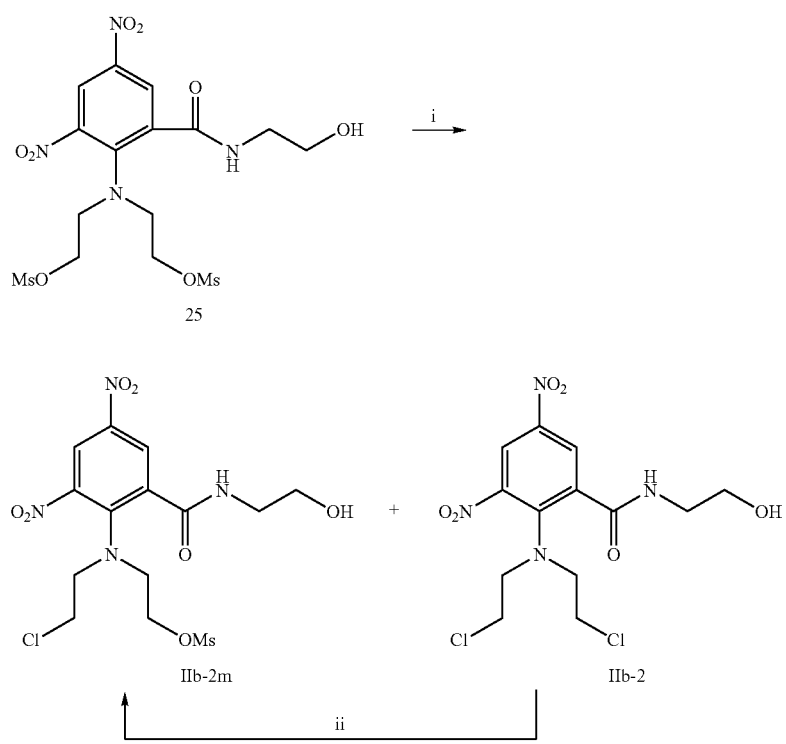
(i) LiCl (1.2 eq)
(ii) NaI or LiBr (1.2 eq) then MeSO$_3$Ag (1.5 eq)

Scheme 2i
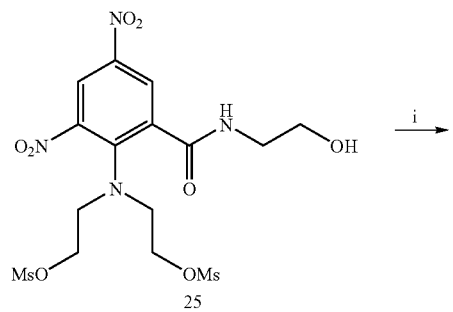
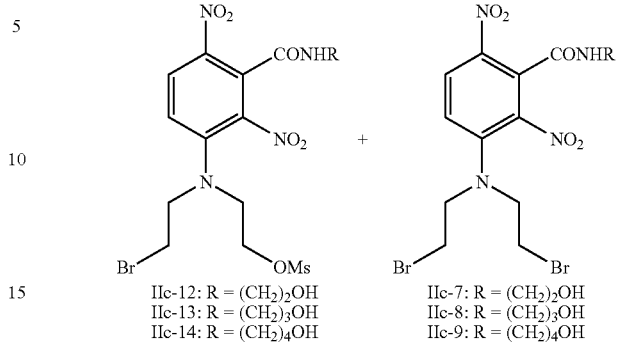
IIc-12: R = (CH$_2$)$_2$OH
IIc-13: R = (CH$_2$)$_3$OH
IIc-14: R = (CH$_2$)$_4$OH
IIc-7: R = (CH$_2$)$_2$OH
IIc-8: R = (CH$_2$)$_3$OH
IIc-9: R = (CH$_2$)$_4$OH
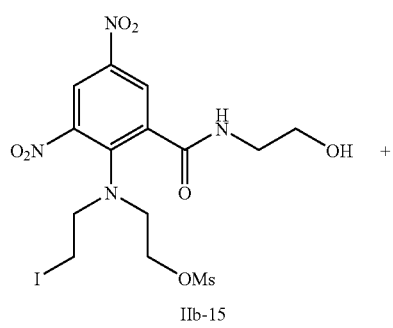
IIb-15
Scheme 2k
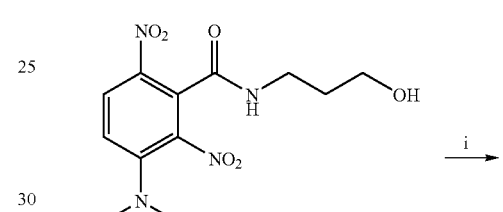
IIc-B
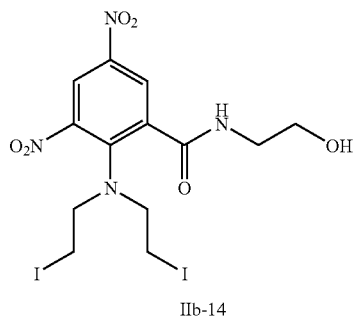
IIb-14
(i) NaI (1.5 eq)
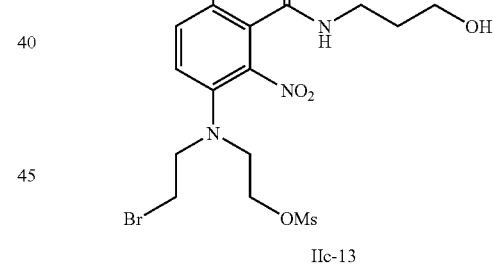
IIc-13
Scheme 2j
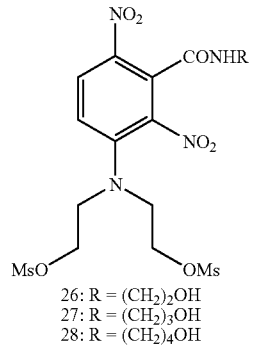
26: R = (CH$_2$)$_2$OH
27: R = (CH$_2$)$_3$OH
28: R = (CH$_2$)$_4$OH
LiBr →
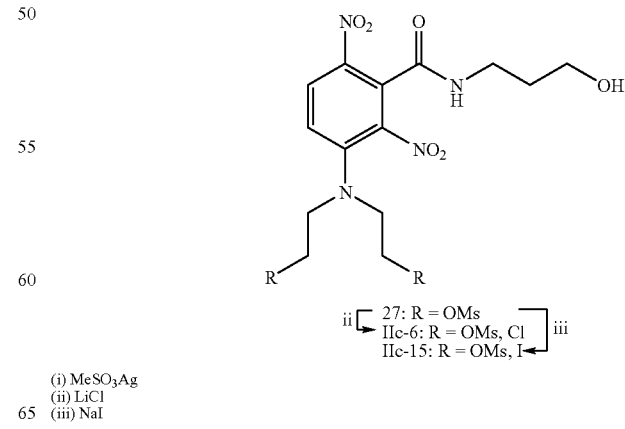
27: R = OMs
IIc-6: R = OMs, Cl
IIc-15: R = OMs, I
(i) MeSO$_3$Ag
(ii) LiCl
(iii) NaI Scheme 3

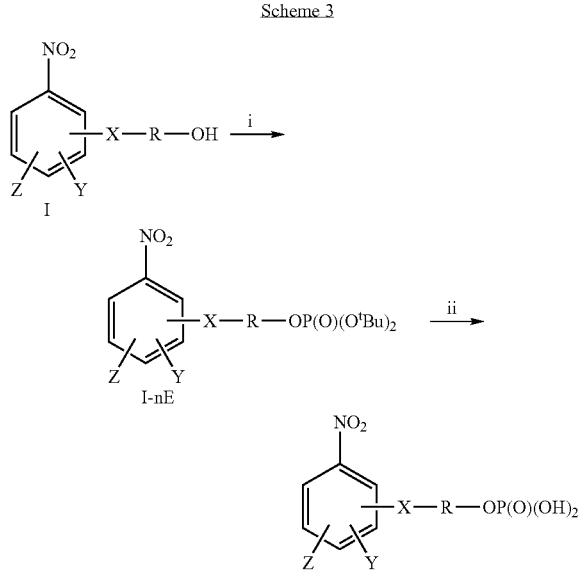

(i) Et$_2$NP(O$^t$Bu)$_2$ or i-Pr$_2$NP(O$^t$Bu)$_2$/1H-tetrazole, then mCPBA or H$_2$O$_2$
(ii) TFA/CH$_2$Cl$_2$ In Scheme 3, X, Y, Z, and R are as specified for formula (I) and (II) above.

EXAMPLES

The invention and the best mode for practising the same are illustrated by the following Examples 1-25 (alcohols) and Examples 26-39 (phosphates).

Example 1

(Scheme 2a)

N-(3-Hydroxypropyl)-5-[bis(2-Chloroethyl)Amino]-2,4-Dinitrobenzamide (IIa-3)

A suspension of 5-[bis(2-chloroethyl)amino]-2,4-dinitrobenzoic acid [Palmer et al., J. Med. Chem., 1994, 37, 2175] (1) (2.50 g, 7.1 mmol) in SOCl$_2$ (20 mL) containing DMF (2 drops) was heated under reflux for1 h, then concentrated to dryness under reduced pressure and re-evaporated with benzene. The resulting crude benzoyl chloride was dissolved in Me$_2$CO (50 mL) and the cooled (−5° C.) solution was treated with a cold solution of 3-amino-1-propanol (1.09 g, 14.5 mmol) in water (25 mL). The reaction mixture was shaken at room temperature for 5 min, then diluted with water (25 mL), concentrated to half volume, and extracted with CH$_2$Cl$_2$ (2×). The organic extract was washed with 0.1 N HCl and water then worked up to give a solid which was chromatographed on silica gel, eluting with EtOAc to give IIa-3 (2.37 g, 82%): mp (EtOAc/i-Pr$_2$O) 90-91° C.; $^1$H [(CD$_3$)$_2$SO] δ8.63 (t, J=5.6 Hz, 1 H, CONH), 8.53 (s, 1 H, H-3), 7.42 (s, 1 H, H-6), 4.46 (t, J=5.1 Hz, 1 H, OH), 3.82 (t, J=5.9 Hz, 4 H, N(CH$_2$CH$_2$Cl)$_2$), 3.68 (t, J=5.9 Hz, 4 H, N(CH$_2$CH$_2$Cl)$_2$), 3.49 (q, J=6.0 Hz, 2 H, CH$_2$OH), 3.29 (q, partially obscured, J=5.9 Hz, 2 H, CONHCH$_2$), 1.68 (pent, J=6.7 Hz, 2 H, CH$_2$CH$_2$CH$_2$). Anal. (C$_{14}$H$_{18}$Cl$_2$N$_4$O$_6$) C, H, N, Cl.

Example 2

(Scheme 2a)

N-(3-Hydroxypropyl)-5-[Bis(2-Bromoethyl)Amino]-2,4-Dinitrobenzamide (IIa-8)

A suspension of powdered 5-[bis(2-bromoethyl)amino]-2,4-dinitrobenzoic acid (2) (1.10 g, 2.49 mmol) in benzene (170 mL) was treated at 20° C. with oxalyl bromide (1.10 mL, 11.7 mmol) and DMF (2 drops). The mixture was stirred at 20° C. for 2 h, then concentrated under reduced pressure, and re-evaporated to dryness in the presence of benzene under high vacuum. The resulting acid bromide was dissolved in Me$_2$CO (20 mL) and the solution was treated at −5° C. with a cold solution of 3-amino-1-propanol (0.39 g, 5.19 mmol) in water (10 mL). The mixture was shaken at room temperature for 5 min, then diluted with water and extracted with EtOAc (2×). The organic extract was worked up and the resulting residue was chromatographed on silica gel, eluting with EtOAc, to give IIa-8 (1.06 g, 85%): mp (EtOAc/i-Pr$_2$O) 85-86° C.; $^1$H NMR [(CD$_3$)$_2$SO] δ 8.64 (t, J=5.6 Hz, 1 H, CONH), 8.53 (s, 1 H, H-3), 7.41 (s, 1 H, H-6), 3.77-3.64 (m, 8 H, N(CH$_2$CH$_2$Cl)$_2$), 4.46 (br s, 1 H, OH), 3.49 (t, J=6.3 Hz, 2 H, CH$_2$OH), 3.33-3.25 (m, partially obscured, 2 H, CONHCH$_2$), 1.68 (pent, J=6.72 Hz, 2 H, CH$_2$CH$_2$CH$_2$). Anal. (C$_{14}$Hl$_{18}$Br$_2$N$_4$O$_6$) C, H, N, Br.

Example 3

(Scheme 2a)

N-(2-Hydroxyethyl)-5-[Bis(2-Bromoethyl)Amino]-2,4-Dinitrobenzamide (IIa-7)

Similar reaction of the acid bromide of 2 with 2-aminoethanol gave IIa-7 (0.78 g, 46%): mp (MeOH/EtOAc/pet. ether) 151-152° C.; $^1$H NMR [(CD$_3$)$_2$SO] δ 8.73 (t, J=5.7 Hz, 1 H, CONH), 8.53 (s, 1 H, H-3), 7.43 (s, 1 H, H-6), 4.76 (t, J=5.6 Hz, 1 H, OH), 3.77-3.64 (m, 8 H, N(CH$_2$CH$_2$Br)$_2$), 3.53 (q, J=6.0 Hz, 2 H, CH$_2$OH), 3.31 (q, partially obscured, J=6.1 Hz, 2 H, CONHCH$_2$). Anal. (C$_{13}$H$_{16}$Br$_2$N$_4$O$_6$) C, H, N, Br.

Example 4

(Scheme 2a)

N-(4-Hydroxybutyl)-5-[Bis(2-Bromoethyl)Amino]-2,4-Dinitrobenzamide (IIa -9)

Similar reaction of the acid bromide of 2 with 4-amino-1-butanol in cold Me$_2$CO, followed by chromatography on silica gel and elution with EtOAc gave IIa-9 (69%) as a yellow solid: mp (EtOAc/iPr$_2$O) 123-124° C.; $^1$H NMR [(CD$_3$)$_2$SO] δ 8.62 (t, J=5.6 Hz, 1 H), 8.53 (s, 1 H), 7.39 (s, 1 H), 4.39 (t, J=5.1 Hz, 1 H), 3.78-3.64 (m, 8 H), 3.47-3.40 (m, 2 H), 3.27-3.20 (m, 2 H), 1,61-1.44 (m, 4 H). Anal. (C$_{15}$H$_{20}$Br$_2$N$_4$O$_6$) C, H, N, Br.

Example 5

(Scheme 2a)

N-(5-Hydroxypentyl)-5-[Bis(2-Bromoethyl)Amino]-2,4-Dinitrobenzamide (IIa-10)

Similar reaction of the acid bromide of 2 with 5-amino-1-pentanol in cold $Me_2CO$, followed by chromatography on silica gel and elution with EtOAc gave IIa-10 (66%) as a yellow foam; $^1H$ $[(CD_3)_2SO]$ δ 8.62 (t, J=5.6 Hz, 1 H), 8.53 (s, 1 H), 7.38 (s, 1 H), 4.34 (t, J=5.1 Hz, 1 H), 3.79-3.64 (m, 8 H), 3.44-3.37 (m, 2 H), 3.26-3.18 (m, 2 H), 1.59-1.29 (m, 4 H). HRMS (FAB) Calcd. for $C_{16}H_{23}{}^{79}Br_2N_4O_6$ $[M+H^+]$ m/z 524.9984, found 524.9964.

Example 6

(Scheme 2a)

N-(6-Hydroxyhexyl)-5-[Bis(2-Bromoethyl)Amino]-2,4-Dinitrobenzamide (IIa-10)

Similar reaction of the acid bromide of 2 with 6-amino-1-hexanol in cold $Me_2CO$, followed by chromatography on silica gel and elution with EtOAc gave IIa-11 (72%) as a yellow foam; $^1H$ NMR $[(CD_3)_2SO]$ δ 8.61 (t, J=5.6 Hz, 1 H), 8.53 (s, 1 H), 7.38 (s, 1 H), 4.31 (t, J=5.2 Hz, 1 H), 3.79-3.64 (m, 8 H), 3.43-3.36 (m, 2 H), 3.27-3.19 (m, 2 H), 1.58-1.26 (m, 4 H). HRMS (FAB) Calcd. for $C_{17}H_{25}{}^{79}Br_2N_4O_6$ $[M+H^+]$ m/z 539.0141, found 539.0137.

Example 7

(Scheme 2b)

5-[Bis(2-Bromoethyl)Amino]-N-(2-hydroxyethyl)-4-(Methylsulfonyl)-2-Nitrobenzamide (IIa-7s)

5-Fluoro-4-(methylsulfonyl)-2-nitrobenzoic acid [Atwell et al., ACDD, 1996, 11, 553] (3) was heated in excess $SOCl_2$/catalytic DMF to provide the acid chloride, which was reacted with dry MeOH to give methyl 5-fluoro-4-(methylsulfonyl)-2-nitrobenzoate (4): mp (EtOAc/hexane) 134-135° C.; $^1H$ NMR $[(CD_3)_2SO]$ δ 8.49 (d, J=5.9 Hz, 1 H), 8.14 (d, J=9.3 Hz, 1 H), 3.92 (s, 3 H), 3.46 (s, 3 H). Anal. ($C_9H_8FNO_6S$) C, H, N.

A mixture of 4 (1.48 g, 5.34 mmol) and diethanolamine (1.40 g, 13.3 mmol) in DMA (6 mL) was stirred at 30° C. for 1 h, and then diluted with EtOAc (60 mL). The solution was washed with brine (2×) and concentrated under reduced pressure. The residue was purified by chromatography on silica gel, eluting with EtOAc/MeOH, followed by recrystallization from EtOAc/$iPr_2O$, to give methyl 5-[bis(2-hydroxyethyl) amino]-4-(methylsulfonyl)-2-nitrobenzoate (5) (1.41 g, 73%): mp 99-100° C.; $^1H$ NMR $[(CD_3)_2SO]$ δ 8.56 (s, 1 H), 7.73 (s, 1 H), 4.62 (t, J=4.9 Hz, 2 H), 3.89 (s, 3 H), 3.59-3.49 (m, 8 H), 3.45 (s, 3 H). Anal. ($C_{13}H_{18}N_2O_8S$) C, H, N.

A solution of 5 (1.48 g, 4.08 mmol) in dry pyridine (15 mL) was treated dropwise at 0° C. with MsCl (0.80 mL, 10.3 mmol). The reaction was stirred at 0° C. for 2 h, then poured into 10% aqueous NaBr. The resulting crude dimesylate was collected, washed well with water, dried, dissolved in DMF (15 mL) and stirred with NaBr (21.6 g, 25 mmol) at 70° C. for 1.5 h. The cooled mixture was poured into water and the resulting solid was purified by chromatography, on silica gel, eluting with $CH_2Cl_2$, then recrystallisation from $CH_2Cl_2$/$iPr_2O$ to give methyl 5-[bis(2-bromoethyl)amino]-4-(methylsulfonyl)-2-nitrobenzoate (6) (1.47 g, 74%): mp 161-162° C.; $^1H$ NMR $[(CD_3)_2SO]$ δ 8.58 (s, 1 H), 7.94 (s, 1 H), 3.90 (s, 3 H), 3.82 (t, J=7.0 Hz, 4 H), 3.63 (t, J=6.9 Hz, 4 H), 3.48 (s, 3 H). Anal. ($C_{13}H_{16}Br_2N_2O_6S$) C, H, N.

A solution of 6 (1.00 g, 2.05 mmol) in a dioxane/MeOH (1:1, 20 mL) was treated at 10° C. with 4N aqueous KOH (5 mL), and stirred at 10° C. for 45 min. The mixture was acidified to pH 2 with 1 N aqueous HBr, concentrated to a small volume under reduced pressure, and then diluted with saturated aqueous NaBr (20 mL). The resulting semi-solid was isolated and crystallized twice from MeOH/$H_2O$ to give 5-[bis(2-bromoethyl)amino]-4-(methylsulfonyl)-2-nitrobenzoic acid (7) (0.70 g, 72%): mp 174-176° C.; $^1H$ NMR $[(CD_3)_2SO]$ δ 8.50 (s, 1 H), 7.88 (s, 1 H), 3.79 (t, J=7.0 Hz, 4 H), 3.62 (t, J=7.0 Hz, 4 H), 3.48 (s, 3 H). Anal. ($C_{12}H_{14}Br_2N_2O_6S$) C, H, N.

A finely-divided suspension of 7 (260 mmg, 0.55 mmol) in dry benzene (50 mL) was treated with $(COBr)_2$ (2.13 mL, 0.20 mmol) and catalytic DMF. The mixture was stirred for 2 h, then concentrated to dryness under reduced pressure and re-evaporated with benzene under high vacuum. The resulting crude acid bromide was dissolved in $Me_2CO$ (10 mL) and treated at –5° C. with a cold solution of 2-aminoethanol (101 mg, 1.65 mmol) in water (5 mL). The mixture was stirred at 0° C. for 5 min, then acidified to pH 4 with 1 N aqueous HBr, and concentrated under reduced pressure. The residue was chromatographed on silica gel, eluting with EtOAc, to give IIa-7s (222 mg, 78%): mp (EtOAc/$iPr_2O$) 126-127° C.; $^1H$ NMR $[(CD_3)_2SO]$ δ 8.75 (t, J=5.6 Hz, 1 H), 8.51 (s, 1 h), 7.68 (s, 1 H), 4.79 (t, J=5.4 Hz, 1 H), 3.76 (t, J =7.1 Hz, 4 H), 3.62 (t, J=7.0 Hz, 4 H), 3.54 (q, J =5.9 Hz, 2 H), 3.48 (s, 3 H), 3.31 (after $D_2O$ exchange, t, J=6.0 Hz, 2 H). HRMS (FAB) calcd. for $C_{14}H_{20}{}^{79}Br_2N_3O_6S$ $(MH^+)$ m/z 515.9440; found 515.9425.

Example 8

(Scheme 2c)

2 [(2-Bromoethyl)-5-[[(3-Hydroxypropyl)Amino] Carbonyl]-2,4-Dinitroanilino]Ethyl Methanesulfonate (IIa-13) and 5-[Bis(2-Iodoethyl)Amino]-N-(2-Hydroxyethyl)-2, 4-Dinitrobenzamide (IIa-14)

5-(Bis{2-[(methylsulfonyl)oxy]ethyl}amino)-2,4-dinitrobenzoic acid [A method of preparing this compound is disclosed in co-pending NZ Application No. 521851] (9) was heated under reflux in excess $SOCl_2$ (60 mL) and catalytic DMF for 1 h. Evaporation under reduced pressure, followed by azeotroping in benzene, gave the crude acid chloride. This was dissolved in dry $Me_2CO$ and treated at 0° C. with 3-amino-1-propanol at 0° C. for 5 min. The mixture was acidified to pH 2-3 with 0.2 N HCl, concentrated to half volume, and then solid NaBr was added, followed by extraction with EtOAc (2×). Evaporation, and chromatography of the residue on silica gel, eluting with EtOAc/MeOH (9:1), gave give 2-(5-{[(3-hydroxypropyl)amino]carbonyl } {2-[(methylsulfonyl)oxy]ethyl}-2,4-dinitroanilino)ethyl methanesulfonate (8) (68%) as a yellow gum; $^1H$ NMR $[(CD_3)_2SO]$ δ 8.54 (t, J=5.7 Hz, 1 H), 8.53 (s, 1 H), 7.45 (s, 1 H), 4.43 (t, J=5.1 Hz, 1 H), 4.33 (t, J=5.2 Hz, 4 H), 3.69 (t, J=5.2 Hz, 4 H), 3.57 (q, J=5.9 Hz, 2 H), 3.26 (after $D_2O$ exchange, t, J=7.0 Hz, 2 H), 3.12 (s, 6 H), 1.66 (pent, J=6.7 Hz, 2 H). HRMS (FAB) calcd. for $C_{16}H_{25}N_4O_{12}S$ $(MH^+)$ m/z 529.0910; found 529.0904.

A solution of 8 in DMF was treated with LiBr (1.4 equiv.), and worked up as above, and the product was chromatographed on silica gel. Elution with EtOAc gave a small amount of the dibromo mustard, while elution with EtOAc/MeOH (19:1) gave IIa-13 (31%) as a yellow gum: $^1$H NMR [(CD$_3$)$_2$SO] δ 8.60 (t, J=5.6 Hz, 1 H), 8.54 (s, 1 H), 7.44 (s, 1 H), 4.45 (t, J=5.2 Hz, 1 H), 4.33 (t, J=5.1 Hz, 2 H), 3.74 (t, J=5.2 Hz, 2 H), 3.72-3.66 (m, 4 H), 3.49 (q, J=5.9 Hz, 2 H), 3.27 (after D$_2$O exchange, t, J=7.0 Hz, 2 H), 3.14 (s, 3 H), 1.68 (pent, J=6.7 Hz, 2 H). HRMS (FAB) calcd. for C$_{15}$H$_{22}$$^{79}$BrN$_4$O$_9$S (MH$^+$) m/z 515.0270; found 515.0283.

Similar treatment of the acid chloride of 9 (activation with (COCl)$_2$/DMF) with 2-aminoethanol gave 2-(5-{[(2-hydroxyethyl)amino]carbonyl} {2-[(methylsulfonyl)oxy]ethyl}-2,4-dinitroanilino)ethyl methanesulfonate (10). A stirred mixture of 10 (1.42 g, 2.76 mmol) and NaI (3.3 g, 22 mmol) in dry MeCN (45 mL) was heated at reflux for 1 h, then concentrated under reduced pressure. The residue was partitioned between EtOAc and water, and the organic layer was washed with water and evaporated. The residue was chromatographed on silic gel, eluting with CH$_2$Cl$_2$/EtOAc (1:4), followed by recrystallisation from MeOH/EtOAc/i-Pr$_2$O to give IIa-14 (2.9 g, 81%): mp 142-143° C.; $^1$H NMR [(CD$_3$)$_2$SO] δ 8.73 (t, J=5.7 Hz, 1 H), 8.53 (s, 1 H), 7.38 (s, 1 H), 4.76 (t, J=5.5 Hz, 1 H), 3.68 (t, J=6.9 Hz, 4 H), 3.57-3.49 (m, 2 H), 3.39 (t, J=6.9 Hz, 4 H), 3.34-3.26 (m, partially obscured, 2 H). Anal. (C$_{13}$H$_{16}$I$_2$N$_4$O$_6$) C, H, N.

Example 9

2-(Aziridin-1-yl)-N-(6-Hydroxyhexyl)-3,5-Dinitrobenzamide (IIa-1)

A solution of 2-chloro-N-(6-hydroxyhexyl)-3,5-dinitrobenzamide (16) [for preparation see Example 14 below] (118 mg, 0.34 mmol) and Et$_3$N (200 mg) in EtOAc (200 mL) was treated with aziridine (100 mg) at room temperature for 3 h. The mixture was diluted with EtOAc and washed three times with water, after dry, concentrated under reduced pressure until about 20 mL, the yellow solid was collected and gave 101 mg product (84%); $^1$H NMR [(CD$_3$)$_2$SO] δ 8.74 (d, J=2.8 Hz, 1 H), 8.63 (m, 1 H), 8.29 (d, J=2.8 Hz, 1 H), 4.31 (m, 1 H), 3.39 (m, 2 H), 3.25 (m, 2 H), 2.37 (s, 4 H), 1.56 (m, 2 H), 1.43 (m, 2 H), 1.33 (m, 4 H). Anal. (C$_{15}$H$_{20}$N$_4$O$_6$) C, H, N.

Example 10

(Scheme 2d)

2-[Bis(2-Chloroethyl)Amino]-N-(2-Hydroxyethyl)-3,5-Dinitrobenzamide (IIb-2) and 2-[Bis(2-Bromoethyl)Amino]-N-(2-Hydroxyethyl)-3,5-Dinitrobenzamide (IIb-7)

2-Chloro-3,5-dinitrobenzoic acid (1) (18 g, 81 mmol) was treated with SOCl$_2$ (250 ml) containing one drop of DMF and heated under reflux for 6 h. Evaporation of reagent followed by azeotroping with benzene gave the crude acid chloride, which was dissolved in THF (200 mL) and added dropwise to a solution made of 25 mL of 2-aminoethanol in THF (400 mL) and cooled with dryice-acetone bath. After stirring for 20 min. the reaction mixture was acidified to pH 4-5 with 1 N HCl, most of the solvent was evaporated, and the residue was partitioned between water (250 mL) and EtOAc (300 mL). The aqueous phase was extracted with EtOAc, and the combined organic phases were washed with sat. NaHCO$_3$, 1 N HCl and brine respectively, then concentrated to give 2-chloro-N-(2-hydroxyethyl)-3,5-dinitrobenzamide (2) 21.34 g (91%) as a white solid: mp (EtOAc) 159-160° C.; $^1$H NMR [(CD$_3$)$_2$SO] δ 8.99 (d, J=2.6 Hz, 1 H, H-4), 8.86 (m, 1 H, CONH), 8.56 (d, J=2.6 Hz, 1 H, H-6), 4.83 (m, 1 H, OH), 3.54 (m, 4 H). Anal. (C$_9$H$_8$ClN$_3$O$_6$) C, H, N.

A solution of 12 (1.52 g, 5.3 mmol) and Et$_3$N (4 mL) in p-dioxane (60 mL) was treated with N,N-bis(2-chloroethyl) amine hydrochloride (3.0 g, 16.5 mmol) at 50° C. for 24 h. The mixture was poured into water and extracted with EtOAc to give the crude product, which was chromatographed on silica gel. Elution with EtOAc/petroleum ether (4:1) and concentration of the eluate under reduced pressure gave a oily residue that was dissolved in minimum amount of EtOAc. Petroleum ether was added slowly until incipient cloudiness, and the solution was stood overnight to precipitate 2-[bis(2-chloroethyl)amino]-N-(2-hydroxyethyl)-3,5-dinitrobenzamide (IIb-2) (2.07 g, 100%) as yellow crystals: mp (EtOAc/petroleum ether) 109-111° C.; $^1$H NMR [(CD$_3$)$_2$SO] δ8.73 (d, J=2.6 Hz, 1 H, H-4), 8.72 (m, 1 H, CONH), 8.34 (d, J=2.6 Hz 1 H, H-6), 4.83 (m, 1 H, OH), 3.72 (m, 4 H, 2xCH$_2$Cl), 3.55 (m, 2 H), 3.42 (m, 4 H, 2xCH$_2$N), 3.34 (m, 2 H); $^{13}$C NMR δ 165.3, 145.8, 145.3, 141.0, 136.3, 127.5, 122.1, 59.1, 54.1, 42.1, 41.5. HRMS (FAB) [MH$^+$] Calcd. For C$_{13}$H$_{17}$$^{35}$Cl$_2$N$_4$O$_6$ m/z 395.0525. Found; 395.0525.

A solution of IIb-2 (1.20 g, 3.0 mmol) and LiBr (5.0 g, 58 mmol) in 3-methyl-2-butanone (20 mL) was heated under reflux for 6 h, then cooled and poured into water. Extraction with EtOAc gave a crude product (<95% pure), that was re-treated with LiBr (5.0 g, 58 mmol) in 3-methyl-2-butanone for a further 4 h, then worked up and chromatographed on silica gel, eluting with EtOAc/petroleum ether (from 1:1 to 1:0), to give IIb-7 (1.39 g, 95%): mp (EtOAc/petroleum ether) 105-108° C.; $^1$H NMR [(CD$_3$)$_2$SO] δ 8.74 (d, J=2.7 Hz, 1 H, H-4), 8.73 (m, 1 H, CONH), 8.34 (d, J=2.7 Hz, 1 H, H-6), 4.83 (m, 1 H, OH), 3.59-3.29 (m, 12 H); $^{13}$C NMR δ 165.3, 145.4, 145.3, 141.1, 136.5, 127.4, 122.1, 59.3, 53.9, 42.1, 30.0. HRMS (FAB) Calcd. For C$_{13}$H$_{17}$$^{79}$Br$_2$N$_4$O$_6$ [M+H$^+$] m/z 482.9515. Found; 482.9492. Anal. (C$_{13}$H$_{16}$Br$_2$N$_4$O$_6$) H, N, Br; C: found, 32.9; calculated 32.3%.

Example 11

(Scheme 2d)

2-[Bis(2-Chloroethyl)Amino]-N-(3-Hydroxypropyl)-3,5-Dinitrobenzamide (IIb-3) and 2-[Bis(2-Bromoethyl)Amino]-N-(3-Hydroxypropyl)-3,5-Dinitrobenzamide (IIb-8)

Reaction of the acid chloride of 11 (17 g) with 3-aminopropanol (7.5 g) in Me$_2$CO (120 mL) at 0° C. as described above, gave 2-chloro-N-(3-hydroxypropyl)-3,5-dinitrobenzamide (13) (5.06 g, 26%): mp (EtOAc/petroleum ether) 120-121° C.; $^1$H NMR [(CD$_3$)$_2$SO] δ 8.99 (d, J=2.6 Hz, 1 H, H-4), 8.79 (m, 1 H, CONH), 8.51 (d, J=2.6 Hz, 1 H, H-6), 4.50 (m, 1 H, OH), 3.49 (m, 2 H), 3.32 (m, 2 H), 1.70 (m, 2 H). Anal. (C$_{10}$H$_{10}$ClN$_3$O$_6$) C, H, N.

A solution of 13 (1.39 g, 4.58 mmol) and Et$_3$N (4 mL) in p-dioxane (60 mL) was treated with N,N-bis(2-chloroethyl) amine hydrochloride (2.9 g, 16.0 mmol) at 50 C. for 24 h. Workup as described above gave IIb-3 (1.84 g, 100%): mp (EtOAc/petroleum ether) 89-91° C.; $^1$H NMR [(CD$_3$)$_2$SO] δ8.74 (d, J=2.7 Hz, 1 H, H-4), 8.71 (m, 1 H, CONH), 8.30 (d, J=2.7 Hz, 1 H, H-6), 4.52 (m, 1 H, OH), 3.71 (m, 4 H, 2xCH$_2$Cl), 3.50 (m, 2 H), 3.42 (m, 4 H, 2xCH$_2$N), 3.32 (m, 2 H), 1.71 (m, 2 H); $^{13}$C NMR δ 165.1, 145.7, 145.5, 141.0, 136.4, 127.3, 122.1, 58.4, 54.1, 41.5, 36.7, 31.8. HRMS (FAB) Calcd. For $C_{14}H_{19}{}^{35}Cl_2N_4O_6$ [M+H$^+$]m/z 409.0682. Found; 409.0678.

Treatment of IIb-3 with LiBr in 3-methyl-2-butanone twice, as described above, gave IIb-8 (74% yield): mp (EtOAc/petroleum ether) 89-94° C.; $^1$H NMR [(CD$_3$)$_2$SO] δ 8.74 (d, J=2.7 Hz, 1 H, H-4), 8.72 (m, 1 H, CONH), 8.30 (d, J=2.7 Hz, 1 H, H-6), 3.77-3.44 (m, 12 H), 1.70 (m, 2 H); $^{13}$C NMR δ 165.1, 145.5, 145.3, 141.2, 136.5, 127.3, 122.1, 58.4, 54.0, 36.7, 31.8, 29.9. HRMS (FAB) Calcd. For $C_{14}H_{19}{}^{79}Br_2N_4O_6$ [M+H$^+$] m/z 496.9671. Found; 496.9658.

Example 12

(Scheme 2d)

2-[Bis(2-Chloroethyl)Amino]-N-(4-Hydroxybutyl)-3,5-Dinitrobenzamide (IIb-4) and 2-[Bis(2-Bromoethyl)Amino]-N-(4-Hydroxybutyl)-3,5-Dinitrobenzamide (IIb-9)

Reaction of the acid chloride of 11 (2.65 g, 10 mmol) with 4-aminobutanol (1.9 g) as above, followed by acidification to pH 4-5 with 1 N HCl and evaporation of most of the solvent gave a residue. This was partitioned between water (50 mL) and EtOAc (100 mL). The aqueous phase was extracted with EtOAc, and the combined organic phase were washed with sat. NaHCO$_3$, 1 N HCl and brine respectively, then concentrated to give 2-chloro-N-(4-hydroxybutyl)-3,5-dinitrobenzamide (14) 1.11 g (35%): mp (EtOAc) 121-124° C.; $^1$H NMR [(CD$_3$)$_2$SO] δ 8.98 (d, J =2.7 Hz, 1 H), 8.79 (m, 1 H), 8.52 (d, J=2.7 Hz, 1 H), 4.43 (m, 1 H), 3.43 (m, 2 H), 3.26 (m, 2 H), 1.54 (m, 4 H); $^{13}$C NMR δ 162.6, 148.4, 145.9, 140.4, 128.2, 125.8, 120.4, 60.2, 39.1, 29.8, 25.3. Anal. ($C_{11}H_{12}ClN_3O_6$) C, H, N.

A solution of 14 (0.75 g, 2.3 mmol) and Et$_3$N (2 mL) in p-dioxane (30 mL) was treated with N,N-bis(2-chloroethyl)amine hydrochloride (1.5 g, 8.0 mmol) at 50° C. for 24 h. The mixture was poured into water and extracted with EtOAc gave the crude product which was chromatographed on silica gel. Elution with EtOAc/petroleum ether (4:1) gave IIb-4 (0.99 g, 100%) as yellow foam; $^1$H NMR [(CD$_3$)$_2$SO] δ 8.71 (d, J=2.8 Hz, 1 H), 8.69 (m, 1 H), 8.27 (d, J=2.8 Hz, 1 H), 4.37 (m, 1 H), 3.70 (m, 4 H), 3.38 (m, 6 H), 3.25 (m, 2 H), 1.56 (m, 2 H), 1.47 (m, 2 H); $^{13}$C NMR δ 165.0, 145.7, 145.5, 141.0, 136.4, 127.2, 122.0, 60.2, 54.2, 41.5, 39.2, 29.8, 25.2. HRMS (FAB) Calcd. For $C_{15}H_{21}{}^{35}Cl_2N_4O_6$ [M+H$^+$] m/z 423.0838. Found; 423.0847.

A solution of IIb-4 (0.96 g, 3.04 mmol) and LiBr (5 g) in 3-methyl-2-butanone (15 mL) was heated under reflux for 6 h, then cooled and poured into water. Extraction with EtOAc gave a crude product (<95% pure), that was re-treated with LiBr (5 g) in 3-methyl-2-butanone for a further 4 h, then worked up and chromatographed on silica gel, eluting with EtOAc/petroleum ether (from 1:1 to 3:1) give IIb-9 (1.01 g, 87%) as a yellow foam; $^1$H NMR [(CD$_3$)$_2$SO] δ 8.74 (d, J=2.8 Hz, 1 H), 8.72 (m, 1 H), 8.28 (d, J=2.8 Hz, 1 H), 3.60-3.26 (m, 12 H), 1.58 (m, 2 H), 1.49 (m, 2 H); $^{13}$C NMR δ 165.0, 145.6, 145.2, 141.2, 136.5, 127.2, 122.0, 60.2, 54.1, 39.2, 29.9, 29.8, 25.2. HRMS (FAB) Calcd. For $C_{15}H_{21}{}^{79}Br_2N_4O_6$ [M+H$^+$] m/z 510.9828. Found; 510.9832.

Example 13

(Scheme 2d)

2-[Bis(2-Chloroethyl)Amino]-N-(5-Hydroxypentyl)-3,5-Dinitrobenzamide (IIb-5) and 2-[Bis(2-Bromoethyl)Amino]-N-(5-Hydroxypentyl)-3,5-Dinitrobenzamide (IIb-10)

Similar reaction of the acid chloride of 11 with 5-aminopentanol as above gave 2-chloro-N-(5-hydroxypentyl)-3,5-dinitrobenzamide (15), 1.3 g (39%), mp (EtOAc) 105-108° C.; $^1$H NMR [(CD$_3$)$_2$SO] δ 8.98 (d, J=2.7 Hz, 1 H), 8.79 (m, 1 H), 8.50 (d, J=2.7 Hz, 1 H), 4.35 (m, 1 H), 3.39 (m, 2 H), 3.26 (m, 2 H), 1.54 (m, 2 H), 1.44 (m, 2 H), 1.36 (m, 2 H); $^{13}$C NMR δ 162.7, 148.4, 145.9, 140.4, 128.2, 125.8, 120.4, 60.5, 39.1, 32.0, 28.4, 22.8. Anal. ($C_{12}H_{14}ClN_3O_6$) C, H, N.

A solution of 15 (0.63 g, 2.3 mmol) and Et$_3$N (2 mL) in p-dioxane (30 mL) was treated with N,N-bis(2-chloroethyl)amine hydrochloride (1.5 g, 8.0 mmol) at 50° C. for 24 h. The mixture was poured into water and extracted with EtOAc to gave the crude product which was chromatographed on silica gel. Elution with EtOAc/petroleum ether (4:1) gave IIb-5 (0.82 g, 100%) as yellow foam; $^1$H NMR [(CD$_3$)$_2$SO] δ 8.73 (d, J=2.8 Hz, 1 H), 8.69 (m, 1 H), 8.28 (d, J=2.8 Hz, 1 H), 4.32 (m, 1 H), 3.70 (m, 4 H), 3.40 (m, 6 H), 3.25 (m, 2 H), 1.55 (m, 2 H), 1.47 (m, 2 H), 1.37 (m, 2 H); $^{13}$C NMR δ 165.0, 145.7, 145.5, 141.0, 136.4, 127.2, 122.0, 60.5, 54.2, 41.5, 39.3, 32.0, 28.3, 22.9. HRMS (FAB) Calcd. For $C_{16}H_{23}{}^{35}Cl_2N_4O_6$ [M+H$^+$] m/z 437.0995. Found; 437.0991.

Similar reaction of IIb-5 (1.3 g) with LiBr gave IIb-10 (1.35 g, 86%) as a yellow foam; $^1$H NMR [(CD$_3$)$_2$SO] δ 8.74 (d, J=2.8 Hz, 1 H), 8.71 (m, 1 H), 8.28 (d, J=2.8 Hz, 1 H), 3.60-3.26 (m, 12 H), 1.55 (m, 2 H), 1.48 (m, 2 H), 1.37 (m, 2 H); $^{13}$C NMR δ 165.0, 145.6, 145.2, 141.2, 136.5, 127.2, 122.0, 60.5, 54.1, 39.3, 32.0, 29.8, 28.4, 22.9. HRMS (FAB) Calcd. For $C_{16}H_{23}{}^{79}Br_2N_4O_6$ [M+H$^+$] m/z 524.9984. Found; 524.9975.

Example 14

(Scheme 2d)

2-[Bis(2-Chloroethyl)Amino]-N-(6-Hydroxybexyl)-3,5-Dinitrobenzamide (IIb-6) and 2-[Bis(2-Bromoethyl)Amino]-N-(6-Hydroxyhexyl)-3,5-Dinitrobenzamide (IIb-11)

Similar reaction of the acid chloride of 11 with 6-aminohexanol as above gave 2-chloro-N-(6-hydroxyhexyl)-3,5-dinitrobenzamide (16), 0.9 g (26%), mp (EtOAc) 88-91° C.; $^1$H NMR [(CD$_3$)$_2$SO] δ 8.98 (d, J=2.7 Hz, 1 H), 8.78 (m, 1 H), 8.49 (d, J=2.7 Hz, 1 H), 4.32 (m, 1 ), 3.39 (m, 2 H), 3.26 (m, 2 H), 1.54 (m, 2 H), 1.44 (m, 2 H), 1.34 (m, 4 H); $^{13}$C NMR δ 162.7, 148.4, 145.9, 140.4, 128.2, 125.8, 120.4, 60.5, 39.1, 32.3, 28.6, 26.2, 25.1. Anal. ($C_{13}H_{16}ClN_3O_6$) C, H, N.

A solution of 16 (0.67 g, 2.5 mmol) and Et$_3$N (2 mL) in p-dioxane (30 mL) was treated with N,N-bis(2-chloroethyl)amine hydrochloride (1.5 g, 8.0 mmol) at 50° C. for 24 h. The mixture was poured into water and extracted with EtOAc to gave the crude product which was chromatographed on silica gel. Elution with EtOAc/petroleum ether (4:1) gave IIb-6 (0.87 g, 100%) as yellow foam; $^1$H NMR [(CD$_3$)$_2$SO] δ 8.73 (d, J=2.8 Hz, 1 H), 8.70 (m, 1 H), 8.28 (d, J=2.8 Hz, 1 H), 4.31 (m, 1 H), 3.70 (m, 4 H), 3.38 (m, 6 H), 3.25 (m, 2 H), 1.54 (m, 2 H), 1.40 (m, 2 H), 1.32 (m, 4 H); $^{13}$C NMR δ 165.0, 145.7, 145.6, 141.0, 136.4, 127.2, 122.0, 60.5, 54.2, 41.5, 39.2, 32.3, 28.5, 26.3, 25.1. HRMS (FAB) Calcd. For $C_{17}H_{25}{}^{35}Cl_2N_4O_6$ [M+H$^+$] m/z 451.1151. Found; 451.1154.

Similar reaction of IIb-6 (0.97 g) with LiBr gave IIb-11 (0.96 g, 81%) as a yellow foam; $^1$H NMR [(CD$_3$)$_2$SO] δ 8.74 (d, J=2.8 Hz, 1 H), 8.70 (m, 1 H), 8.28 (d, J=2.8 Hz, 1 H), 3.60-3.26 (m, 12 H), 1.54 (m, 2 H), 1.43 (m, 2 H), 1.32 (m, 4 H); $^{13}$C NMR δ 165.0, 145.6, 145.2, 141.2, 136.5, 127.2, 122.0, 60.6, 54.1, 39.2, 32.4, 29.9, 28.5, 26.3, 25.1. HRMS (FAB) Calcd. For $C_{17}H_{25}{}^{79}Br_2N_4O_6$ [M+H$^+$] m/z 539.0141. Found; 539.0135.

Example 15

(Scheme 2e)

2-[Bis(2-Bromopropyl)Amino]-N-(2-Hydroxyethyl)-3,5-Dinitrobenzamide (IIb-7a)

Reaction of 2-chloro-3,5-dinitro-N-[2-(tetrahydro-2H-pyran-2-yloxy)ethyl]benzamide (17) (1.02 g) [For method of preparation see co-pending NZ Application No. 521851] with diisopropanolamine (0.8 g) as above gave 2-[bis(2-hydroxypropanyl)amino]-3,5-dinitro-N-[2-(tetrahydro-2H-pyran-2-yloxy)ethyl]benzamide (18) (1.29 g, 100%): as a yellow foam; $^1$H NMR [(CD$_3$)$_2$SO] δ 9.22 (br, 1 H), 8.66 (d, J=2.8 Hz, 1 H), 8.29 (d, J=2.8 Hz, 1 H), 4.99 (m, 1 H), 4.85 (br, 1 H), 4.62 (br, 1 H), 3.94 (m, 2 H), 3.77 (m, 2 H), 3.53 (m, 4 H), 3.26 (m, 2 H), 1.48 (m, 10 H), 0.98 (m, 6 H); $^{13}$C NMR δ 166.5, 147.8, 142.4, 138.2, 132.6, 128.8, 123.8, 98.1, 64.8, 63.5, 61.5, 60.1, 30.1, 25.0, 20.5, 20.2, 19.1. HRMS (FAB) Calcd. For $C_{20}H_{31}N_4O_9$ [M+H$^+$] m/z 471.2091. Found; 471.2089.

Reaction of 18 with MsCl as above gave 1-methyl-2-[{2-[(methylsulfonyl)oxy]propyl}-2,4-dinitro-6-({[2-(tetrahydro-2H-pyran-2-yloxy)ethyl]amino}carbonyl)anilino]ethyl methanesulfonate (19) (2.52 g, 100%): as a yellow foam; which was used directly for the next step.

A solution of 19 (2.52 g, 4.03 mmol) in THF (150 mL) was treated with 1 N HCl (100 mL), and the solution was stirred at 20° C. for 1 h, then diluted with water (100 mL), neutralized with satd. NaHCO$_3$, and extracted with EtOAc (3×80 mL). The combined organic phases were washed with brine and dried, the solvent was evaporated, and the residue was purified by chromatography on silica gel, eluting with EtOAc/MeOH (100:1), to give 2-(2-{[(2-hydroxyethyl)amino]carbonyl}{2-[(methylsulfonyl)oxy]propyl}-4,6-dinitroanilino)-1-methylethyl methanesulfonate (20) (0.80 g, 37%): as a yellow foam; $^1$H NMR [(CD$_3$)$_2$SO] δ 8.94 (m, 1 H), 8.72 (m, 1 H), 8.35 (m, 1 H), 4.92 (m, 2 H), 3.56 (m, 2 H), 3.30 (m, 6 H), 3.16 (s, 6 H), 1.32 (m, 6 H); $^{13}$C NMR δ 165.9, 145.8, 143.4, 139.4, 133.6, 128.0, 123.1, 76.3, 59.2, 57.3, 42.2, 37.7, 18.6. HRMS (FAB) Calcd. For $C_{17}H_{27}N_4O_{12}S_2$ [M+H$^+$] m/z 543.1067. Found; 543.1074.

Treatment of 20 (0.52 g, 0.96 mmol) with LiBr (0.5 g, 5.8 mmol) in EtOAc (50 mL) at 60° C. for 3 h, and chromatography of the product on silica gel, eluting with EtOAc/petroleum ether (from 2:1 to 1:0) gave IIb-7a (0.31 g, 62%): as yellow solid: mp (EtOAc/petroleum ether) 127-130° C.; $^1$H NMR [(CD$_3$)$_2$SO] δ 8.91 (m, 1 H, CONH), 8.70 (d, J=2.8 Hz, 1 H, H-4), 8.32 (d, J=2.8 Hz, 1 H, H-6), 4.80 (m, 1 H), 4.42 (m, 2 H), 3.55 (m, 4 H), 1.62 (m, 6 H); $^{13}$C NMR δ 165.8, 144.8, 143.5, 139.6, 133.6, 128.0, 122.9, 60.6, 59.2, 47.9, 42.2, 23.4. Anal. ($C_{15}H_{20}Br_2N_4O_6$) C, H, N.

Example 16

(Scheme 2f)

2-((2-Bromoethyl)-2-{[(2-Hydroxypropyl)Amino]Carbonyl}-4,6-Dinitroanilino)Ethyl Methanesulfonate (IIb-13)

A solution of 13 (1.22 g, 4.0 mmol) in 50 mL of CH$_2$Cl$_2$ was cooled in an ice-bath, and 3,4-dihydro-2H-pyran (1.0 mL) and p-toluenesulfonic acid (0.1 g) were added. The reaction mixture was stirred for 2 h, then concentrated under reduced pressure. Chromatography of the residue on silica gel, eluting with EtOAc/petroleum ether (from 1:2 to 2:1), gave 2-chloro-3,5-dinitro-N-[2-(tetrahydro-2H-pyran-2-yloxy)propyl]benzamide (21) (1.45 g, 94%): as a pale yellow oil; $^1$H NMR [(CD$_3$)$_2$SO] δ 8.99 (d, J=2.7 Hz, 1 H, H-4), 8.81 (m, 1 H, CONH), 8.51 (d, J=2.7 Hz, 1 H, H-6), 4.57 (m, 1 H), 3.72 (m, 2 H), 3.46-3.25 (m, 4 H), 1.82-1.44 (m, 8 H). $^{13}$C NMR δ 162.7, 148.4, 145.9, 140.3, 128.2, 125.8, 120.5, 98.0, 64.2, 61.3, 36.5, 30.2, 28.9, 24.9, 19.1. HRMS (FAB) Calcd. For $C_{15}H_{19}{}^{35}ClN_3O_7$ [M+H$^+$] m/z 388.0912. Found; 388.0915.

Reaction of 21 (1.45 g, 3.75 mmol) with diethanolamine (1.67 g) as above gave 2-[bis(2-hydroxyethyl)amino]-3,5-dinitro-N-[2-(tetrahydro-2H-pyran-2-yloxy)propyl]benzamide (22) (1.62 g, 95%): as a yellow foam; $^1$H NMR [(CD$_3$)$_2$SO] δ 8.96 (m, 1 H, CONH), 8.66 (d, J=2.8 Hz, 1 H, H-4), 8.31 (d, J=2.8 Hz, 1 H, H-6), 4.95 (m, 2 H), 4.56 (m, 1 H), 3.79-3.16 (m, 14 H), 1.80-1.45 (m, 8 H); $^{13}$C NMR δ 166.2, 148.1, 143.6, 139.3, 133.8, 128.9, 123.8, 98.5, 64.8, 61.7, 58.5, 54.6, 37.3, 30.6, 29.2, 25.4, 19.6. HRMS (FAB) Calcd. For $C_{19}H_{29}N_4O_6$ [M+H$^+$] m/z 457.1935. Found; 457.1939.

Reaction of 22 (1.62 g, 3.55 mmol) with MsCl (2 mL) as above gave 2-[{2-[(methylsulfonyl)oxy]ethyl}-5,6-dinitro-6-({[2-(tetrahydro-2H-pyran-2-yloxy)propyl]amino}carbonyl)anilino]ethyl methanesulfonate (23) (2.17 g, 100%): as a yellow foam; $^1$H NMR [(CD$_3$)$_2$SO] δ 8.71 (d, J=2.8 Hz, 1 H), 8.71 (m, 1 H), 8.31 (d, J=2.8 Hz, 1 H), 4.26 (m, 4 H), 3.71-3.37 (m, 10 H), 3.13 (s, 6 H), 3.10 (m, 2 H), 1.82-1.43 (m, 8 H); $^{13}$C NMR δ 165.1, 146.3, 145.4, 140.9, 135.9, 127.4, 122.2, 98.0, 67.2, 64.3, 51.4, 45.7, 36.5, 30.2, 28.7, 24.9, 19.1, 8.5. HRMS (FAB) Calcd. For $C_{21}H_{33}N_4O_{13}S_2$ [M+H$^+$] m/z 613.1486. Found; 613.1481.

A solution of 23 (2.95 g, 3.55 mmol) in THF (120 mL) was treated with 1 N HCl (80 mL), and the solution was stirred at 20° C. for 1 h, then diluted with water (100 mL), neutralized with satd. NaHCO$_3$, and extracted with EtOAc (3×80 mL). The combined organic phases were washed with brine and dried, the solvent was evaporated, and the residue was purified by chromatography on silica gel, eluting with EtOAc/MeOH (100:1), to give 2-(2-{[(3-hydroxypropyl)amino]carbonyl}{2-[(methylsulfonyl)oxy]ethyl}-4,6-dinitroanilino) ethyl methanesulfonate (24) (1.4 g, 75%): as a yellow solid: mp (EtOAc/petroleum ether) 130-133° C.; $^1$H NMR [(CD$_3$)$_2$SO] δ 8.74 (d, J=2.8 Hz, 1 H), 8.72 (m, 1 H), 8.32 (d, J=2.8 Hz, 1 H), 4.29 (m, 4 H), 3.47 (m, 8 H), 3.14 (s, 6 H), 1.71 (m, 2 H); $^{13}$C NMR δ 165.2, 146.3, 145.3, 140.8, 135.9, 127.5, 122.3, 67.3, 58.4, 51.4, 36.8, 36.5, 31.7. Anal. ($C_{16}H_{24}N_4O_{12}S_2$) C, H, N.

Treatment of 24 (0.25 g, 0.45 mmol) with LiBr (53 mg, 0.61 mmol) in EtOAc (50 mL) at 60° C. for 3 h, and chromatography of the product on silica gel, eluting with EtOAc/ petroleum ether (from 2:1 to 1:0) gave IIb-13 (0.16 g, 66%): as yellow foam; $^1$H NMR [(CD$_3$)$_2$SO] δ 8.74 (d, J=2.8 Hz, 1 H), 8.73 (m, 1 H), 8.31 (d, J=2.8 Hz, 1 H), 4.28 (m, 2 H), 3.65-3.44 (m, 10 H), 3.13 (s, 3 H), 1.70 (m, 2 H); $^{13}$C NMR δ 165.1, 145.7, 145.4, 141.0, 136.2, 127.3, 122.1, 67.5, 58.4, 51.1, 36.7, 36.5, 31.7, 29.6. HRMS (FAB) Calcd. For C$_{15}$H$_{22}$$^{79}$BrN$_4$O$_9$S [M+H$^+$] m/z 513.0291. Found; 513.0281.

Example 17

(Scheme 2g)

2-((2-Bromoethyl)-2-{[(2-Hydroxyethyl)Amino] Carbonyl}-4,6-Dinitroanilino)Ethyl Methanesulfonate (IIb-12)

Solid IIb-7 (300 mg, 0.62 mmol) and silver methanesulfonate (130 mg, 0.65 mmol) in dry MeCN (15 mL) were heated under reflux for 3 h, then cooled and filtered. The solid AgBr was washed with EtOAc to give a 98% yield of AgBr. The solvent was removed at reduced pressure and the residue was separated by chromatography on silica gel, eluting with EtOAc/petroleum ether (from 1:1 to 1:0), to give successively:

starting material (IIb-7) (28 mg, 9%).

IIb-12 (123 mg, 38%) as a yellow foam; $^1$H NMR [(CD$_3$)$_2$SO] δ 8.77 (m, 1 H, CONH), 8.74 (d, J=2.7 Hz, 1 H, H-4), 8.36 (d, J=2.7 Hz, 1 H, H-6), 4.28 (m, 2 H, CH$_2$OMs), 3.58 (m, 4 H), 3.44 (m, 4 H), 3.14 (s, 3 H, OSO$_2$CH$_3$); $^{13}$C NMR δ 165.3, 145.8, 145.2, 140,9, 135.1, 127.5, 122.2, 67.5, 59.2, 54.2, 51.0, 42.1, 36.4, 29.7; HRMS m/z required for C$_{14}$H$_{20}$$^{79}$BrN$_4$O$_9$S 499.01344; Found 499.01324.

The column was finally eluted with EtOAc/MeOH (9:1) to give 2-(2-{[(2-hydroxyethyl)amino]carbonyl}{2-[(methylsulfonyl)oxy]ethyl}-4,6-dinitroanilino)ethyl methanesulfonate 25 (159 mg, 53%) as a yellow solid: mp 128-132° C. (EtOAc/petroleum ether); $^1$H NMR [(CD$_3$)$_2$SO] δ 8.78 (m, 1 H, CONH), 8.74 (d, J=2.7 Hz, 1 H, H-4), 8.36 (d, J=2.7 Hz, 1 H, H-6), 4.29 (m, 4 H, 2xCH$_2$OMs), 3.56 (m, 2 H), 3.45 (m, 6 H), 3.14 (s, 6 H, 2xOSO$_2$CH$_3$); $^{13}$C NMR δ 165.4, 146.3, 145.1, 140,6, 135.8, 127.6, 122.3, 67.3, 59.2, 51.3, 42.1,36.4; HRMS: C$_{15}$H$_{23}$N$_4$O$_{12}$S$_2$ requires m/z 515.0754. Found: 515.0744.

Example 18

(Scheme 2h)

2-((2-Chloroethyl)-2-{[(2-Hydroxyethyl)Amino] Carbonyl}-4,6-Dinitroanilino)Ethyl Methanesulfonate (IIb-2m)

A solution of 25 (5.3 g, 10.3 mmol) in DMF (100 mL) was treated with LiCl (524 mg, 12.4 mmol) at 60° C. for 2 h, and then cooled, poured into dilute HCl and extracted with EtOAc (3×150 mL). Workup and chromatography of the product on silica gel, eluting with EtOAc/petroleum ether from 1:1 to 1:0, gave IIb-2 (2.4 g, 59%), and then IIb-2m (1.94 g, 41%) as yellow oil; $^1$H NMR [(CD$_3$)$_2$SO] δ 8.77 (m, 1 H, CONH), 8.74 (d, J=2.7 Hz, 1 H, H-4), 8.36 (d, J=2.7 Hz, 1 H, H-6), 4.28 (m, 2 H, —CH$_2$O-Ms), 3.58 (m, 4 H), 3.44 (m, 4 H), 3.14 (s, 3 H, —OSO$_2$CH$_3$); $^{13}$C NMR δ 165.3, 145.8, 145.2, 140,9, 135.1, 127.5, 122.2, 67.5, 59.2, 54.2, 51.0, 42.1, 36.4, 29.7.

IIb-2m was prepared by an alternative method as following: A solution of IIb-2 (12.50 g, 31.6 mmol) in 3-methyl-2-butanone (150 mL) was treated at 25° C. with NaI (5.69 g, 38.0 mmol) and the mixture was stirred at 70° C. for 2 h and then concentrated under reduced pressure. The residue was partitioned between water (250 mL) and EtOAc (250 mL) and the separated organic layer was washed with water, dried (Na$_2$SO$_4$) and then concentrated under reduced pressure. The resulting oil (15.23 g) was dissolved in CH$_3$CN (80 mL), treated with silver methanesulfonate (9.63 g, 47.4 mmol) and the mixture was stirred at 25° C. for 1 h and then concentrated under reduced pressure. The residue was extracted with EtOAc (200 mL), filtered, the solids were washed with EtOAc (100 mL) and the EtOAc solution was evaporated and the oily mixture was separated by chromatography on silica gel as above and gave starting material (3.61 g, 29%), IIb-2m (4.55 g, 32%) and 25 (4.98 g, 31%). When NaI was replaced by LiBr the reaction gave a similar result.

Example 19

(Scheme 2i)

2-[Bis(2-Iodoethyl)Amino]-N-(2-Hydroxyethyl)-3,5-Dinitrobenzamide (IIb-14) and 2-((2-Iodoethyl)-2-{[(2-Hydroxyethyl)Amino]Carbonyl}-4,6-Dinitroanilino)Ethyl Methanesulfonate (IIb-15)

Treatment of 25 (6.7 g, 13.0 mmol) with NaI (2.9 g, 20 mmol) in EtOAc (200 mL) at 60° C. for 3 h, and chromatography of the product on silica gel, eluting with EtOAc/petroleum ether (from 2:1 to 1:0) gave IIb-14 (3.3 g, 44%) as a yellow solid: mp (EtOAc/petroleum ether) 129-131° C.; $^1$H NMR [(CD$_3$)$_2$SO] δ 8.72 (d, J=2.8 Hz, 1 H, H-4), 8.70 (m, 1 H, CONH), 8.32 (d, J=2.8 Hz, 1 H, H-6), 4.80 (m, 1 H), 3.55 (m, 2 H), 3.43 (m, 4 H), 3.31 (m, 6 H); $^{13}$C NMR δ 165.3, 145.2, 144.7, 141.0, 136.3, 127.3, 122.0, 59.3, 54.7, 42.1, 2.94. Anal (C$_{13}$H$_{16}$N$_4$I$_2$O$_6$) C, H, N.

Later eluates gave IIb-15 (1.35 g, 19%) as a yellow foam; $^1$H NMR [(CD$_3$)$_2$SO] δ 8.74 (d, J=2.8 Hz, 1 H, H-4), 8.74 (m, 1 H, CONH), 8.34 (d, J=2.8 Hz, 1 H, H-6), 4.28 (m, 2 H), 3.56 (m, 2 H), 3.43 (m, 2 H), 3.31 (m, 6 H), 3.13 (s, 3 H); $^{13}$C NMR δ 165.3, 145.5, 145.2, 140.8, 136.1, 127.4, 122.1, 67.5, 59.2, 55.4, 50.6, 42.1, 36.5, 2.6. HRMS (FAB) Calcd. For C$_{14}$H$_{20}$IN$_4$O$_9$S [M+H$^+$] m/z 546.9996. Found; 546.9997.

Example 20

(Scheme 2j)

3-[Bis(2-Bromoethyl)Amino]-N-(2-Hydroxyethyl)-2,6-Dinitrobenzamide (IIc-7) and 2-((2-Bromoethyl)-3-{[(2-Hydroxyethyl)Amino]carbonyl}-2,4-Dinitroanilino)Ethyl Methanesulfonate (IIc-12)

Treatment of 2-(3-{[(2-hydroxyethyl)amino]carbonyl}{2-[(methylsulfonyl)oxy]ethyl}-2,4-dinitroanilino)ethyl methanesulfonate (26) [for method of preparation see NZ Application No. 521851] (310 mg, 0.6 mmol) in EtOAc (50 mL) with LiBr (78 mg, 0.9 mmol), followed by chromatography on silica gel and elution with EtOAc/petroleum ether (from 1:1 to 1:0) gave IIc-7 (70 mg, 25%) as a foam; $^1$H NMR [(CD$_3$)$_2$SO] δ 8.80 (m, 1 H, CONH), 8.24 (d, J=9.4 Hz, 1 H), 7.63 (d, J=9.4 Hz, 1 H), 4.66 (m, 1 H), 3.70 (m, 4 H), 3.60 (m, 4 H), 3.45 (m, 2 H), 3.22 (m, 2 H); $^{13}$C NMR δ 161.4, 145.8, 140.2, 137.5, 129.2, 127.6, 122.6, 59.0, 52.6, 41.7, 30.0. HRMS (FAB) Calcd. For C$_{13}$H$_{17}$$^{79}$Br$_2$N$_4$O$_6$ [M+H$^+$] m/z 482.9515. Found; 482.9508.

Further elution with EtOAc/MeOH (50:2) gave IIc-12 (118 mg, 39%): mp. 94-97° C,; $^1$H NMR [(CD$_3$)$_2$SO] δ 8.80 (m, 1

H, CONH), 8.25 (d, J=9.4 Hz, 1 H), 7.64 (d, J=9.4 Hz, 1 H), 4.67 (m, 1 H), 4.27 (m, 2 H), 3.63 (m, 4 H), 3.57 (m, 2 H), 3.45 (m, 2 H), 3.26 (m, 2 H), 3.15 (s, 3 H); $^{13}$C NMR δ 161.4, 146.2, 140.5, 137.7, 129.2, 127.5, 122.9, 66.8, 59.0, 50.0, 41.7, 36.6, 29.9. Anal. ($C_{14}H_{19}BrN_4O_9S$) C, H, N.

Example 21

(Scheme 2j)

3-[Bis(2-Bromoethyl)Amino]-N-(3-Hydroxypropyl)-2,6-Dinitrobenzamide (IIc-8) and 2-((2-Bromoethyl)-3-{[(3-Hydroxypropyl)Amino]Carbonyl}-2,4-Dinitroanilino)Ethyl Methanesulfonate (IIc-13)

Treatment of 2-(3-{[(3-hydroxypropyl)amino]carbonyl}{2-[(methylsulfonyl)oxy]ethyl}-2,4-dinitroanilino) ethyl methanesulfoneate (27) [for method of preparation see co-pending NZ Application No. 521851] (716 mg, 1.36 mmol) in EtOAc (200 mL) with LiBr (175 mg, 2.0 mmol), followed by chromatography on silica gel and elution with EtOAc/petroleum ether (from 1:1 to 1:0) gave IIc-8 (289 mg, 42%) as a yellow solid; mp (EtOAc/petroleum ether) 142-144° C.; $^1$H NMR [(CD$_3$)$_2$SO] δ 8.75 (t, J=5.8 Hz, 1 H, CONH), 8.23 (d, J=9.4 Hz, 1 H, H-5), 7.62 (d, J=9.4 Hz, 1 H, H-6), 4.47 (m, 1 H, CHOH), 3.68 (m, 4 H), 3.57 (m, 4 H), 3.43 (m, 2 H), 3.20 (m, 2 H), 1.60 (m, 2 H); $^{13}$C NMR δ 161.2, 146.9, 140.2, 137.5, 129.4, 127.7, 122.6, 58.3, 52.6, 36.4, 31.6, 30.1. HRMS (FAB) Calcd. For $C_{14}H_{19}{}^{79}Br_2N_4O_6$ [M+H$^+$] m/z 496.9671. Found: 496.9667.

Further elution with EtOAc/MeOH (50:2) gave IIc-13 (270 mg, 39%): mp. 115-117° C.; $^1$H NMR [(CD$_3$)$_2$SO] δ 8.75 (t, J=5.8 Hz, 1 H, CONH), 8.24 (d, J=9.4 Hz, 1 H, H-5), 7.64 (d, J=9.4 Hz, 1 H, H-6), 4.43 (m, 1 H, CHOH), 4.27 (m, 2 H, CH$_2$OMs), 3.66 (m, 4 H, 2xCH$_2$N), 3.59 (m, 2 H), 3.44 (m, 2 H), 3.22 (m, 2 H), 3.15 (s, 3 H, CH$_3$SO$_3$), 1.60 (m, 2 H); $^{13}$C NMR δ 161.1, 146.2, 140.5, 137.7, 129.2, 127.6, 122.9, 66.8, 58.2, 52.9, 50.0, 36.6, 36.4, 31.6, 30.0. Anal. ($C_{15}H_{21}BrN_4O_9S$) C, H, N.

Example 22

(Scheme 2j)

3-[Bis(2-Bromoethyl)Amino]-N-(4-Hydroxybutyl)-2,6-Dinitrobenzamide (IIc-9) and 2-((2-Bromoethyl)-3-{[(4-Hydroxybutyl)Amino]Carbonyl}-2,4-Dinitroanilino)Ethyl Methanesulfonate (IIc-14)

Treatment of 2-(3-{[(4-hydroxybutyl)amino]carbonyl}{2-[(methylsulfonyl)oxy]ethyl}-2,4-dinitroanilino)ethyl methanesulfonate (28) [for method of preparation see NZ Application No. 521851] (500 mg, 0.92 mmol) in EtOAc (100 mL) with LiBr (110 mg, 1.4 mmol), followed by chromatography on silica gel and elution with EtOAc/petroleum ether (from 1:1 to 1:0) gave IIc-9 (100 mg, 21%) as a foam; $^1$H NMR [(CD$_3$)$_2$SO] δ 8.73 (m, 1 H, CONH), 8.25 (d, J=9.4 Hz, 1 H), 7.63 (d, J=9.4 Hz, 1 H), 4.38 (m, 1 H), 3.69 (m, 4 H), 3.57 (m, 4 H), 3.40 (m, 2 H), 3.14 (m, 2 H), 1.47 (m, 4 H); $^{13}$C NMR δ 161.0, 145.8, 140.2, 137.6, 129.3, 127.6, 122.6, 60.2, 52.6, 30.0, 29.6, 24.8. HRMS (FAB) Calcd. For $C_{15}H_{20}{}^{79}Br_2N_4O_6$ [M+H$^+$] m/z 510.9828. Found: 510.9819.

Further elution with EtOAc/MeOH (50:2) gave IIc-14 (117 mg, 30%): mp. 114-117° C.; $^1$H NMR [(CD$_3$)$_2$SO] δ 8.74 (m, 1 H, CONH), 8.25 (d, J=9.4 Hz, 1 H), 7.65 (d, J=9.4 Hz, 1 H), 4.37 (m, 1 H), 4.27 (m, 2 H), 3.65 (m, 4 H), 3.57 (m, 2 H), 3.35 (m, 2 H), 3.16 (m, 2 H), 3.15 (s, 3 H), 1.47 (m, 4 H); $^{13}$C NMR δ 160.0, 146.1, 140.6, 137.8, 129.2, 127.5, 122.9, 66.8, 60.2, 52.9, 50.0, 36.6, 29.9, 29.6, 24.9. Anal. ($C_{16}H_{23}BrN_4O_9S$) C, H, N.

Example 23

(Scheme 2k)

2-(3-{[(3-Hydroxypropyl)Amino]Carbonyl{}2-[(Methylsulfonyl)Oxy]Ethyl}-2,4-Dinitroanilino) Ethyl Methanesulfonate (27) and 2-((2-Bromoethyl)-3-{[(3-Hydroxypropyl)Amino]Carbonyl}-2,4-Dinitroanilino)Ethyl Methanesulfonate (IIc-13)

Solid IIc-8 (2.15 g, 4.3 mmol) was added to a hot solution of silver methanesulfonate (0.992 g, 4.9 mmol) in dry MeCN (40 mL). The mixture was heated under reflux for 3 h, then cooled and filtered. The solvent was removed at reduced pressure and the residue was separated by chromatography on silica gel, eluting with EtOAc/petroleum ether (from 1:1 to 1:0), to give successively IIc-13 (0.5 g, 25%), IIc-8 (0.3 g, 14%) and 27 (0.4 g, 18%).

Example 24

(Scheme 2k)

2-((2-Chloroethyl)-3-{[(3-Hydroxypropyl)Amino] Carbonyl}-2,4-Dinitroanilino)Ethyl Methanesulfonate (IIc-6)

A solution of 27 (9.0 g, 17.0 mmol) in DMF (110 mL) was treated with LiCl (860 mg, 20.4 mmol) at 60° C. for 2 h, then cooled, poured into dilute HCl, and extracted with EtOAc (3×150 mL). Workup and chromatography of the product on silica gel, eluting with EtOAc/petroleum ether from 1:1 to 1:0, gave IIc-6 (4.0 g, 50%) as yellow crystals: mp 104-109° C.; $^1$H NMR [(CD$_3$)$_2$SO] δ 8.75 (t, J=5.8 Hz, 1 H, CONH), 8.24 (d, J =9.4 Hz, 1 H, H-5), 7.64 (d, J=9.4 Hz, 1 H, H-6), 4.44 (m, 1 H, CHOH), 4.26 (m, 2 H), 3.72 (m, 2 H), 3.65 (m, 2 H), 3.59 (m, 2 H), 3.43 (m, 2 H), 3.20 (m, 2 H), 3.15 (s, 3 H), 1.60 (m, 2 H); $^{13}$C NMR δ 161.1, 146.4, 140.5, 137.7, 129.2, 127.6, 122.9, 66.8, 58.2, 52.9, 50.1, 41.4, 36.6, 36.4, 31.6. Anal. ($C_{15}H_{21}ClN_4O_9S$) C, H, N.

Example 25

(Scheme 2k)

2-((2-Iodoethyl)-3-{[(3-Hydroxypropyl)Amino]Carbonyl}-2,4-Dinitroanilino)Ethyl Methanesulfonate (IIc-15)

A solution of 27 (5.28 g, 10.0 mmol) in EtOAc (250 mL) was treated with NaI (1.8 g, 12.0 mmol) at 60° C. for 2 h, and the product was chromatographed on silica gel, eluting with EtOAc/petroleum ether from 1:2 to 1:0, to give IIc-15 (2.29 g, 41%) as yellow crystals: mp 100-103° C.; $^1$H NMR [(CD$_3$)$_2$SO] δ 10.05 (s, 1 H), 7.40 (d, J=11.5 Hz, 1 H), 7.09 (s, 1 H), 6.70 (d, J=11.5 Hz, 1 H), 2.50 (m, 2 H), 2.21 (m, 2 H), 2.03 (s, 3 H), 1.52 (m, 4 H); $^{13}$C NMR δ 161.1, 145.8, 140.5, 137.7, 129.2, 127.6, 122.9, 66.8, 58.2, 53.9, 49.9, 41.4, 36.6, 36.4, 31.6. Anal. ($C_{15}H_{21}IN_4O_9S$) C, H, N.

Preparation of Phosphates (Scheme 3)

Example 26

2-[[2-[Bis(2-Bromoethyl)Amino]-3,5-Dinitrobenzoyl]Amino]Ethyl Dihydrogen Phosphate (Ib-7P)

A solution of alcohol IIb-7 (2.58 g, 5.33 mmol) and di-tert-butyl diethylphosphoramidite (93%, 2.0 mL, 6.9 mmol) in dry DMF (20 mL) under $N_2$ was treated with 1H-tetrazole (3 wt. % in $CH_3CN$, 55 mL, 18.7 mmol) and stirred at 20° C. for 1.5 h. The reaction mixture was then cooled to −50° C. and a solution of 3-chloroperoxybenzoic acid (55%, 2.68 g, 8.54 mmol) was rapidly added such that the temperature was kept below −5° C. The reaction mixture was warmed to room temperature and diluted with $CH_2Cl_2$ (150 mL). The solution was washed with 5% aqueous $Na_2S_2O_5$ (2×50 mL), 10% aqueous $NaHCO_3$ (2×50 mL), water (2×50 mL), dried, concentrated under reduced pressure below 30° C. and the residue was shaken with i-$Pr_2$O/hexane and refrigerated. The resulting solid was purified by chromatography on silica gel, eluting with $CH_2Cl_2$/EtOAc, followed by recrystallisation from $CH_2Cl_2$/hexane (below 40° C.) to give di-tert-butyl 2-[[2-[bis(2-bromoethyl)amino]-3,5-dinitrobenzoyl]amino] ethyl phosphate (Ib-7E)(2.59 g, 72%) as an unstable yellow solid: mp 99-101° C. (dec); $^1$H NMR [$(CD_3)_2$SO] δ 8.93 (t, J=5.6 Hz, 1 H), 8.76 (d, J=2.8 Hz, 1 H), 8.33 (d, J=2.8 Hz, 1 H), 4.01 (g, J=6.1 Hz, 2 H), 3.62-3.42 (m, 10 H), 1.43 (s, 18 H). HRMS (FAB) calcd for $C_{21}H_{34}^{79}Br_2N_4O_9P$ (MH$^+$) m/z 675.0430 found 675.0398; calcd for $C_{21}H_{34}^{79}Br^{81}BrN_4O_9P$ (MH$^+$) m/z 677.0410, found 677.0397; calcd for $C_{21}H_{34}^{81}Br_2N_4O_9P$ (MH$^+$) m/z 679.0389, found 679.0398. Anal. ($C_{21}H_{33}Br_2N_4O_9P$).

A solution of Ib-7E (2.80 g, 4.14 mmol) and TFA (15 mL) in dry $CH_2Cl_2$ (15 mL) was stirred at 20° C. for 1 h, then concentrated under reduced pressure. Residual TFA was removed azeotropically with $CH_3CN$ (2×) and the resulting residue was dissolved in EtOAc. Addition of excess hexane precipitated a semisolid which was dried under high vacuum at 20° C. to give Ib-7P (98%) as a yellow foam. $^1$H NMR [$(CD_3)_2$SO] δ 8.93 (t, J=5.6 Hz, 1 H), 8.75 (d, J=2.8 Hz, 1 H), 8.36 (d, J=2.8 Hz, 1 H), 3.97 (q, J=6.3 Hz, 2 H), 3.62-3.43 (m, 10 H). HRMS (FAB) calcd for $C_{13}H_{18}^{79}Br_2N_4O_9P$ (MH$^+$) m/z 562.9178, found 562.9171; calcd for $C_{13}H_{18}^{79}Br^{81}BrN_4O_9P$ (MH$^+$) m/z 564.9158, found 564.9152; calcd for $C_{13}H_{18}^{81}Br_2N_4O_9P$ (MH$^+$) m/z 566.9137, found 566.9121. Treatment of diacid Ib-7P with $NaHCO_3$ (2.0 equiv.) gave the disodium salt.

Example 27

3-[[5-[Bis(2-Chloroethyl)Amino]-2,4-Dinitrobenzoyl]Amino]Propyl Dihydrogen Phosphate (Ia-3P)

Similar phosphorylation of IIa-3, followed by chromatography of the product on silica gel and elution with $CH_2Cl_2$/EtOAc (2:3), gave di-tert-butyl 3-[[5-[bis(2-chloroethyl) amino]-2,4-dinitrobenzoyl]amino]propyl phosphate (Ia-3E) (76%) as a yellow solid: mp (EtOAc/i-$Pr_2$O/hexane) 120-121° C. (dec); $^1$H NMR [$(CD_3)_2$SO] δ 8.70 (t, J=5.6 Hz, 1 H), 8.55 (s, 1 H), 7.45 (s, 1 H), 3.96 (q, J=6.7 Hz, 2 H), 3.82 (t, J=5.8 Hz, 4 H), 3.69 (t, J=5.8 Hz, 4 H), 3.34 (after $D_2$O exchange, t, J=6.8 Hz, 2 H), 1.86 (pent, J =6.6 Hz, 2 H), 1.42 (s, 18 H). Anal. ($C_{22}H_{35}Cl_2N_4O_9P$) C, H, N.

Similar treatment of ester Ia-3E with TFA gave diacid Ia-3P (99%) as a hygroscopic yellow solid. $^1$H NMR [$(CD_3)_2$SO] δ 8.71 (t, J=5.6 Hz, 1 H), 8.54 (s, 1 H), 7.45 (s, 1 H), 3.92 (q, J=6.7 Hz, 2 H), 3.82 (t, J=5.8 Hz, 4 H), 3.69 (t, J=5.8 Hz, 4 H), 3.31 (q, J=6.5 Hz, 2 H), 1.84 (pent, J=6.6 Hz, 2 H). HRMS (FAB) Calcd. for $C_{14}H_{20}^{35}Cl_2N_4O_9P$ [M+H]$^+$ m/z 489.0345; found 489.0344. Calcd. for $C_{14}H_{20}^{35}Cl^{37}ClN_4O_9P$ [M+H]$^+$ m/z 491.0316; found 491.0317. Calcd. for $C_{14}H_{20}^{37}Cl_2N_4O_9P$ [M+H]$^+$ m/z 493.0286; found 493.0312. Treatment of diacid I-3P with $NaHCO_3$ (2:0 equiv) gave the disodium salt.

Example 28

3-[[5-[Bis(2-Bromoethyl)Amino]-2,4-Dinitrobenzoyl]Amino]Propyl Dihydrogen Phosphate (Ia-8P)

Similar phosphorylation of IIa-8, followed by chromatography of the product on silica gel and elution with $CH_2Cl_2$/EtOAc (1:1), gave di-tert-butyl 3-[[5-[bis(2-bromoethyl) amino]-2,4-dinitrobenzoyl]amino]propyl phosphate (Ia-8E) (66%) as a yellow solid: mp (EtOAc/i-$Pr_2$O/hexane) 110-111° C. (dec). $^1$H NMR [$(CD_3)_2$SO] δ 8.70 (t, J=5.6 Hz, 1 H), 8.55 (s, 1 H), 7.44 (s, 1 H), 3.96 (q, J=6.7 Hz, 2 H), 3.79-3.63 (m, 84 H), 3.35 (after $D_2$O exchange, t, J=6.8 Hz, 2 H), 1.86 (pent, J=6.6 Hz, 2 H), 1.42 (s, 18 H). Anal. ($C_{22}H_{35}Br_2N_4O_9P$) C, H, N.

Similar treatment of ester Ia-8E with TFA gave diacid Ia-8P (99%) as a hygroscopic yellow solid. $^1$H NMR [$(CD_3)_2$SO] δ 8.71 (t, J=5.6 Hz, 1 H), 8.55 (s, 1 H), 7.43 (s, 1 H), 3.93 (q, J=6.7 Hz, 2 H), 3.79-3.63 (m, 8 H), 3.31 (q, J=6.5 Hz, 2 H), 1.85 (pent, J=6.6 Hz, 2 H). HRMS (FAB) calcd for $C_{14}H_{20}^{79}Br_2N_4O_9P$ (MH$^+$) m/z 576.9335, found 576.9314; calcd for $C_{14}H_{20}^{79}Br^{81}BrN_4O_9P$ (MH$^+$) m/z 578.9314, found 578.9305; calcd for $C_{14}H_{20}^{81}Br_2N_4O_9P$ (MH$^+$) m/z 580.9294, found 580.9297. Treatment of diacid Ia-8P with $NaHCO_3$ (2.0 equiv.) gave the disodium salt.

Example 29

2-[[2-[Bis(2-Chloroethyl)Amino]-3,5-Dinitrobenzoyl]Amino]Ethyl Dihydrogen Phosphate (Ib-2P)

Similar phosphorylation of IIb-2, followed by chromatography of the product on silica gel and elution with $CH_2Cl_2$/EtOAc (13:7), gave di-tert-butyl 2-[[2-[bis(2-chloroethyl) amino]-3,5-dinitrobenzoyl]amino]ethyl phosphate (Ib-2E) (72%) as a yellow solid: mp (EtOAc/i-$Pr_2$O/hexane) 107-108° C. (dec); $^1$H NMR [$(CD_3)_2$SO] δ 8.90 (t, J=5.6 Hz, 1 H), 8.75 (d, J=2.8 Hz, 1 H), 8.33 (d, J=2.8 Hz, 1 H), 4.01 (q, J=6.1 Hz, 2 H), 3.72 (t, J=6.8 Hz, 4 H), 3.53 (q, J=5.5 Hz, 2 H), 3.43 (t, J=6.8 Hz, 4 H), 1.43 (s, 18 H). Anal. ($C_{21}H_{33}Cl_2N_4O_9P$) C, H, N, P. CRL 11363.

Similar treatment of ester Ib-2E with TFA gave diacid Ib-2P (98%) as a yellow foam. $^1$H NMR [$(CD_3)_2$SO] δ 8.89 (t, J=5.6 Hz, 1 H), 8.74 (d, J=2.8 Hz, 1 H), 8.36 (d, J=2.8 Hz, 1 H), 3.98 (q, J=6.2 Hz, 2 H), 3.72 (t, J=6.7 Hz, 4 H), 3.51 (q, J=5.6 Hz, 2 H), 3.43 (t, J=6.7 Hz, 4 H). HRMS (FAB) Calcd. for $C_{13}H_{18}^{35}Cl_2N_2O_9P$ [M+H]$^+$ m/z 475.0189; found 475.0189. Calcd. for $C_{13}H_{18}^{35}Cl^{37}ClN_2O_9P$ [M+H]$^+$ m/z 477.0159; found 477.0167. Calcd. for $C_{13}H_{18}^{35}Cl_2N_2O_9P$ [M+H]$^+$ m/z 479.0130; found 479.0160. Treatment of diacid Ib-2P with $NaHCO_3$ (1.0 equiv.) gave the monosodium salt.

Example 30

2-[(2-Chloroethyl)-2,4-Dinitro-6-[[[2-(Phosphonooxy)Ethyl]amino]-Carbonyl]Anilino]Ethyl Methanesulfonate (Ib-2mP)

Similar phosphorylation of IIb-2m, followed by chromatography of the product on silica gel and elution with EtOAc, gave 2-[(2-chloroethyl)-2-(6-tert-butoxy-8,8-dimethyl-6-oxido-5,7-dioxa-2-aza-6-phosphanon-1-anoyl)-4,6-dinitroanilino]ethyl methanesulfonate (Ib-2mE) (80%) as a yellow foam. $^1$H NMR [(CD$_3$)$_2$SO] δ 8.94 (t, J=5.6 Hz, 1 H), 8.75 (d, J=2.8 Hz, 1 H), 8.34 (d, J=2.8 Hz, 1 H), 4.28 (t, J=5.4 Hz, 2 H), 4.02 (q, j=6.2 Hz, 2 H), 3.74-3.43 (m, 8 H), 3.13 (s, 3 H), 1.43 (s, 18 H). $^{13}$C NMR δ 265.6, 146.2, 145.3, 140.8, 135.6, 127.5, 122.4, 81.7, 67.5, 64.2, 54.3, 51.3, 41.4, 36.5, 29.5.

Similar treatment of ester Ib-2mE with TFA gave diacid Ib-2mP (68%) as a yellow solid. Mp (EtOAc/CH$_2$Cl$_2$): 132-134° C.; $^1$H NMR [(CD$_3$)$_2$SO] δ 8.92 (t, J=5.6 Hz, 1 H), 8.74 (d, J=2.8 Hz, 1 H), 8.37 (d, J=2.8 Hz, 1 H), 4.29 (t, J=5.4 Hz, 2 H), 3.98 (q, J=6.0 Hz, 2 H), 3.58-3.40 (after D$_2$O exchange, m, 8 H), 3.13 (s, 2 H). $^{13}$C NMR δ 165.5, 146.1, 145.3, 140.8, 135.7, 127.6, 122.3, 67.5, 63.3, 63.2, 54.3, 51.3, 41.3, 36.5. Anal. (C$_{14}$H$_{20}$ClN$_4$O$_{12}$PS) C, H, N.

Example 31

2-({2-[Bis(2-Bromopropyl)Amino]-3,5-Dinitrobenzoyl}amino)Ethyl Dihydrogen Phosphate (Ib-7aP)

Similar phosphorylation of alcohol IIb-7a (0.67 g, 1.3 mmol) with di-tert-butyl diethylphosphoramidite (93%, 489 mg, 2.0 mmol), followed by flash column chromatography on silica gel, eluting with EtOAc/petroleum ether (1:1) gave Ib-7aE as a yellow solid (0.74 g, 81%): mp (EtOAc/petroleum ether) 121-123° C.; $^1$H NMR [(CD$_3$)$_2$SO] δ 9.09 (m, 1 H), 8.73 (m, 1 H), 8.32 (m, 1 H), 4.44 (m, 2 H), 4.00 (m, 2 H), 3.39 (m, 2 H), 3.60 (m, 4 H), 1.62 (m, 6 H), 1.44 (s, 18 H). $^{13}$C NMR δ 165.9, 144.8, 143.6, 139.6, 133.2, 128.0, 123.1, 81.6, 64.0, 60.4, 39.9, 29.4, 23.5. Anal. (C$_{23}$H$_{37}$Br$_2$N$_4$O$_9$P) C, H, N.

Similar treatment of Ib-7aE (100 mg) with TFA (6 mL), followed by crystallization from CH$_2$Cl$_2$/EtOAc, gave Ib-7aP as a yellow solid (70 mg, 85%): mp 157-161° C.; $^1$H NMR [(CD$_3$)$_2$SO] δ 9.07 (m, 1 H), 8.72 (m, 1 H), 8.36 (m, 1 H), 4.43 (m, 2 H), 4.00 (m, 2 H), 3.52 (m, 6 H), 1.62 (m, 6 H). $^{13}$C NMR δ 165.9, 144.8, 143.6, 139.7, 133.4, 128.1, 123.1, 63.2, 60.4, 47.9, 39.9, 23.5. Anal. (C$_{15}$H$_{21}$Br$_2$N$_4$O$_9$P) C, H, N.

Example 32

2-[(2-Bromoethyl)-2,4-Dinitro-6-[[[2-(Phosphonooxy)Ethyl]Amino]-Carbonyl]Anilino]Ethyl Methanesulfonate (Ib-12P)

Similar phosphorylation of IIa-12, followed by chromatography of the product on silica gel and elution with EtOAc, gave 2-[(2-bromoethyl)-2-(6-tert-butoxy-8,8-dimethyl-6-oxido-5,7-dioxa-2-aza-6-phosphanon-1-anoyl)-4,6-dinitroanilino]ethyl methanesulfonate (Ib-12E) (66%) as a yellow foam. $^1$H NMR [(CD$_3$)$_2$SO] δ 8.94 (t, J=5.6 Hz, 1 H), 8.75 (d, J=2.8 Hz, 1 H), 8.34 (d, J=2.8 Hz, 1 H), 4.28 (t, J=5.4 Hz, 2 H), 4.02 (q, j=6.2 Hz, 2 H), 3.62-3.43 (m, 8 H), 3.13 (s, 3 H), 1.43 (s, 18 H). HRMS (FAB) calcd for C$_{22}$H$_{37}$$^{79}$BrN$_4$O$_{12}$PS [M+H]$^+$ m/z 693.1029; found 693.1010.

Similar treatment of ester Ib-12E with TFA gave diacid Ib-12P (98%) as a yellow foam. $^1$H NMR [(CD$_3$)$_2$SO] δ 8.92 (t, J=5.6 Hz, 1 H), 8.74 (d, J=2.8 Hz, 1 H), 8.37 (d, J=2.8 Hz, 1 H), 4.28 (t, J=5.4 Hz, 2 H), 3.98 (q, J=6.0 Hz, 2 H), 3.58-3.40 (after D$_2$O exchange, m, 8 H), 3.13 (s, 2 H). HRMS (FAB) calcd for C$_{14}$H$_{21}$$^{79}$BrN$_4$O$_{12}$PS [M+H]$^+$ m/z 578.9798; found 578.9784; calcd for C$_{14}$H$_{21}$$^{81}$Br$^{81}$BrN$_4$O$_{12}$PS [M+H]$^+$ m/z 580.9777; found 580.9784. Treatment of diacid Ib-12P with NaHCO$_3$ (1.0 equiv) gave the monosodium salt.

Example 33

2-[[2-[Bis(2-Iodoethyl)Amino]-3,5-Dinitrobenzoyl]Amino]Ethyl Dihydrogen Phosphate (Ib-14P)

Similar phosphorylation of Ib-14, followed by chromatography of the product on silica gel and elution with CH$_2$Cl$_2$/EtOAc (3:1), gave di-tert-butyl 2-[[2-[bis(2-iodoethyl)amino]-3,5-dinitrobenzoyl]amino]ethyl phosphate (Ib-14E) (67%) as a yellow solid: mp (CH$_2$Cl$_2$/i-Pr$_2$O/hexane) 108-110° C. (dec); $^1$H NMR [(CD$_3$)$_2$SO] δ 8.91 (t, J=5.6 Hz, 1 H), 8.74 (d, J=2.8 Hz, 1 H), 8.30 (d, J=2.8 Hz, 1 H), 4.01 (q, J=6.3 Hz, 2 H), 3.53 (q, J=5.7 Hz, 2 H), 3.45 (t, J7.8 Hz, 4 H), 3.24 (after D$_2$O exchange, t, J=7.6 Hz, 4 H), 1.44 (s, 18 H). Anal. (C$_{21}$H$_{33}$I$_2$N$_4$O$_9$P), C, H, N, P.

Similar treatment of ester Ib-14E with TFA gave diacid Ib-14P (97%) as a yellow foam. $^1$H NMR [(CD$_3$)$_2$SO] δ 8.90 (t, J=5.6 Hz, 1 H), 8.73 (d, J=2.8 Hz, 1 H), 8.34 (d, J=2.8 Hz, 1 H), 3.98 (q, J=6.4 Hz, 2 H), 3.49 (after D$_2$O exchange t, J=5.6 Hz, 2 H), 3.45 (t, J=7.8 Hz, 4 H), 3.29 (t, J=7.7 Hz, 4 H). HRMS (FAB) Calcd. for C$_{13}$H$_{18}$I$_2$N$_4$O$_9$ [M+H]$^+$ m/z 658.3911; found 658.3907. Treatment of diacid Ib-14P with NaHCO$_3$ (2.0 equiv.) gave the disodium salt.

Example 34

2-[(2-Iodoethyl)-2,4-Dinitro-6-({[2-(Phosphonooxy)Ethyl]Amino}Carbonyl)-Anilino]Ethyl Methanesulfonate (Ib-15P)

Similar phosphorylation of alcohol IIb-15 (1.68 g, 3.1 mmol) with di-tert-butyl diethylphosphoramidite (93%, 1.15 g, 4.5 mmol), followed by flash column chromatography on silica gel, eluting with EtOAc/petroleum ether (1:1), and crystallization from EtOAc/petroleum ether, gave Ib-15E as a yellow solid (2.23 g, 97%): mp (EtOAc/petroleum ether) 109-111° C.; $^1$H NMR [(CD$_3$)$_2$SO] δ 8.98 (m, 1 H), 8.76 (d, J=2.8 Hz, 1 H), 8.33 (d, J=2.8 Hz, 1 H), 4.27 (m, 2 H), 4.00 (m, 2 H), 3.53 (m, 2 H), 3.46 (m, 4 H), 3.14 (s, 3 H), 1.43 (s, 18 H). $^{13}$C NMR δ 165.5, 145.6, 145.2, 140.8, 135.6, 127.4, 122.4, 81.7, 67.5, 64.2, 55.4, 50.7, 39.9, 36.5, 29.3, 2.6. Anal. (C$_{22}$H$_{36}$IN$_4$O$_{12}$PS), C, H, N.

Similar treatment of Ib-15E (405 mg) with TFA (6 mL) and crystallization of the product from CH$_2$Cl$_2$/petroleum ether gave diacid Ib-15P as a yellow solid (306 mg, 89%): mp 147-150° C.; $^1$H NMR [(CD$_3$)$_2$SO] δ 8.93 (m, 1 H), 8.74 (d, J=2.8 Hz, 1 H), 8.36 (d, J=2.8 Hz, 1 H), 4.27 (m, 2 H), 4.00 (m, 2 H), 3.46 (m, 6 H), 3.31 (m, 2 H), 3.12 (s, 3 H). $^{13}$C NMR δ 165.5, 145.6, 145.2, 140.8, 135.7, 127.6, 122.3, 67.6, 63.3, 55.5, 50.7, 39.9, 36.5, 2.7. Anal. (C$_{14}$H$_{20}$IN$_4$O$_9$PS), C, H, N.

Example 35

2-[(2-Chloroethyl)-2,4-Dinitro-3-[[[3-(Phosphonooxy)Propyl]Amino]-Carbonyl]Anilino]Ethyl Methanesulfonate (Ic-6P)

Similar phosphorylation of IIc-6, followed by chromatography of the product on silica gel and elution with EtOAc/petroleum ether (from 1:2 to 1:1), gave 2-[(2-chloroethyl)-3-(7-tert-butoxy-9,9-dimethyl-7-oxido-6,8-dioxa-2-aza-7-phosphahex-1-anoyl)-2,4-dinitroanilino]ethyl methanesulfonate (Ic-6E) (98%) as a yellow solid: mp (EtOAc/petroleum ether) 98-102° C. $^1$H NMR [(CD$_3$)$_2$SO] δ 8.83 (t, J=5.6 Hz, 1 H), 8.26 (d, J=9.4 Hz, 1 H), 7.65 (d, J=9.4 Hz, 1 H), 4.29 (t, J=5.3 Hz, 2 H), 3.92 (q, J=6.7 Hz, 2 H), 3.72-3.62 (m, 4 H), 3.62-3.55 (m, 2 H), 3.23 (q, J=6.5 Hz, 2 H), 3.15 (s, 3 H), 1.79 (pent, J=6.7 Hz, 2 H), 1.42 (s, 18 H). $^{13}$C NMR δ 161.3, 146.4, 140.4, 137.6, 129.1, 127.6, 123.0, 81.2, 66.8, 64.1, 64.0, 52.9, 50.1, 41.4, 36.6, 35.9, 29.3. Anal. (C$_{23}$H$_{38}$ClN$_4$O$_{12}$PS) C, H, N.

Similar treatment of ester Ic-6E with TFA gave diacid Ic-6P (84%) as a yellow solid: mp (EtOAc/CH$_2$Cl$_2$) 98-102° C.; $^1$H NMR [(CD$_3$)$_2$SO] δ 8.84 (t, J=5.7 Hz, 1 H), 8.26 (d, J=9.4 Hz, 1 H), 7.65 (d, J=9.4 Hz, 1 H), 4.28 (t, J=5.3 Hz, 2 H), 3.88 (q, J=6.8 Hz, 2 H), 3.72-3.62 (m, 4 H), 3.53 (after D$_2$O exchange, t, J=6.0 Hz, 2 H), 3.23 (q, J=6.6 Hz, 2 H), 3.15 (s, 3 H), 1.76 (pent, J=6.7 Hz, 2 H). Anal. (C$_{15}$H$_{22}$ClN$_4$O$_{12}$PS) C, H, N.

Example 36

3-({3-[Bis(2-Bromoethyl)Amino]-2,6-Dinitrobenzoyl}Amino)Propyl Dihydrogen Phosphate (Ic-8P)

Similar phosphorylation of alcohol IIc-8 (1.41 g, 2.83 mmol) with di-tert-butyl diethylphosphoramidite (93%, 1.25 g, 5.0 mmol), followed by flash column chromatography on silica gel, eluting with EtOAc/petroleum ether (1:1), gave Ic-8E as a yellow solid (1.77 g, 91%): mp (EtOAc/petroleum ether) 112-114° C.; $^1$H NMR [(CD$_3$)$_2$SO] δ 8.86 (m, 1 H), 8.24 (d, J=9.4 Hz, 1 H), 7.63 (d, J=9.4 Hz, 1 H), 3.92 (m, 2 H), 3.70 (m, 4 H), 3.60 (m, 4 H), 3.22 (m, 2 H), 1.78 (m, 2 H), 1.41 (s, 18 H). $^{13}$C NMR δ 161.4, 145.9, 139.9, 137.3, 129.2, 127.8, 122.5, 81.3, 64.1, 52.5, 35.9, 30.1, 29.4. 29.1. Anal. (C$_{22}$H$_{35}$Br$_2$N$_4$O$_9$P), C, H, N.

Similar treatment of Ic-8E (900 mg) with TFA (10 mL) gave diacid Ic-8P as a yellow foam (754 mg, 100%): $^1$H NMR [(CD$_3$)$_2$SO] δ 8.83 (m, 1 H), 8.24 (d, J=9.4 Hz, 1 H), 7.63 (d, J=9.4 Hz, 1 H), 3.86 (m, 2 H), 3.73 (m, 4 H), 3.60 (m, 4 H), 3.22 (m, 2 H), 1.76 (m, 2 H). $^{13}$C NMR δ 161.3, 145.9, 140.1, 137.4, 129.2, 127.6, 122.5, 62.9, 52.5, 36.0, 30.0, 29.3. HRMS (FAB) calcd for C$_{14}$H$_{20}$$^{79}$Br$_2$N$_4$O$_9$P. [M+H]$^+$ m/z 576.9335, found 576.9326.

Example 37

2-[(2-Bromoethyl)-2,4-Dinitro-3-[[[2-(Phosphonooxy)Ethyl]Amino]-Carbonyl]Anilino]Ethyl Methanesulfonate (Ic-12P)

Similar phosphorylation of IIc-12, followed by chromatography of the product on silica gel and elution with EtOAc/petroleum ether (from 1:2 to 1:0), gave (Ic-12E) (99%) as a yellow solid: mp (EtOAc/petroleum ether) 82-86° C. (dec). $^1$H NMR [(CD$_3$)$_2$SO] δ 9.00 (t, J=5.6 Hz, 1 H), 8.26 (d, J=9.4 Hz, 1 H), 7.65 (d, J=9.4 Hz, 1 H), 4.28 (t, J=5.3 Hz, 2 H), 3.92 (q, J=6.7 Hz, 2 H), 3.72-3.62 (m, 4 H), 3.62-3.55 (m, 2 H), 3.23 (q, J=6.5 Hz, 2 H), 3.15 (s, 3 H), 1.42 (s, 18 H). Anal. (C$_{22}$H$_{36}$BrN$_4$O$_{12}$PS) C, H, N.

Similar treatment of ester Ic-12E with TFA gave diacid Ic-12P (100%) as a yellow solid: mp (EtOAc/CH$_2$Cl$_2$) 93-97° C.; $^1$H NMR [(CD$_3$)$_2$SO] δ 8.99 (t, J=5.7 Hz, 1 H), 8.26 (d, J=9.4 Hz, 1 H), 7.65 (d, J=9.4 Hz, 1 H), 4.28 (t, J=5.3 Hz, 2 H), 3.88 (q, J=6.8 Hz, 2 H), 3.72-3.62 (m, 4 H), 3.53 (after D$_2$O exchange, t, J=6.0 Hz, 2 H), 3.23 (q, J=6.6 Hz, 2 H), 3.15 (s, 3 H). Anal. (C$_{14}$H$_{20}$BrN$_4$O$_{12}$PS) C, H, N.

Example 38

2-[(2-Bromoethyl)-2,4-Dinitro-3-[[[3-(Phosphonooxy)Propyl]Amino]-Carbonyl]Anilino]Ethyl Methanesulfonate (Ic-13P)

Similar phosphorylation of IIc-13, followed by chromatography of the product on silica gel and elution with CH$_2$Cl$_2$/EtOAc (1:3), gave 2-[(2-bromoethyl)-3-(7-tert-butoxy-9,9-dimethyl-7-oxido-6,8-dioxa-2-aza-7-phosphahex-1-anoyl)-2,4-dinitroanilino]ethyl methanesulfonate (Ic-13E) (70%) as a yellow solid: mp (CH$_2$Cl$_2$/i-Pr$_2$O) 95-96° C. (dec). $^1$H NMR [(CD$_3$)$_2$SO] δ 8.83 (t, J=5.6 Hz, 1 H), 8.26 (d, J=9.4 Hz, 1 H), 7.65 (d, J=9.4 Hz, 1 H), 4.28 (t, J=5.3 Hz, 2 H), 3.92 (q, J=6.7 Hz, 2 H), 3.72-3.62 (m, 4 H), 3.62-3.55 (m, 2 H), 3.23 (q, J=6.5 Hz, 2 H), 3.15 (s, 3 H), 1.79 (pent, J=6.7 Hz, 2 H), 1.42 (s, 18 H). Anal. (C$_{23}$H$_{38}$BrN$_4$O$_{12}$PS) C, H, N, P.

Similar treatment of ester Ic-13E with TFA gave diacid Ic-13P (98%) as a hygroscopic yellow solid. $^1$H NMR [(CD$_3$)$_2$SO] δ 8.84 (t, J=5.7 Hz, 1 H), 8.26 (d, J=9.4 Hz, 1 H), 7.65 (d, J=9.4 Hz, 1 H), 4.28 (t, J=5.3 Hz, 2 H), 3.88 (q, J=6.8 Hz, 2 H), 3.72-3.62 (m, 4 H), 3.53 (after D$_2$O exchange, t, J=6.0 Hz, 2 H), 3.23 (q, J=6.6 Hz, 2 H), 3.15 (s, 3 H), 1.76 (pent, J=6.7 Hz, 2 H). HRMS (FAB) calcd for C$_{15}$H$_{23}$$^{79}$BrN$_4$O$_{12}$PS [M+H]$^+$ m/z 592.9954; found 592.9956. Treatment of diacid Ic-13P with NaHCO$_3$ (1:0 equiv) gave the monosodium salt.

Example 39

2-[(2-Iodoethyl)-2,4-Dinitro-3-[[[3-(Phosphonooxy)Propyl]Amino]-Carbonyl]Anilino]Ethyl Methanesulfonate (Ic-15P)

Similar phosphorylation of IIc-15, followed by chromatography of the product on silica gel and elution with CH$_2$Cl$_2$/EtOAc (1:3), gave 2-[(2-iodoethyl)-3-(7-tert-butoxy-9,9-dimethyl-7-oxido-6,8-dioxa-2-aza-7-phosphahex-1-anoyl)-2,4-dinitroanilino]ethyl methanesulfonate (Ic-15E) (58%) as a yellow solid: mp (EtOAc/iPr$_2$O) 90-100° C. $^1$H NMR [(CD$_3$)$_2$SO] δ 8.86 (t, J=5.6 Hz, 1 H), 8.25 (d, J=9.4 Hz, 1 H), 7.63 (d, J=9.5 Hz, 1 H), 4.27 (t, J=5.2 Hz, 2 H), 3.91 (q, J=6.7 Hz, 2 H), 3.67 (t, J=5.2 Hz, 2 H), 3.60 (t, J=7.1 Hz, 2 H), 3.26-3.17 (after D$_2$O exchange, m, partially obscured, 2 H), 3.23 (q, J=6.5 Hz, 2 H), 3.15 (s, 3 H), 1.78 (pent, J=6.6 Hz, 2 H). Anal. (C$_{23}$H$_{38}$IN$_4$O$_{12}$PS) C, H, N, P.

Similar treatment of ester Ic-15E with TFA gave diacid Ic-15P (97%) as a hygroscopic yellow solid: mp (CH$_3$CN/EtOAc) 84-86° C. $^1$H NMR [(CD$_3$)$_2$SO] δ 8.90 (t, J=5.6 Hz, 1 H), 8.24 (d, J=9.4 Hz, 1 H), 7.57 (d, J=9.5 Hz, 1 H), 4.25 (t, J=5.2 Hz, 2 H), 3.81 (after D$_2$O exchange, q, J=6.7 Hz, 2 H), 3.62 (after D$_2$O exchange, t, J=5.2 Hz, 2 H), 3.56 (t, J=7.1 Hz, 2 H), 3.26 (t, J=6.9 Hz, 2 H), 3.20 (q, J=6.5 Hz, 2 H), 3.09 (s, 3 H), 1.73 (pent, J=6.6 Hz, 2 H). HRMS(FAB) calcd for C$_{15}$H$_{22}$IN$_4$O$_{12}$PS (MH$^+$) m/z 640.9816. Found; 640.9795. Anal. (C$_{15}$H$_{22}$IN$_4$O$_{12}$PS) C, H.

TABLE 2

Combustion analysis data for new compounds of Tables 1a and 1b

| No | Found C | H | N | other | Calculated C | H | N | other |
|---|---|---|---|---|---|---|---|---|
| IIa-1 | 44.5 | 3.9 | 18.6 | | 44.6 | 4.1 | 18.9 | |
| IIa-3 | 41.3 | 4.3 | 13.7 | 17.4 (Cl) | 41.1 | 4.4 | 13.7 | 17.3 (Cl) |
| IIa-7 | 32.6 | 3.3 | 11.6 | 33.3 (Br) | 32.3 | 3.3 | 11.6 | 33.0 (Br) |
| IIa-7s | 33.4 | 3.7 | 7.8 | | 32.5 | 3.7 | 8.1 | |
| IIa-8 | 33.9 | 3.6 | 11.4 | 32.1 (Br) | 33.8 | 3.6 | 11.3 | 32.1 (Br) |
| IIa-9 | 35.5 | 3.8 | 10.7 | 31.2 (Br) | 35.2 | 3.9 | 10.9 | 31.2 (Br) |
| IIa-14 | 27.3 | 2.6 | 9.6 | 43.8 (I) | 27.0 | 2.8 | 9.7 | 43.9 (I) |
| IIb-1 | 51.2 | 5.7 | 15.9 | | 51.3 | 5.7 | 15.9 | |
| IIb-3 | 41.6 | 4.5 | 13.6 | 17.1 (Cl) | 41.1 | 4.4 | 13.7 | 17.3 (Cl) |
| IIb-7 | 32.9 | 3.3 | 11.5 | 33.3 (Br) | 32.3 | 3.3 | 11.6 | 33.0 (Br) |
| IIb-7a | 35.3 | 3.8 | 10.9 | | 35.2 | 3.9 | 10.9 | |
| IIb-8 | 34.9 | 3.7 | 11.3 | 32.3 (Br) | 33.8 | 3.6 | 11.3 | 33.3 (Br) |
| IIb-14 | 27.8 | 3.1 | 9.5 | | 27.0 | 2.8 | 9.7 | |
| IIc-12 | 33.8 | 3.7 | 11.0 | | 33.7 | 3.8 | 11.2 | |
| IIc-13 | 35.4 | 3.9 | 11.0 | | 35.2 | 4.1 | 10.9 | |
| IIc-14 | 36.7 | 4.5 | 10.2 | | 36.4 | 4.4 | 10.6 | |
| Ib-7E | 37.7 | 4.9 | 8.3 | 4.6 (P) | 37.3 | 4.9 | 8.3 | 4.6 (P) |
| Ib-2E | 44.8 | 6.2 | 9.0 | 5.1 (P) | | | | |
| Ib-14E | 32.9 | 4.2 | 7.2 | 3.8 (P) | 32.7 | 4.3 | 7.3 | 4.0 (P) |
| Ia-3E | 44.2 | 5.9 | 9.3 | | 43.9 | 5.9 | 9.3 | |
| Ia-8E | 38.5 | 5.0 | 8.2 | | 38.3 | 5.1 | 8.1 | |
| Ic-13E | 39.0 | 5.4 | 8.9 | 4.4 (P) | 39.2 | 5.4 | 7.9 | 4.4 (P) |
| Ic-15E | 37.0 | 5.0 | 7.3 | 4.2 (P) | 36.7 | 5.1 | 7.5 | 4.1 (P) |
| Ic-15P | 28.1 | 3.5 | | | 28.3 | 3.5 | | |

Representative alcohols of Formula (I) (listed in Table 1a) show selective cytotoxicity towards human cancer cell lines transfected with either the E. coli nitroreductase cDNA (NTR) (Table 3, columns 2 and 3), or human cytochrome P450 reductase (P450R) under hypoxic conditions (Table 3, columns 4 and 5). In this table, sensitivity ratios are displayed to indicate the degree of selectivity for either NTR expression (column 3) or hypoxia (column 5). However, overexpression of P450R is not required for hypoxic selectivity.

$IC_{50}$ values are derived from cell proliferation experiments, following 4 hour drug exposure under a gas phase of either 20% oxygen or 0% oxygen (anoxia, achieved using an anaerobic chamber). Cells were grown under aerobic conditions for a further 5 days, and cell density estimated using the sulphorhodamine B assay, to determine the concentration of prodrug required to inhibit growth to 50% of control.

TABLE 3

Selective cytotoxicities of representative examples of the alcohols of Table 1a

| | Human colon (4 h) | | A549 | Human lung (4 h) A549 |
|---|---|---|---|---|
| No | WiDr (NTR$^{+ve}$) IC$_{50}$ (μM) | WiDr WT:NTR IC$_{50}$ Ratio | (P450R$^{+ve}$) anoxia IC$_{50}$ (μM) | (P450R$^{+ve}$) 20% O$_2$/anoxia IC$_{50}$ Ratio |
| IIa-1 | 5.2 | 34 | 3.7 | 28 |
| IIa-2 | 48 | 26 | 25 | 3.7 |
| IIa-3 | 47 | 36 | 54 | 23 |
| IIa-7 | 1.5 | 99 | 6.7 | 49 |
| IIa-7s | 9.3 | 35 | 2.1 | 109 |
| IIa-8 | 1.6 | 224 | 23 | 6.6 |
| IIa-9 | 6.4 | 58 | 22 | 9.4 |
| IIa-10 | 10 | 22 | — | — |
| IIa-11 | 11 | 9 | — | — |
| IIa-12 | 4.2 | 116 | 73 | 10 |
| IIa-13 | 5 | 90 | 32 | 18 |
| IIa-14 | 2.9 | 49 | 13 | 4.5 |
| IIb-1 | 61 | 2 | 384 | <1.3 |
| IIb-2 | 11.8 | 47 | 18 | 20 |
| IIb-3 | 13.6 | 59 | 30 | 9 |
| IIb-4 | 14 | 18 | — | — |
| IIb-5 | 13 | 19 | — | — |
| IIb-6 | 27 | 5 | — | — |
| IIb-7 | 0.3 | 61 | 0.8 | 56 |
| IIb-7a | 0.5 | 27 | 1.0 | 5.3 |
| IIb-8 | 0.4 | 13 | 1.1 | 24 |
| IIb-9 | 0.9 | 5 | 1.4 | 20 |
| IIb-10 | 0.9 | 2 | 2.3 | 11 |
| IIb-11 | 1.0 | 2 | 6.6 | 4.5 |
| IIb-12 | 0.4 | 48 | 0.28 | 133 |
| IIb-13 | 0.3 | 27 | 0.15 | 138 |
| IIb-14 | 0.8 | 12 | 1.0 | 27 |
| IIb-15 | 0.3 | 31 | 0.28 | 118 |
| IIc-7 | 10 | 46 | 3.9 | 40 |
| IIc-8 | 5.0 | 70 | 6.6 | 24 |
| IIc-9 | 31 | 6 | 7.3 | 21 |
| IIc-12 | 5.0 | 84 | 2.6 | 173 |
| IIc-13 | 4.3 | 95 | 4.5 | 134 |
| IIc-14 | 20 | 16 | 7.1 | 57 |

Figure 1A:
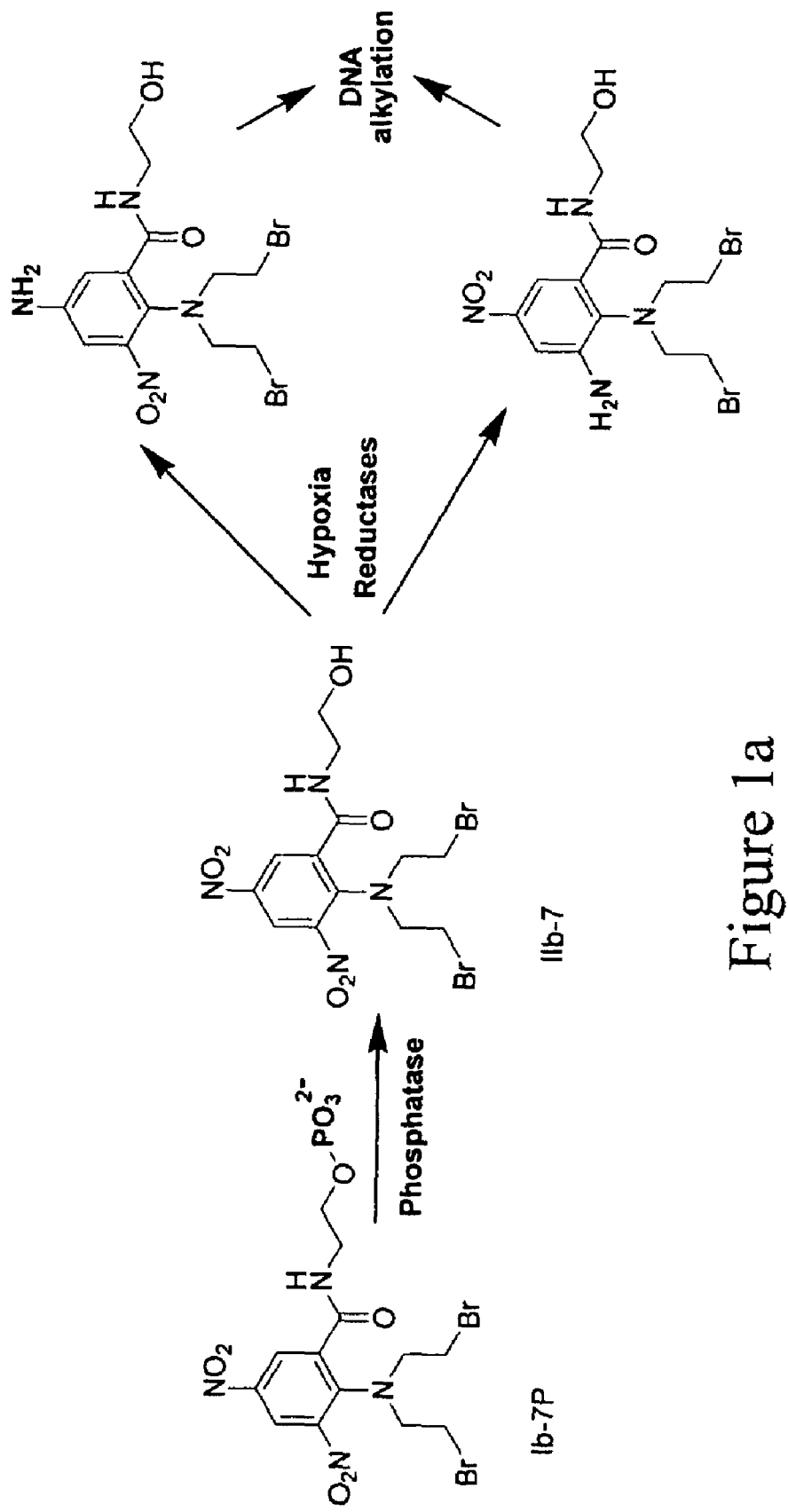
FIG. 1a depicts in vivo activity of compound IIb-7 and its corresponding phosphate pre-prodrug Ib-7P, relative to the known hypoxic cytotoxin tirapazamine.
Figure 1B:
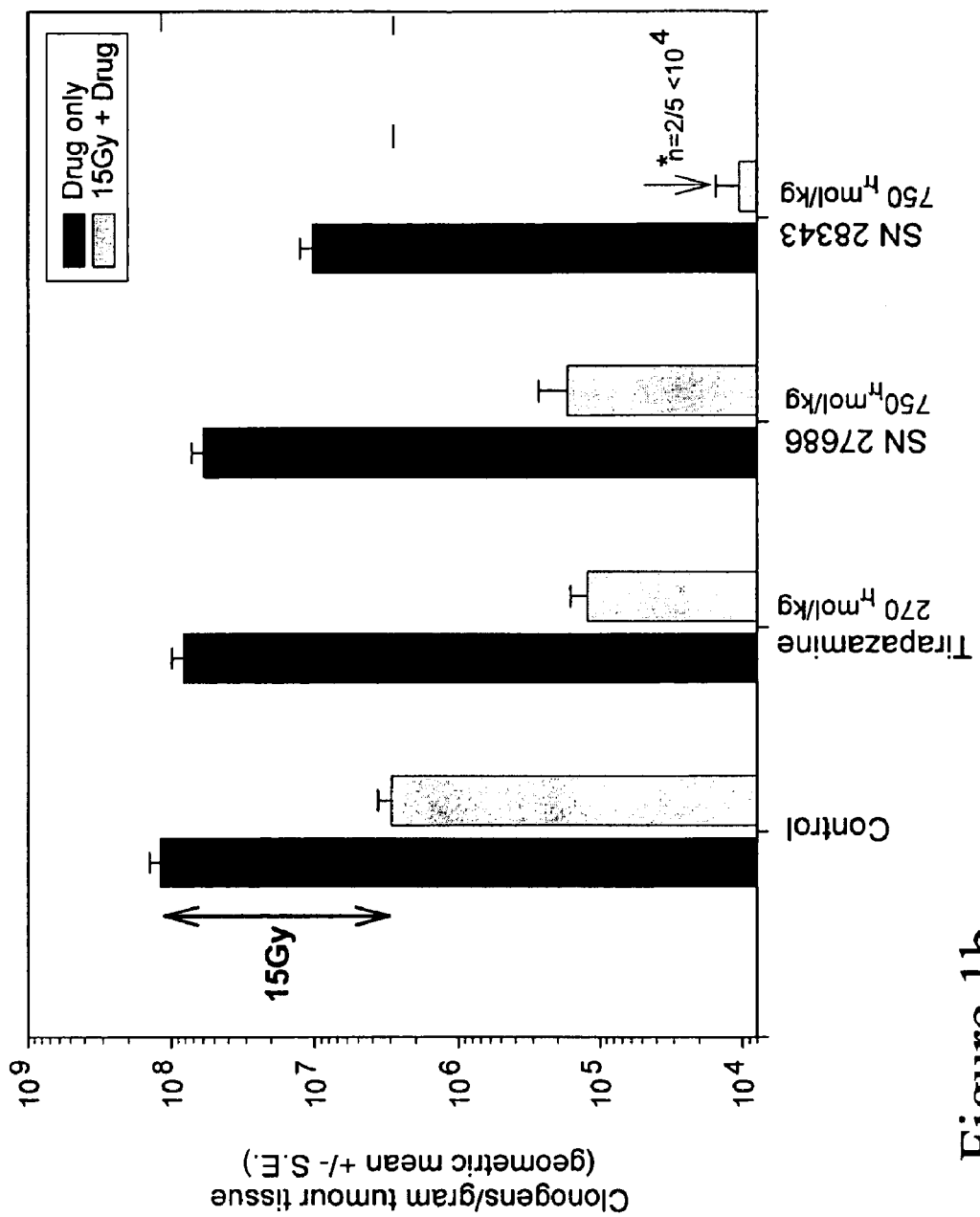
FIG. 1b depicts an excision assay method: 300-500 mg Rif-1 xenograft→ 15 Gy→ Single prodrug dose @ MTD→ 18 hr→ excision→ disaggregate→ plate 10$^2$-10$^5$ cells→ 12 days→ colonies counted.

The activity of the phosphates as hypoxic cytotoxins is demonstrated by the data in FIG. 1 for the representative example (Ib-7P). This employs an in vivo excision assay with the Rif-1 tumour, where the oxic tumour cells are sterilised using 15 Gy of radiation, and the cytotoxicity of an agent against the remaining hypoxic cells can be quantitated. Unexpectedly, the activity of the phosphate Ib-7P is found to exceed that of its parent alcohol (IIb-7) at their respective maximum tolerated doses (Ib-7P=750 µmol/kg; IIb-7=1000 µmol/kg). This experiment demonstrates that the phosphate Ib-7P is more active against hypoxic cells than the reference hypoxic cytotoxin tirapazamine, and that it is more active against hypoxic cells than oxic cells (i.e. when given post irradiation than when given without irradiation). Thus Ib-7P acts as a hypoxia-selective cytotoxin in vivo. Although less active against oxic tumour cells, this activity is significant demonstrating that the compound also has utility as a single agent (without radiation).

The notable activity of the phosphates of Formula (I) against hypoxic cells in human tumour xenografts is illustrated by the data of Table 4. In these experiments SiHa human cervical carcinoma cells were grown subcutaneously in CD-1 nude (immunodeficient) mice. The compounds were administered at doses corresponding to 75% or 20% of the maximum tolerated dose (MTD), 5 minutes after a whole body dose of ionising radiation (cobalt-60 gamma radiation) sufficient to sterilise the oxic cells (15 Gy). The tumours were excised 18 hours later, dissociated with a cocktail of proteases, and cell survival was determined using a clonogenic assay. The logarithms of cell kill were calculated from the difference in the numbers of clonogens per gram tumour tissue between treated and control tumours. All of the phosphates tested showed large effects against hypoxic cells at 75% of the MTD (Table 4, column 4). This was selective for hypoxia as demonstrated by the lesser cell kill in the absence of radiation. However, cell killing by the compounds alone was significant in all cases (Table 4, column 5) demonstrating that the compounds also have antitumour activity as single agents. Activity against hypoxic cells was also demonstrated for the same compounds at doses corresponding to only 20% of the MTD (Table 4, column 7). The reference hypoxic cytotoxin tirapazamine, and the reference nitrogen mustards (melphalan, chlorambucil and cyclophosphamide) lacked activity at 20% of their respective MTDs.

Figure 2A:
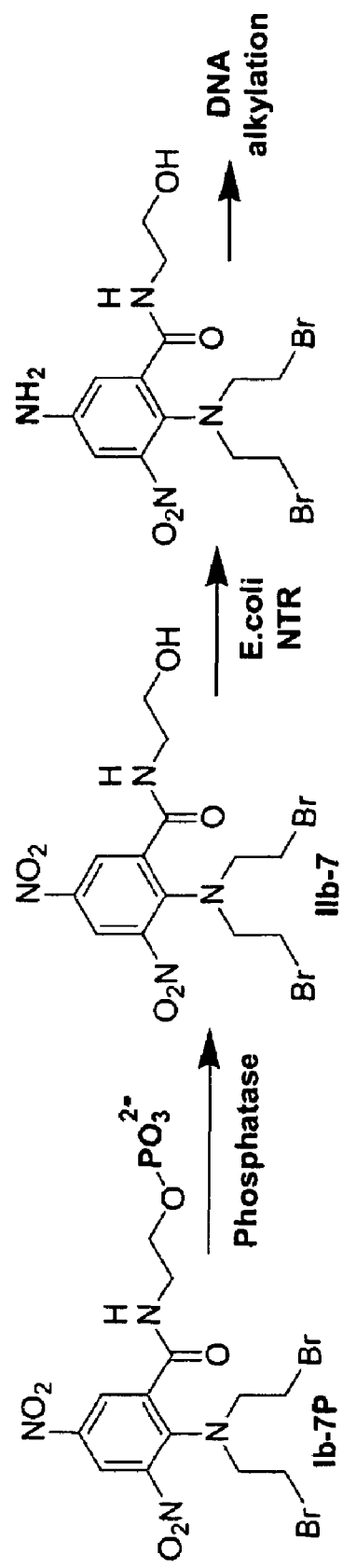
FIG. 2a depicts in vivo activity of compound IIb-7 and its corresponding phosphate pre-prodrug, Ib-7P, against human colon carcinoma xenografts grown by inoculating mixtures of 90% NTR−ve and 10% NTR+ve Wi Dr cells.
Figure 2B:
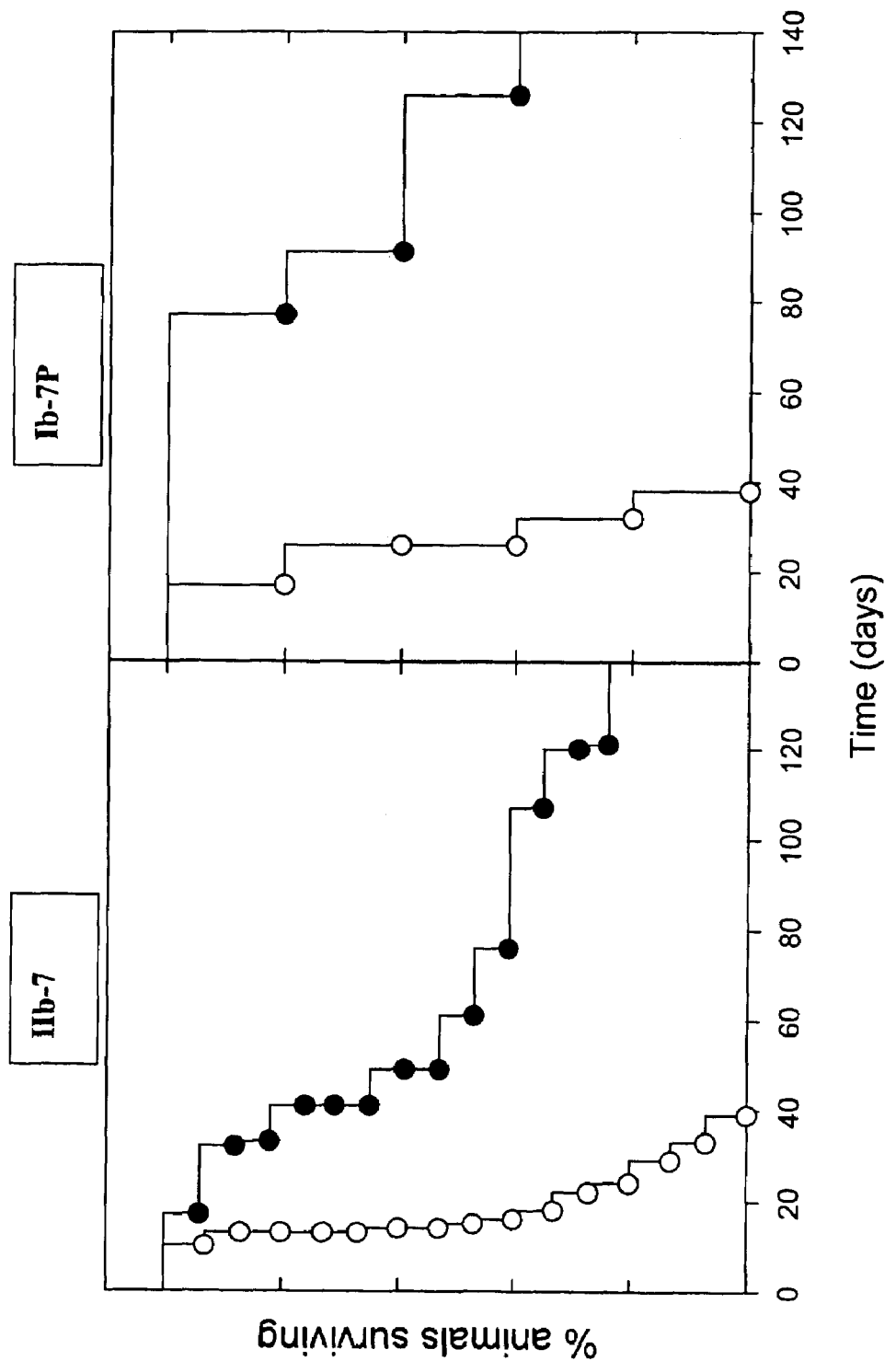
FIG. 2b are plots of % animals survival versus time (days), in which open circles denote wild-type WiDR human colon carcinoma xenografts, and filled circles denote tumours containing WiDr cells transfected with the E. coli NTR gene.
Figure 3A:
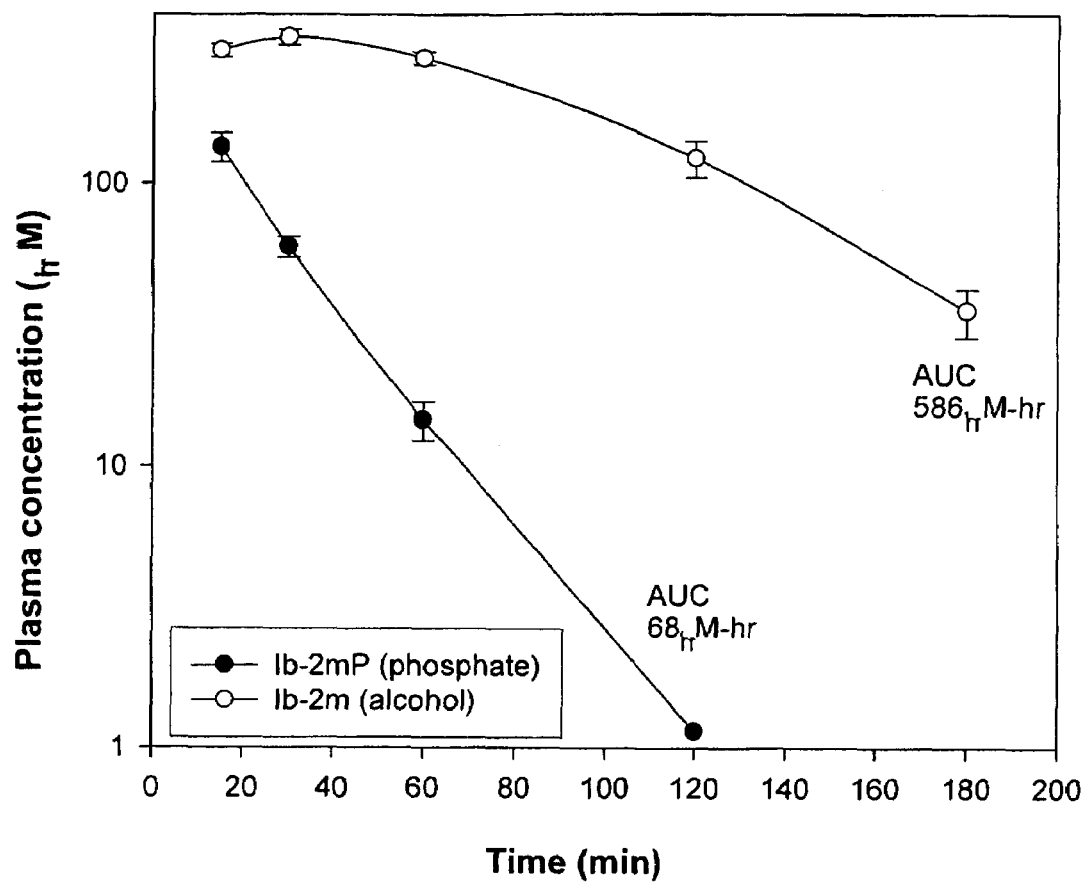
FIG. 3a is a plot of plasma concentration versus time (min) for compound Ib-2mP in female CD-1 mice.
Figure 3B:
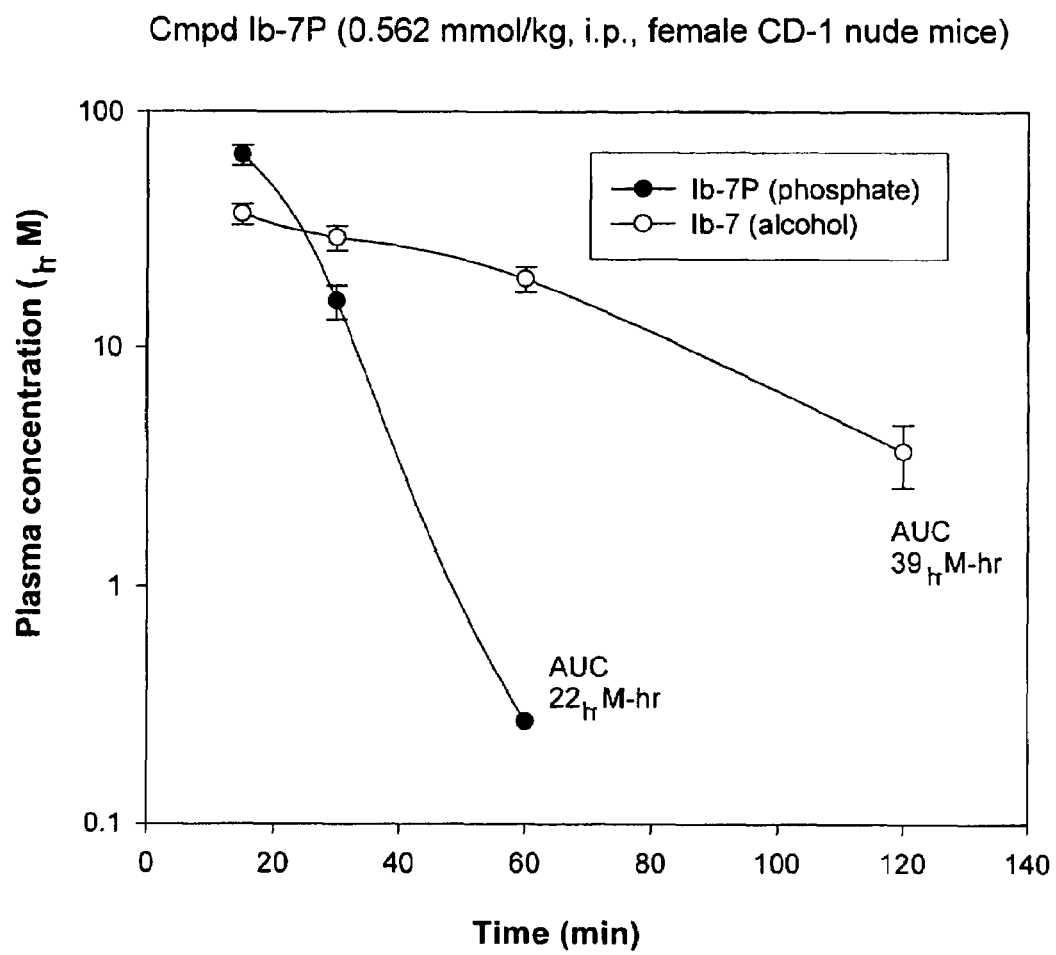
FIG. 3b is a plot of plasma concentration versus time (min) for compound Ib-7P in female CD-1 mice.
Figure 3C:
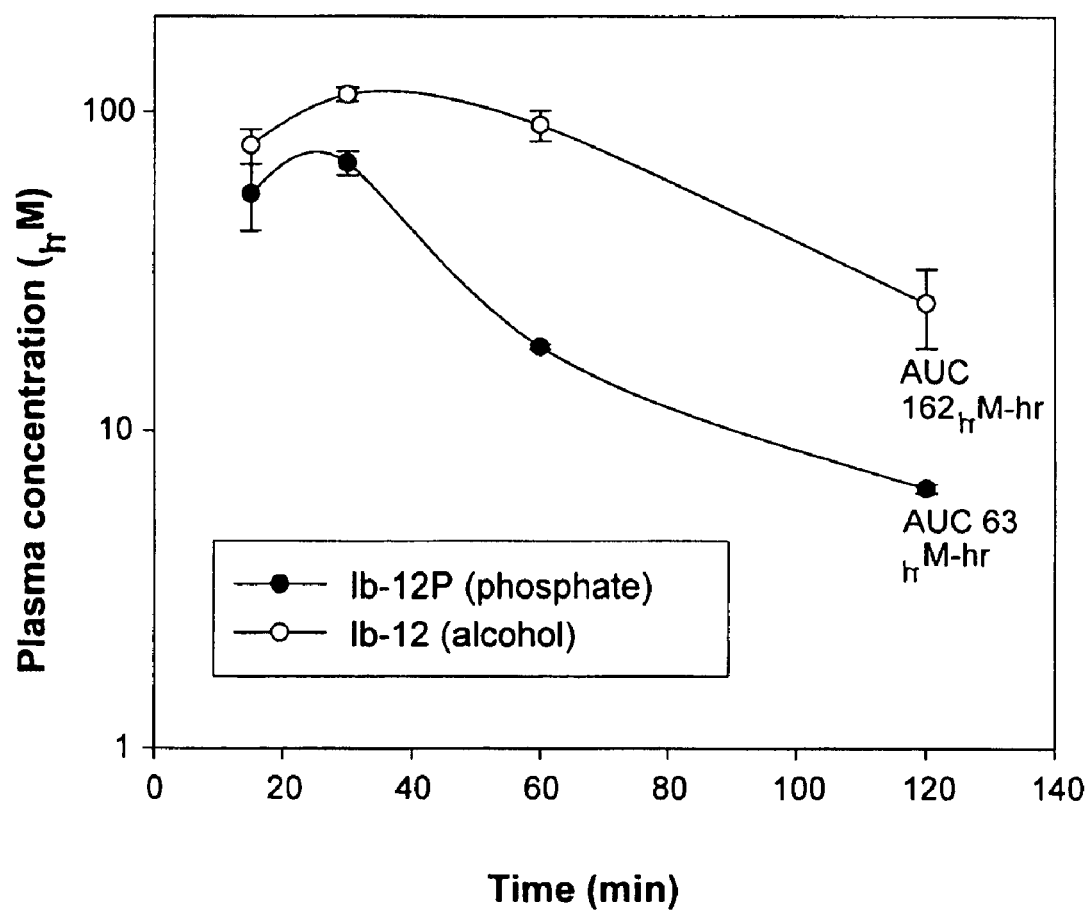
FIG. 3c is a plot of plasma concentration versus time (min) for compound Ib-12P in female CD-1 mice.
Figure 3D:
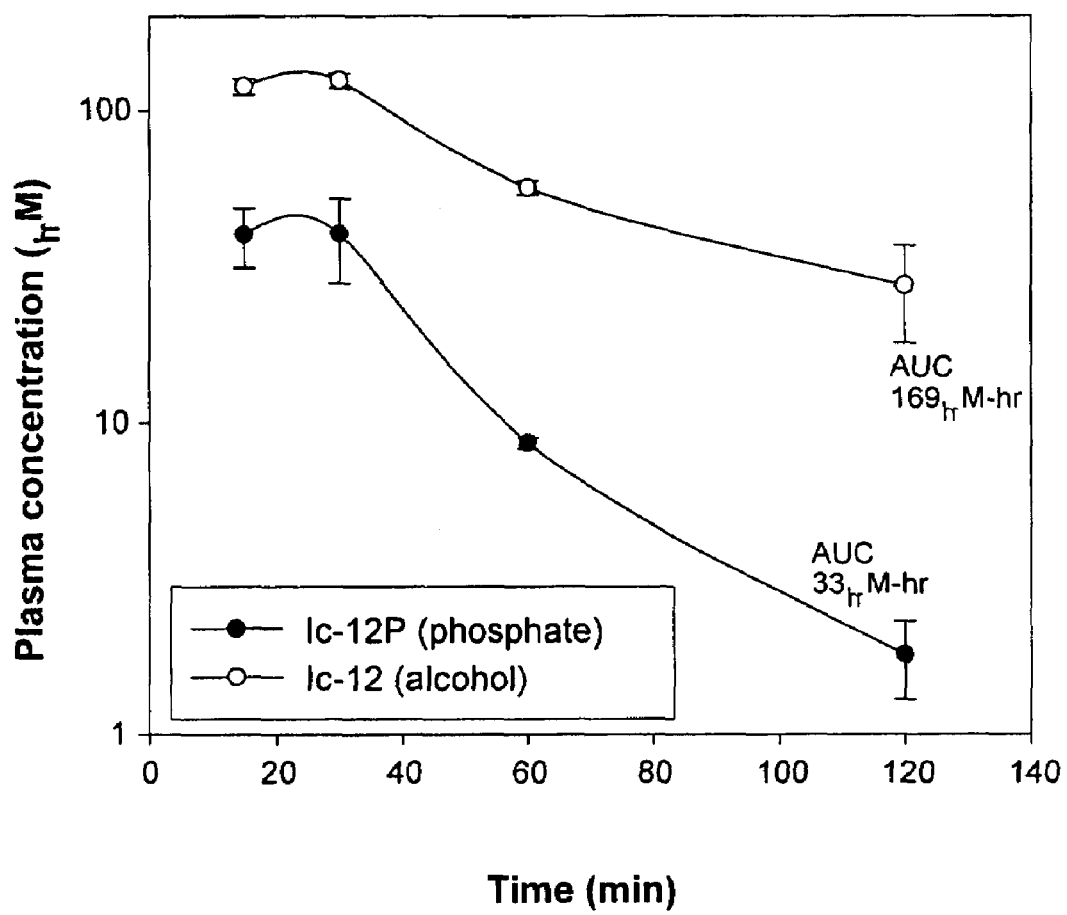
FIG. 3d is a plot of plasma concentration versus time (min) for compound Ic-12P in female CD-1 mice.

A representative example of the phosphates of Formula (I) as NTR activated cytotoxins is provided in FIG. 2. In the WiDr in vivo growth delay assay, xenografts containing mixtures of WiDr$^{WT}$ and WiDr$^{NTR}$ cells are grown to 300 mm$^3$ and treated with a single dose of prodrug at its MTD. Tumour growth is monitored over time and animals are euthanased when mean tumour volume >1600 mm$^3$. Data is presented as time to death. Unexpectedly, the activity of the phosphate (Ib-7P) is observed to exceed that of its parent alcohol (IIb-7), when administered at their respective maximum tolerated doses (750 µmol/kg). Ib-7P is superior to IIb-7 with respect to (i) time to first treatment failure (77-days vs. 17-days) and (ii) over-all survival (40% vs. 6%).

Pharmocokinetics of the phosphate esters Ib-2mP, Ib-7P, Ib-12P and Ic-12P following administration to female CD-1 nude mice by intraperitoneal injection at a dose corresponding to 75% of the maximum tolerated dose. Monosodium salts of the compounds were dissolved in phosphate buffered saline, pH 7.4, with addition of one equivalent of sodium bicarbonate. Serial blood samples were obtained by small tail vein bleeds, and 10 ul of plasma was prepared from each. Proteins were precipitated by addition of 3 volumes of methanol, and concentrations of the phosphate esters and corresponding alcohols were determined by HPLC using either UV or mass spectrometry detection.

The data shows that the phosphate esters are converted efficiently to the corresponding alcohols in mice. The alcohols are the species activated by nitroreduction in hypoxic, or NTR-expressing, cells.

Wherein the foregoing description reference has been made to reagents, or integers having known equivalents thereof, then those equivalents are herein incorporated as if individually set forth.

While this invention has been described with reference to certain embodiments and examples, it is to be appreciated that

TABLE 4

Activity of phosphates of Formula (I) against oxic and hypoxic cells in SiHa human tumour xenografts in nude mice. Compounds were administered as single i.p. doses in saline.

| | | 75% of MTD | | | 20% of MTD | |
|---|---|---|---|---|---|---|
| No | MTD (µmol/kg) | Dose (µmol/kg) | Log kill, cmpd only[a] Mean ± sem | Log kill, cmpd after radiation[b] | Dose (µmol/kg) | Log kill, cmpd after radiation[b] |
| Ia-8P | 1000 | 750 | ND[c] | ND | 200 | −0.01 ± 0.19 |
| Ib-2P | 237 | 178 | ND | ND | 47 | −0.10 ± 0.08 |
| Ib-2mP | 1780 | 1330 | 2.47 ± 0.08 | ≧3.47 ± 0.17 | 356 | 2.56 ± 0.37 |
| Ib-7P | 750 | 562 | 1.20 ± 0.07 | 2.35 ± 0.17 | 150 | 1.12 ± 0.13 |
| Ib-12P | 1330 | 1000 | 1.32 ± 0.30 | ≧3.38 ± 0.28 | 267 | 1.65 ± 0.19 |
| Ib-14P | 562 | 422 | 0.92 ± 0.06 | 1.93 ± 0.21 | 113 | 0.64 ± 0.11 |
| Ib-15P | 1330 | 1000 | 2.24 ± 0.15 | ≧3.27 ± 0.13 | 267 | 1.74 ± 0.23 |
| Ic-6P | 3160 | 2370 | 1.11 ± 0.20 | ≧2.62 ± 0.17 | 632 | 1.64 ± 0.30 |
| Ic-8P | 562 | 422 | ND | ND | 113 | 0.72 ± 0.08 |
| Ic-12P | 1780 | 1330 | 1.04 ± 0.29 | ≧2.96 ± 0.31 | 356 | 2.03 ± 0.25 |
| Ic-13P | 3160 | 2370 | 2.36 ± 0.28 | ≧3.23 ± 0.08 | 632 | 1.60 ± 0.20 |
| Ic-15P | 1780 | 1333 | 2.27 ± 0.17 | 2.80 ± 0.40 | 356 | 1.81 ± 0.23 |
| Tirapazamine | 316 | 237 | −0.02 ± 0.01 | 0.66 ± 0.11 | 63 | −0.01 ± 0.09 |
| Chlorambucil | 237 | 178 | 0.11 ± 0.04 | 0.31 ± 0.10 | 47 | 0.18 ± 0.13 |
| Melphalan | 42.2 | 31.6 | ND | ND | 8.4 | 0.04 ± 0.05 |
| Cyclophosphamide | 750 | 562 | ND | ND | 150 | 0.07 ± 0.10 |

[a]Relative to controls, in the same experiment, treated with vehicle (saline) only. Log kill = log$_{10}$ (clonogens/g tumour for control tumours) − log$_{10}$(clonogens/g tumour for treated tumours).
[b]Relative to the mean for radiation only, in the same experiment. Log kill = log$_{10}$(clonogens/g tumour for radiation alone) − log$_{10}$(clonogens/g tumour for tumours treated with radiation plus compound).
[c]None detected

The invention claimed is:

1. A phosphate compound of Formula (I)

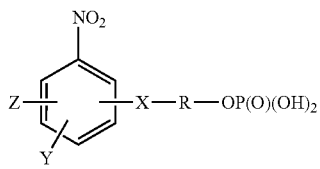

wherein:

X represents at any available ring position —CONH—, —SO$_2$NH—, —O—, —CH$_2$—, —NHCO— or —NHSO$_2$—;

R represents a lower C$_{1-6}$ alkyl optionally substituted with one or more groups selected from hydroxy, amino and N-oxides therefrom or dialkylamino and N-oxides therefrom;

Y represents at any available ring position —N-aziridinyl, —N(CH$_2$CH$_2$W)$_2$ or —N(CH$_2$CHMeW)$_2$, where each W is independently selected from halogen or —OSO$_2$Me;

Z represents at any available ring position —NO$_2$, -halogen, —CN, —CF$_3$ or —SO$_2$Me; and pharmaceutically acceptable salts thereof.

2. A phosphate compound of Formula (I) as claimed in claim 1 which is selected from a compound represented by formulae (Ia), (Ib) or (Ic)

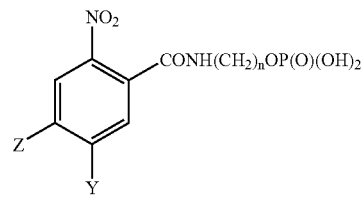

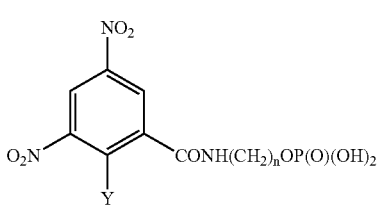

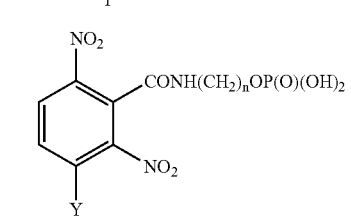

wherein Y represents

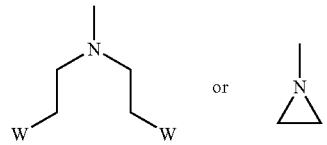

and wherein
n represents 1 to 6
Z represents —NO$_2$, -halogen, —CN, —CF$_3$ or —SO$_2$Me; and
where each W is independently selected from halogen or —OSO$_2$Me
and pharmaceutically acceptable salts thereof.

3. The phosphate compound of Formula (I) as claimed in claim 1 which is selected from:

2-[[2-[Bis(2-bromoethyl)amino]-3,5-dinitrobenzoyl]amino] ethyl dihydrogen phosphate;

3-[[5-[Bis(2-chloroethyl)amino]-2,4-dinitrobenzoyl]amino]propyl dihydrogen phosphate;

3-[[5-[Bis(2-bromoethyl)amino]-2,4-dinitrobenzoyl]amino]propyl dihydrogen phosphate;

2-[[2-[Bis(2-chloroethyl)amino]-3,5-dinitrobenzoyl]amino]ethyl dihydrogen phosphate;

2-[(2-Chloroethyl)-2,4-dinitro-6-[[[2-(phosphonooxy)ethyl]amino-carbonyl]anilino]ethyl methanesulfonate;

2-({2-[Bis(2-bromopropyl)amino]-3,5-dinitrobenzoyl}amino)ethyl dihydrogen phosphate;

2-[(2-Bromoethyl)-2,4-dintro-6-[[[2-(phosphonooxy)ethyl]amino]-carbonyl]anilino]ethyl methanesulfonate;

2-[[2-[Bis(2-iodoethyl)amino]-3,5-dinitrobenzoyl]amino]ethyl dihydrogen phosphate;

2-[(2-iodoethyl)-2,4-dinitro-6-({[2-phosphonooxy)ethyl]amino}carbonyl)-anilino]ethyl methanesulfonate;

2-[(2-Chloroethyl)-2,4-dinitro-3-[[[3-(phosphonooxy)propyl]amino]-carbonyl]anilino]ethyl methanesulfonate;

3-({3-[Bis(2-bromoethyl)amino]-2,6-dinitrobenzoyl}amino)propyl dihydrogen phosphate;

2-[(2-Bromoethyl)-2,4-dinitro-3-[[[2-(phosphonooxy)ethyl]amino]-carbonyl]anilino]ethyl methanesulfonate;

2-[(2-Bromoethyl)-2,4-dinitro-3-[[[3-(phosphonooxy)propyl]amino]-carbonyl]anilino]ethyl methanesulfonate; and 2-[(2-iodoethyl)-2,4-dinitro-3-[[[3-(phosphonooxy)propyl]amino]-carbonyl]anilino]ethyl methanesulfonate.

4. A method of preparing a phosphate represented by the general formula (I);

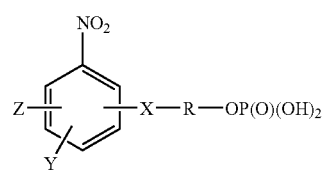

wherein:
X represents at any available ring position —CONH—, —SO$_2$NH—, —O—, —CH$_2$—, —NHCO— or —NHSO$_2$—;

R represents a lower $C_{1-6}$ alkyl optionally substituted with one or more groups including hydroxy, amino and N-oxides therefrom or dialkylamino and N-oxides therefrom;

Y represents at any available ring position —N-aziridinyl or —N(CH$_2$CH$_2$W)$_2$, where each W is independently selected from halogen or —OSO$_2$Me;

Z represents at any available ring position —NO$_2$, -halogen, —CN, —CF$_3$ or —SO$_2$Me;

and pharmaceutically acceptable salts thereof:

the method comprising the step of
(i) phosphorylating a compound of formula (II)

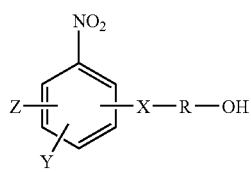
(II)

wherein:

X represents at any available ring position —CONH—, —SO$_2$NH—, —O—, —CH$_2$—, —NHCO— or —NHSO$_2$—;

Y represents at any available ring position —N-aziridinyl, —N(CH$_2$CH$_2$W)$_2$, or —N(CH$_2$CH MeW)$_2$ where each W is independently selected from halogen or —OSO$_2$Me;

Z represents at any available ring position —NO$_2$, -halogen, —CN, —CF$_3$ or —SO$_2$Me; and R represents a lower $C_{1-6}$ alkyl optionally substituted with one or more groups including hydroxy, amino and N-oxides therefrom or dialkylamino and N-oxides therefrom.

5. A method of preparing a compound of formulae (Ia), (Ib) or (Ic)

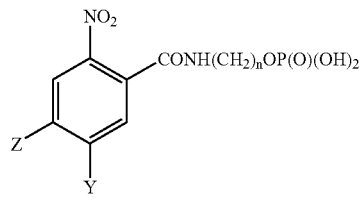
(Ia)

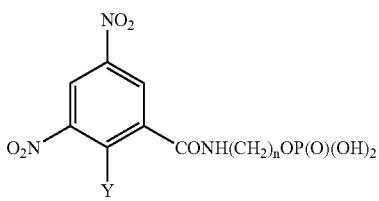
(Ib)

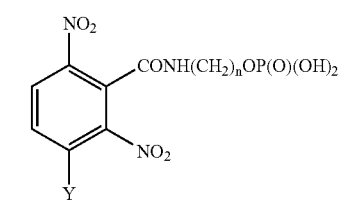
(Ic)

wherein Y may represent

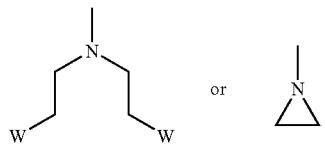

and wherein n represents 1 to 6

Z represents —NO$_2$, -halogen, —CN, —CF$_3$ or —SO$_2$Me; and where each W is independently selected from halogen or —OSO$_2$Me and pharmaceutically acceptable salts thereof the method comprising the step of phosphorylating a compound represented by formulae (IIa), (IIb) or (IIc)

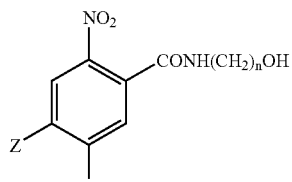
(IIa)

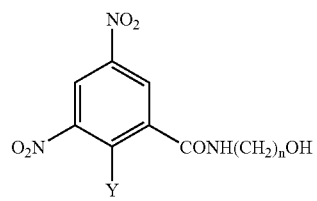
(IIb)

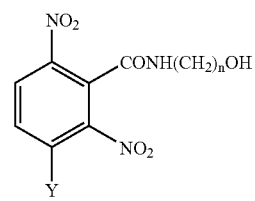
(IIc)

wherein Y represents

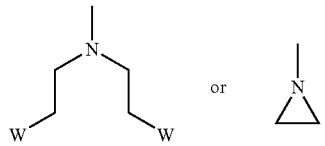

and wherein n represents 1 to 6

Z represents —NO$_2$, -halogen, —CN, —CF$_3$ or —SO$_2$Me; and where each W is independently selected from halogen or —OSO$_2$Me and pharmaceutically acceptable salts.

6. A method of killing hypoxic cells in a tumour comprising the step of administering an amount of a compound of Formula (I) as defined above in claim 1 to a subject with the tumour.

7. A method of cell ablation utilising at least one nitroreductase enzyme comprising the step of using a compound of Formula (I) as defined above in claim 1 in an effective amount to ablate cells which express at least one nitroreductase enzyme.

8. A method of cell ablation utilising at least one nitroreductase enzyme comprising the step of administering a compound of Formula (I) as defined above in claim 1 in an effective amount to a subject to ablate cells which express at least one nitroreductase enzyme.

9. The method as claimed in claim 8 wherein the at least one nitroreductase enzyme is encoded for by the nfsB gene of either *E. coli* or by orthologous genes in *Clostridia* species.

10. The method as claimed in claim 8 wherein the cells that express the at least one nitroreductase enzyme are tumour cells in tissue in the subject.

11. The method as claimed in claim 8 wherein the cell ablation is achieved through GDEPT (gene-directed enzyme-prodrug therapy).

12. The method as claimed in claim 8 wherein the cell ablation is achieved through ADEPT (antibody-directed enzyme-prodrug therapy).

13. The method as claimed in claim 8 wherein the cells are mammalian.

14. The method as claimed in claim 8 wherein the amount administered is between about 20% to 100% of the maximum tolerated dose of the subject.

15. The method as claimed in claim 8 including the further step of applying irradiation or one or more chemotherapeutic agents to the subject.

16. A pharmaceutical composition comprising a therapeutically effective amount of a compound of Formula (I) as defined in claim 1 and a pharmaceutically acceptable excipient, adjuvant, carrier, buffer or stabiliser.

17. A compound selected from:
2-[(2-Bromoethyl)-2,4-dinitro-6-[[[2-(phosphonooxy)ethyl]amino]-carbonyl]anilino]ethyl methanesulfonate;
2-[(2-Bromoethyl)-2,4-dinitro-3-[[[2-(phosphonooxy)ethyl]amino]-carbonyl]anilino]ethyl methanesulfonate;
2-[(2-Bromoethyl)-2,4-dinitro-3-[[[3-(phosphonooxy)propyl]amino]-carbonyl]anilino]ethyl methanesulfonate; and
2-[(2-iodoethyl)-2,4-dinitro-3-[[[3-(phosphonooxy)propyl]amino]-carbonyl]anilino]ethyl methanesulfonate.

18. The compound
2-[(2-Bromoethyl)-2,4-dinitro-6-[[[2-(phosphonooxy)ethyl]amino]-carbonyl]anilino]ethyl methanesulfonate.

19. A pharmaceutical composition comprising a therapeutically effective amount of a compound as claimed in claim 17 or claim 18 and a pharmaceutically acceptable excipient, adjuvant, carrier, buffer or stabiliser.

20. A method of killing hypoxic cells in a tumor comprising the step of administering an effective amount of a compound of claim 18 to a subject with a tumor.

* * * * *

UNITED STATES PATENT AND TRADEMARK OFFICE
CERTIFICATE OF CORRECTION

| | | |
|---|---|---|
| PATENT NO. | : 7,629,332 B2 | Page 1 of 1 |
| APPLICATION NO. | : 10/577078 | |
| DATED | : December 8, 2009 | |
| INVENTOR(S) | : Denny et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 307 days.

Signed and Sealed this

Twenty-first Day of December, 2010

David J. Kappos
*Director of the United States Patent and Trademark Office*